US010815290B2

(12) United States Patent
Gewe et al.

(10) Patent No.: US 10,815,290 B2
(45) Date of Patent: Oct. 27, 2020

(54) NKG2D DECOYS

(71) Applicant: Fred Hutchinson Cancer Research Center, Seattle, WA (US)

(72) Inventors: Mesfin Gewe, Seattle, WA (US); Roland K. Strong, Seattle, WA (US); Martin Prlic, Seattle, WA (US); Peter Rupert, Seattle, WA (US); Thomas Spies, Seattle, WA (US); Veronika Spies, Seattle, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 196 days.

(21) Appl. No.: 15/775,298

(22) PCT Filed: Nov. 10, 2016

(86) PCT No.: PCT/US2016/061368
§ 371 (c)(1),
(2) Date: May 10, 2018

(87) PCT Pub. No.: WO2017/083545
PCT Pub. Date: May 18, 2017

(65) Prior Publication Data
US 2018/0371051 A1 Dec. 27, 2018

Related U.S. Application Data

(60) Provisional application No. 62/253,590, filed on Nov. 10, 2015.

(51) Int. Cl.
| C07K 5/00 | (2006.01) |
| C07K 14/705 | (2006.01) |
| C07K 16/28 | (2006.01) |
| A61P 35/00 | (2006.01) |
| A61K 39/39 | (2006.01) |
| C07K 14/47 | (2006.01) |
| A61K 38/00 | (2006.01) |
| A61K 39/00 | (2006.01) |

(52) U.S. Cl.
CPC .......... *C07K 14/7056* (2013.01); *A61K 39/39* (2013.01); *A61P 35/00* (2018.01); *C07K 14/47* (2013.01); *C07K 14/4705* (2013.01); *C07K 16/2833* (2013.01); *C07K 16/2851* (2013.01); *A61K 38/00* (2013.01); *A61K 2039/505* (2013.01); *A61K 2039/55516* (2013.01); *C07K 2317/76* (2013.01); *C07K 2319/00* (2013.01); *C07K 2319/43* (2013.01); *C07K 2319/50* (2013.01); *C07K 2319/70* (2013.01); *C07K 2319/74* (2013.01)

(58) Field of Classification Search
None
See application file for complete search history.

(56) References Cited

U.S. PATENT DOCUMENTS

2011/0311535 A1 12/2011 Dranoff et al.

FOREIGN PATENT DOCUMENTS

| CN | 102020717 | 4/2011 |
| CN | 104894151 A | 9/2015 |
| WO | WO1991011461 A1 | 8/1991 |
| WO | WO2003089616 | 10/2003 |
| WO | WO2003089616 A2 | 10/2003 |
| WO | WO2005097160 | 10/2005 |
| WO | WO2005097160 A2 | 10/2005 |
| WO | WO2010080124 A2 | 7/2010 |
| WO | WO2014093403 | 6/2014 |
| WO | WO2014093403 A1 | 6/2014 |

OTHER PUBLICATIONS

Dietrich, et al., "Peptides as Drugs: From Screening to Application", Current Pharmaceutical Biotechnology, vol. 14, No. 5, Bentham Science Publishers, 2013, pp. 1-12.
Li, et al., "Complex structure of the activating immunoreceptor NKG2D and its MHC class I-like ligand MICA," Nat. Immunol., vol. 2, No. 5, 2001, pp. 443-451.
McFarland and Strong, "Thermodynamic Analysis of Degenerate Recognition by the NKG2D Immunoreceptor," Immunity, vol. 19, 2003, pp. 803-812.
McFarland, et al., "Symmetry recognizing asymmetry: analysis of the interactions between the C-type lectin-like immunoreceptor NKG2D and MHC class I-like ligands," Structure, vol. 11, No. 4, 2003, pp. 411-422.
Invitation to Pay Additional Fees dated Feb. 6, 2017 for International Application No. PCT/US2016/061368.
Search Report and Written Opinion dated Apr. 21, 2017 in International Application No. PCT/US2016/061368.
Strong and McFarland, "NKG2D and related immunoreceptors," Adv. Protein Chem., vol. 68, 2004, pp. 281-312.
Bauer, et al., "Activation of NK cells and T cells by NKG2D, a receptor for stress-inducible MICA," Science, vol. 285, No. 5428, 1999, pp. 727-729.

(Continued)

*Primary Examiner* — Michail A Belyavskyi
(74) *Attorney, Agent, or Firm* — Lee & Hayes PC; C. Rachal Winger

(57) ABSTRACT

Single chain, multimerized, and/or glycosylated NKG2D decoys are described. The NKG2D decoys have high affinity and avidity for surface bound and soluble NKG2D ligands and can be used to (i) identify NKG2D ligands; (ii) treat cancer, graft vs. host disease (GVHD), and inflammatory conditions; and (iii) potentiate an immune response against a vaccine as well as many other potential uses.

17 Claims, 42 Drawing Sheets

Specification includes a Sequence Listing.

(56) References Cited

OTHER PUBLICATIONS

Blom, et al., "Complement inhibitor C4b-binding protein-friend or foe in the innate immune system," Mol. Immunol., vol. 40, No. 18, 2004, pp. 1333-1346.
Cai, et al. "Autonomous Stimulation of Cancer Cell Plasticity by the Human NKG2D Lymphocyte Receptor Coexpressed with Its Ligands on Cancer Cells," PLoS One, vol. 9, No. 10, 2014, 13 pages.
Dissen, et al., "An Autosomal Dominant Locus, Nka, Mapping to the Ly-49 Region of a Rat Natural Killer (NK) gene Complex, Controls NK Cell Lysis of Allogeneic Lymphocytes," J. Exp. Med., vol. 183, 1996, pp. 2197-2207.
Dontu, et al., "In vitro propagation and transcriptional profiling of human mammary stem/progenitor cells," Genes Dev, vol. 17, No. 10, 2003, pp. 1253-1270.
Forbes, et al., "T Cell Responses Induced by Adenoviral Vectored Vaccines Can Be Adjuvanted by Fusion of Antigen to the Oligomerization Domain of C4b-Binding Protein," PLoS One, vol. 7, No. 9, 2012, 12 pages.
Ho, et al., "Murine Nkg2d and Cd94 are clustered with in the natural killer complex and are expressed independently in natural killer cells," PNAS, USA, vol. 95, 1998, pp. 6320-6325.
Hofmeyer, et al., "Arranged sevenfold: structural insights into the C-terminal oligomerization domain of human C4b-binding protein," J. Mol. Biol., vol. 425, No. 8, 2013, pp. 1302-1317.
Ito, et al., "NK cells contribute to the skin graft rejection promoted by CD4+ T cells activated through the indirect allrecognition pathway," International Immunology, vol. 20, No. 10, 2008, pp. 1343-1349.
Karimi, et al., "NKG2d Expression by CD8+ T cells contribute to GVHD and GVT effects in murine model of allogenic HSCT," Blood, vol. 125, No. 23, 2015, pp. 3655-3663.
Kask, et al. "Structural requirements for the intracellular subunit polymerization of the complement inhibitor C4b-biding protein," Biochemistry, vol. 41, No. 30, 2002, pp. 9349-9357.
Kim, et al., "A novel multiparametric flow cytometry-based cytotoxicity assay simultaneously immunophenotypes effect cells: Comparisons to a 4 h 51Cr-release assay," J. Immunol. Methods, vol. 325, No. 1-2, 2007, pp. 51-66.
Kwong, et al., "Generation, affinity maturation, and characterization of a human anti-human NKG2D monoclonal antibody with dual antagonistic and agnostic activity," J. Mol. Biol., vol. 384, No. 5, 2008, pp. 1143-1156.
Lengyel, et al., "Mutations designed to destabilize the receptor-bound conformation increase MICA-NKG2D association rate and affinity," J. Biol. Chem., vol. 282, No. 42, 2007, pp. 30658-30666.
Nausch, et al, "NKG2D ligands in tumor immunity," Oncogene, vol. 27, No. 45, 2008, pp. 5594-5958.
PCT Invitation to Pay Additional Fees dated Feb. 6, 2017 for International Application No. PCT/US2016/061368, 3 pages.
Spear, et al., "NKG2D ligands as therapeutic targets," Cancer Immunity, vol. 13, 2013, 14 pages.
Search Report and Written Opinion dated Apr. 21, 2017 in International Patent Application No. PCT/US2016/061368, 16 pages.
Steigerwald, et al., "Human IgG1 antibodies antagonizing receptor NKG2D on natural killer cells," mAbs, vol. 1, No. 2, 2009, pp. 115-127.
Verneris, et al., "Role of NKG2D signaling in the cytotoxicity of activated and expanded CD8+ T cells," Blood, vol. 103, No. 8, 2004, pp. 3065-3072.
Wu, et al., "An activating immunoreceptor complex formed by NKG2D and DAP10," Science, vol. 285, No. 5428, 1999 pp. 730-732.
Allred, et al., "Siderocalin-mediated recognition, sensitization, and cellular uptake of actinides," PNAS, vol. 112, No. 33, 2015, pp. 10342-10347.
Cai, et al., "Control of Tumor Initiation by NKG2D Naturally Expressed on Ovarian Cancer Cells," Neoplasia, vol. 19, No. 6, 2017, pp. 471-482.
Extended European Search Report dated Apr. 24, 2019 in European Application No. 16865019.0, 10 pages.
Garrity, et al., "The activating NKG2D receptor assembles in the membrane with two signaling dimers into a hexameric structure," PNAS, vol. 102, No. 21, 2005, pp. 7641-7646.
Ogun, et al., "The oligomerization domain of C4-binding protein (C4bp) acts as an adjuvant, and the fusion protein comprised of the 19-kilodalton merozoite surface protein 1 fused with the murine C4bp domain protects mice against malaria," Infect. Immun., vol. 76, No. 8, 2008, pp. 3817-3823.
Stark, et al., "The use of trimeric isoleucine-zipper fusion proteins to study surface-receptor-ligand interactions in natural killer cells," J. Immunol. Methods., vol. 296, No. 1-2, 2005, pp. 149-158.
Xia, et al., "Treatment with a fusion protein of the extracellular domains of NKG2D to IL-15 retards colon cancer growth in mice," J. Immunother, vol. 37, No. 5, 2014, pp. 257-266.
Yan, et al., "Delivery of human NKG2D-IL-15 fusion gene by chitosan nanoparticles to enhance antitumor immunity," Biochem. Biophys. Res. Commun., vol. 463, No. 3, 2015, pp. 336-343.

FIG. 1 (cont'd)
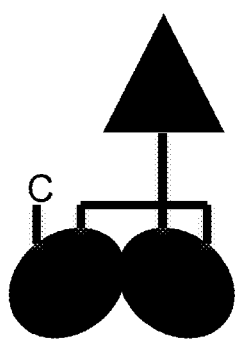
NKG2D$^{scd}$
+ multimerization domain
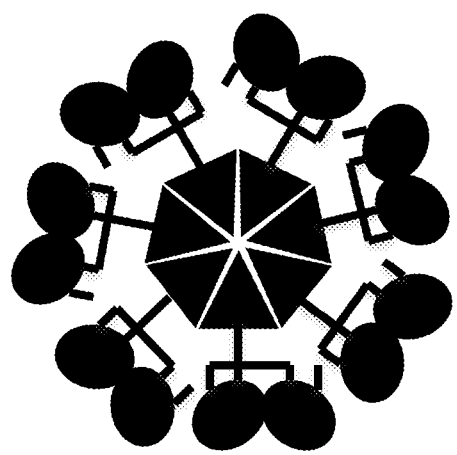
heptavalent
NKG2D$^{scd}$ multimer
(NKG2D$_7$ or NKG2D heptamer)

FIG. 2

| Parameter | Total (n=47) | NKG2D Low (n=24) | NKG2D High (n=23) |
|---|---|---|---|
| % NKG2D$^+$ cells (median, min-max) | 1.79 (0.00-66.90) | 0.93 (0.00-1.79) | 12.87 (2.18-66.90) |
| Age (median, lowest-highest) | 61 (38-82) | 62 (38-82) | 59 (44-77) |
| FIGO* Stage (n, %) | | | |
| I/II | 9 (19) | 6 (25) | 3 (13) |
| III/IV | 38 (81) | 18 (75) | 20 (87) |
| Outcome (n, %) | | | |
| ANED** | 27 (57) | 19 (79) | 8 (35) |
| Recurrence | 14 (30) | 3 (13) | 11 (48) |
| DOD*** | 6 (13) | 2 (8) | 4 (17) |

Abbreviations: * FIGO, International Federation of Gynecologists and Obstetricians;
**ANED, alive, no evidence of disease;
***DOD, died of disease.

FIG. 4

| Parameter | Total EOC* Cases (n=47) | NKG2D Low Subgroup (n=24) | NKG2D High Subgroup (n=24) | P value |
|---|---|---|---|---|
| Recurrence (n, %) | | | | 0.001 |
| No | 30 (64) | 21 (88) | 9 (39) | |
| Yes | 17 (35) | 3 (12) | 14 (61) | |

P value results from likelihood ratio test and is adjusted for age.
Abbreviation: *EOC, epithelial ovarian cancer.

FIG. 5

| Specimen ID | Type/Histology (31) | Grade | FIGO* Stage |
|---|---|---|---|
| EOC**1 | Type II/Serous[1] | 3 | IIIC |
| EOC2 | Type II/Serous | 3 | IIIC |
| EOC3 | Type II/Serous | 3 | IIIC |
| EOC4 | Type II/Serous | 3 | IIIC |
| EOC5 | Type II/Serous | 3 | IIIA |
| EOC6 | Type II/Serous | 3 | IIIB |
| EOC7 | Type II/Serous | 3 | IIIC |
| EOC8 | Type II/Serous | 3 | IIIC |
| EOC9 | Type II/Serous | 3 | IIIA |
| EOC10 | Type II/Serous | 3 | IIIC |
| EOC11 | Type II/Serous | 3 | IIIC |
| EOC12 | Type II/Serous | 3 | IIIC |
| EOC13 | Type I/Clear Cell[2] | 3 | IA |
| EOC14 | Type I/Clear Cell | 3 | IA |
| EOC15 | Type I/Clear Cell | 3 | IC |
| EOC16 | Type II/Serous | 3 | IV |
| EOC17 | Type II/Serous | 3 | IIIC |
| EOC18 | Type II/Serous | 3 | IV |
| EOC19 | Type II/Serous | 3 | IIIC |
| EOC20 | Type II/Serous | 3 | IIIC |
| EOC21 | Type II/Serous | 3 | IIB |
| EOC22 | Type II/Serous | 3 | IC |
| EOC23 | Type II/Serous | 3 | IIIC |
| EOC24 | Type II/Serous | 3 | IIIC |
| EOC25 | Type II/Serous | 3 | IIIC |
| EOC26 | Type II/Serous | 3 | IC |
| EOC27 | Type II/Serous | 3 | IIC |
| EOC28 | Type II/Serous | 3 | IIIC |
| EOC29 | Type II/Serous | 3 | IIIC |
| EOC30 | Type I/Endometrioid[3] | 1 | IC |
| EOC31 | Type I/Endometrioid | 1 | IIB |
| EOC32 | Type I/Endometrioid | 1 | IA |
| EOC33 | Type I/Endometrioid | 2 | IA |
| EOC34 | Type II/Serous | 3 | IIIC |
| EOC35 | Type II/Serous | 3 | IIIC |
| EOC36 | Type I/Endometrioid | 2 | IIA |
| EOC37 | Type II/Serous | 3 | IIIC |
| EOC38 | Type II/Serous | 3 | IIC |
| EOC39 | Type II/Serous | 3 | IC |
| EOC40 | Type I/Endometrioid | 2 | IIA |
| EOC41 | Type I/Clear Cell | 3 | IC |
| EOC42 | Type II/Serous | 3 | IIIC |
| EOC43 | Type II/Serous | 3 | IIIC |
| EOC44 | Type I/Mucinous[4] | 1 | IC |
| EOC45 | Type II/Serous | 3 | IIIC |

Abbreviations: *FIGO, International Federation of Gynecologists and Obstetricians, **EOC, epithelial ovarian cancer. Footnotes: [1]high grade serous carcinoma, [2]clear cell carcinoma, [3]endometrioid carcinoma, [4]mucinous carcinoma

FIG. 6

| Specimen ID | | % EpCAM$^+$CD44$^+$ cells among NKG2D$^+$ cells | % EpCAM$^+$CD44$^+$ cells among NKG2D$^-$ cells |
|---|---|---|---|
| EOC*1 | | 8.49 | 2.8 |
| EOC2 | | 72.3 | 6.79 |
| EOC3 | | 5.37 | 0.84 |
| EOC4 | | 7.54 | 0 |
| EOC5 | | 74 | 7.19 |
| | Average +/- SD | 33.5 +/- 36.2 | 3.5 +/- 3.3 |
| | | % ALDEFLUOR$^{high}$ cells among NKG2D$^+$ cells | % ALDEFLUOR$^{high}$ cells among NKG2D$^-$ cells |
| EOC6 | | 21.4 | 10.2 |
| EOC7 | | 68.4 | 6.8 |
| EOC8 | | 37.6 | 7.8 |
| EOC9 | | 23.1 | 5.3 |
| EOC10 | | 35.1 | 8 |
| EOC11 | | 13.9 | 2.7 |
| EOC12 | | 12.1 | 2 |
| | Average +/- SD | 30.2 +/- 19.4 | 6.1 +/- 3 |
| EOC13 | | 64.9 | 6.02 |
| EOC14 | | 19.6 | 5.14 |
| EOC 15 | | 6.56 | 2.54 |
| | Average +/- SD | 30.4 +/- 30.1 | 4.6 +/- 2 |

Abbreviations: *EOC, epithelial ovarian cancer.

| Cells plated | NKG2D | EOC16 | EOC17 | EOC18 | EOC19 | EOC20 | EOC21 | EOC22 | EOC23 |
|---|---|---|---|---|---|---|---|---|---|
| 5 000 | pos |  | 28 | 74 | 39 | 15 | 41 | 27/8/3 | 37/24/5 |
|  | neg |  | 6 | 8 | 0 | 0 | 1 | 9/1/00 | 1/0/0 |
| 10 000 | pos | 52 |  |  |  |  |  |  |  |
|  | neg | 2 |  |  |  |  |  |  |  |
| 50 000 | pos |  |  |  |  |  |  |  |  |
|  | neg |  | 13 | 14 |  |  |  | 27 | 18 |

| Tissue ID | NKG2D | Cell Numbers | | Frequency | P value |
|---|---|---|---|---|---|
| | | 5000 | 10000 | | |
| EOC34 | pos | 1/4 | 2/4 | 1/15431 | 0.0259 |
| | neg | 0/4 | 0/4 | 1/infinite | |
| EOC35 | pos | 2/3 | 4/4 | 1/3343 | 0.00329 |
| | neg | 0/3 | 1/4 | 1/49833 | |
| EOC36 | pos | 1/2 | 1/2 | 1/10772 | 0.0629 |
| | neg | 0/2 | 0/2 | 1/infinite | |

FIG. 9A
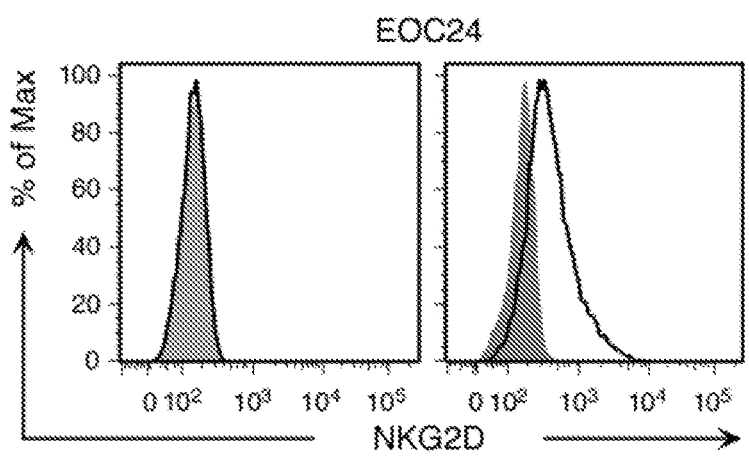
FIG. 9B
| Cells plated | NKG2D | EOC30 | EOC31 | EOC32 | EOC33 |
|---|---|---|---|---|---|
| 5 000 | pos | 20 | 29 | 52 | 48 |
|  | neg | 1 | 1 | 0 | 10 |
| 10 000 | pos |  |  | 69 |  |
|  | neg |  |  | 0 |  |
| 50 000 | pos |  |  |  |  |
|  | neg |  | 4 |  | 35 |
FIG. 9C
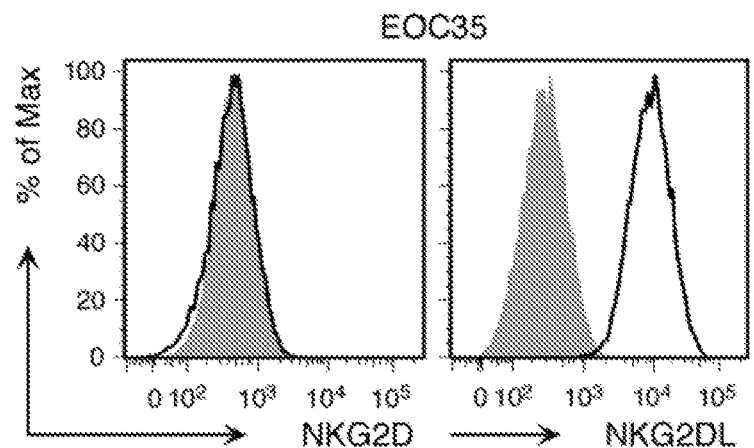

FIG. 10C

MDAH-2774

| Mouse ID | Cell number | 1 | 2 | 3 | 4 | 5 | 6 | 7 | 8 |
|---|---|---|---|---|---|---|---|---|---|
| 26LT | 10000 | | | | | | | | |
| 26LB | | | | | | | | | |
| 26RT | | | | | | | | | |
| 26RB | | | | | | | | | |
| 27LT | 1000 | | | | | | | | |
| 27LB | | | | | | | | | |
| 27RT | | | | | | | | | |
| 27RB | | | | | | | | | |
| 28LT | 100 | | | | | | | | |
| 28LB | | | | | | | | | |
| 28RT | | | | | | | | | |
| 28LB | | | | | | | | | |

MDAH-2774-TF

| Mouse ID | Cell number | 1 | 2 | 3 | 4 | 5 | 6 | 7 | 8 |
|---|---|---|---|---|---|---|---|---|---|
| 32LT | 10000 | | | | | | | | |
| 32LB | | | | | | | | | |
| 32RT | | | | | | | | | |
| 32RB | | | | | | | | | |
| 33LT | 1000 | | | | | | | | |
| 33LB | | | | | | | | | |
| 33RT | | | | | | | | | |
| 33RB | | | | | | | | | |
| 34LT | 100 | | | | | | | | |
| 34LB | | | | | | | | | |
| 34RT | | | | | | | | | |
| 34RB | | | | | | | | | |

MDAH-2774 mock

| Mouse ID | Cell number | 1 | 2 | 3 | 4 | 5 | 6 | 7 | 8 |
|---|---|---|---|---|---|---|---|---|---|
| 29LT | 10000 | | | | | | | | |
| 29LB | | | | | | | | | |
| 29RT | | | | | | | | | |
| 29RB | | | | | | | | | |
| 30LT | 1000 | | | | | | | | |
| 30LB | | | | | | | | | |
| 30RT | | | | | | | | | |
| 30RB | | | | | | | | | |
| 31LT | 100 | | | | | | | | |
| 31LB | | | | | | | | | |
| 31RT | | | | | | | | | |
| 31RB | | | | | | | | | |

MDAH-2774-TF-KO

| Mouse ID | Cell number | 1 | 2 | 3 | 4 | 5 | 6 | 7 | 8 |
|---|---|---|---|---|---|---|---|---|---|
| 56LT | 10000 | | | | | | | | |
| 56LB | | | | | | | | | |
| 56RT | | | | | | | | | |
| 56RB | | | | | | | | | |
| 50LT | 1000 | | | | | | | | |
| 50LB | | | | | | | | | |
| 50RT | | | | | | | | | |
| 50RB | | | | | | | | | |
| 51LT | 100 | | | | | | | | |
| 51LB | | | | | | | | | |
| 51RT | | | | | | | | | |
| 51RB | | | | | | | | | |

FIG. 10D

| Treatment | MDAH-2774-TF cells injected/ tumors formed | |
|---|---|---|
| | 1000 | 100 |
| IgG local | 4/4 | 3/4 |
| NKG2DL Abs local | 2/4 | 0/4 |
| IgG i.v. | 4/4 | 3/4 |
| NKG2DL Abs i.v. | 1/4 | 0/4 |

4B0F.pdb

1HYR.pdb

NKG2D$^{scd}_7$

FIG. 13A

METDTLLLWVLLLWVPGSTG//DYKDE//HHHHHH//GGS//QDSTSDLIPAPPLSKVPLQQNFQDN
QFQGKWYVVGLAGNAILREDKDPQKMYATIYELKEDKSYNVTSVLFRKKKCDYWIRTFVPGSQ
PGEFTLGNIKSYPGLTSYLVRVVSTNYNQHAMVFFKKVSQNREYFKITLYGRTKELTSELKENFIR
FSKSLGLPENHIVFPVPIDQCID//GGGS//ENLYFQ//GSRSAGAHAGWETPEGCEQVLTGKRLMQ
CLPNPEDVKMALEVYKLSLEIEQLELQRDSARQSTLDKEL//NQEVQIPLTE//SYCGPCPKNWICY
KNNCYQFFDESKNWYESQASCMSQNASLLKVYSKEDQDLLKLVKSYHWMGLVHIPTNGSWQ
WEDGSILSPNLLTIIEMQKGDCALYASSFKGYIENCSTPNTYICMQRTV//QIPLTE//SYCGPCPKN
WICYKNNCYQFFDESKNWYESQASCMSQNASLLKVYSKEDQDLLKLVKSYHWMGLVHIPTNG
SWQWEDGSILSPNLLTIIEMQKGDCALYASSFKGYIENCSTPNTYICMQRTV (SEQ ID NO: 78)

SEQ ID NO: 78 includes: Igκ leader peptide // FLAG tag // His$_6$ tag // G/S linker // Siderocalin fusion partner // G/S linker // TEV scission site // C4bbp multimerization domain // NKG2D N-terminal arm (linker) // NKG2D monomer #1 // NKG2D N-terminal arm (linker) // NKG2D monomer #2

GSRSAGAHAGWETPEGCEQVLTGKRLMQCLPNPEDVKMALEVYKLSLEIEQLELQRDSARQS
TLDKEL//NQEVQIPLTE//SYCGPCPKNWICYKNNCYQFFDESKNWYESQASCMSQNASLLKVY
SKEDQDLLKLVKSYHWMGLVHIPTNGSWQWEDGSILSPNLLTIIEMQKGDCALYASSFKGYIENC
STPNTYICMQRTV//QIPLTE//SYCGPCPKNWICYKNNCYQFFDESKNWYESQASCMSQNASLL
KVYSKEDQDLLKLVKSYHWMGLVHIPTNGSWQWEDGSILSPNLLTIIEMQKGDCALYASSFKGYI
ENCSTPNTYICMQRTV (SEQ ID NO: 83)

SEQ ID NO: 83 includes: C4bbp multimerization domain // NKG2D N-terminal arm (linker) // NKG2D monomer #1 // NKG2D N-terminal arm (linker) // NKG2D monomer #2

C4b multimerization domain: GSRSAGAHAGWETPEGCEQVLTGKRLMQCLPNPEDVKMA
LEVYKLSLEIEQLELQRDSARQSTLDKEL (SEQ ID NO. 80)

[First] NKG2D N-terminal arm (linker): NQEVQIPLTE (SEQ ID. NO. 81)

NKG2D monomer #1: SYCGPCPKNWICYKNNCYQFFDESKNWYESQASCMSQNASLLKVYS
KEDQDLLKLVKSYHWMGLVHIPTNGSWQWEDGSILSPNLLTIIEMQKGDCALYASSFKGYIENCS
TPNTYICMQRTV (SEQ ID NO: 79)

[Second] NKG2D N-terminal arm (linker): QIPLTE (SEQ ID NO. 82)

NKG2D monomer #2: SYCGPCPKNWICYKNNCYQFFDESKNWYESQASCMSQNASLLKVYS
KEDQDLLKLVKSYHWMGLVHIPTNGSWQWEDGSILSPNLLTIIEMQKGDCALYASSFKGYIENCS
TPNTYICMQRTV (SEQ ID NO: 79)

FIG. 13B

MGWIRGRRSRHSWEMSEFHNYNLDLKKSDFSTRWQKQRCPVVKSKCRENASPFFFCCFIAVA
MGIRFIIMVTIWSAVFLNSLFNQEVQIPLTESYCGPCPKNWICYKNNCYQFFDESKNWYESQASC
MSQNASLLKVYSKEDQDLLKLVKSYHWMGLVHIPTNGSWQWEDGSILSPNLLTIIEMQKGDCAL
YASSFKGYIENCSTPNTYICMQRTV (SEQ ID NO: 76)

Human NKG2D

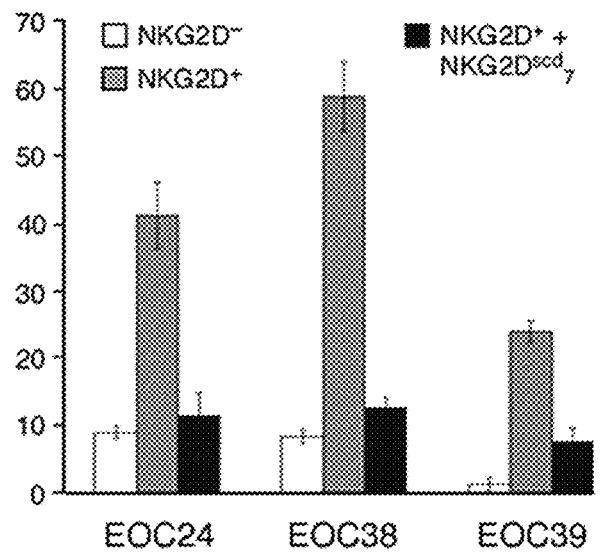
FIG. 16A
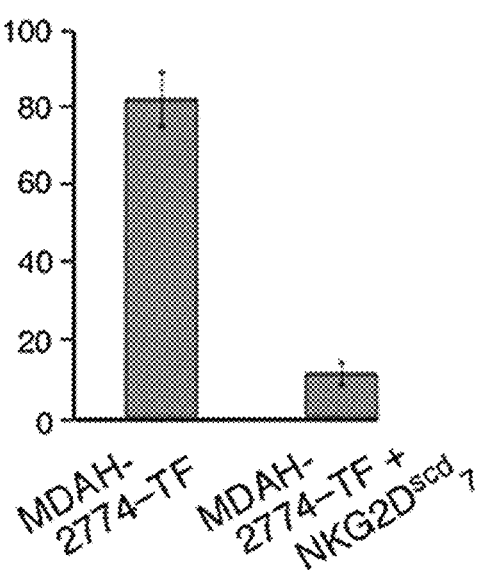
FIG. 16B
FIG. 16C
| Specimen ID | Treatment | Number of NKG2D+ cells injected | |
|---|---|---|---|
| | | 15000 | 5000 |
| | | Tumors formed | |
| EOC40 | PBS local | | 3/4 |
| | NKG2Dscd7 local | | 0/4 |
| EOC41 | PBS local | | 2/4 |
| | NKG2Dscd7 local | | 0/4 |
| EOC42 | PBS local | 3/4 | |
| | NKG2Dscd7 i.v. | 1/4 | |
FIG. 16D
| Specimen ID | Treatment | Number of unsorted cells injected |
|---|---|---|
| | | 10000 |
| | | Tumors formed |
| EOC43 | scrRNAi | 2/2 |
| | NKG2DRNAi | 0/2 |
| EOC44 | PBS local | 3/4 |
| | NKG2Dscd7 local | 0/4 |
| EOC45 | PBS local | 2/4 |
| | NKG2Dscd7 local | 0/4 |

1. 1x10⁴ naïve OT-I T cells
2. VSV-OVA (i.v., 1x10⁶ pfu)

B6

>30 days

Day 0: Infect
With WT-LM

Days 2-5

Examine bystander-activation

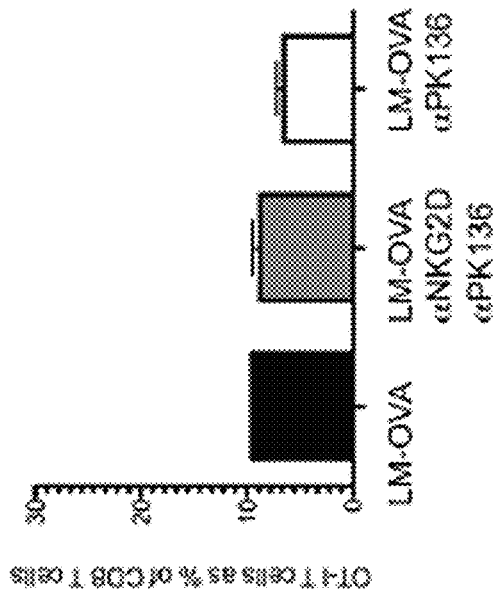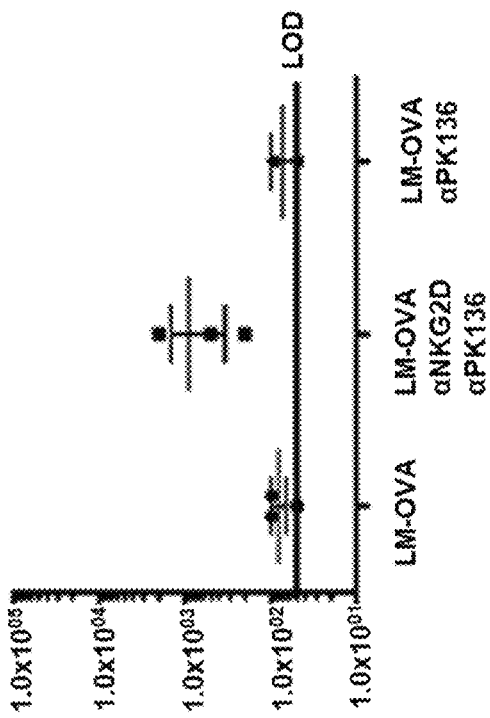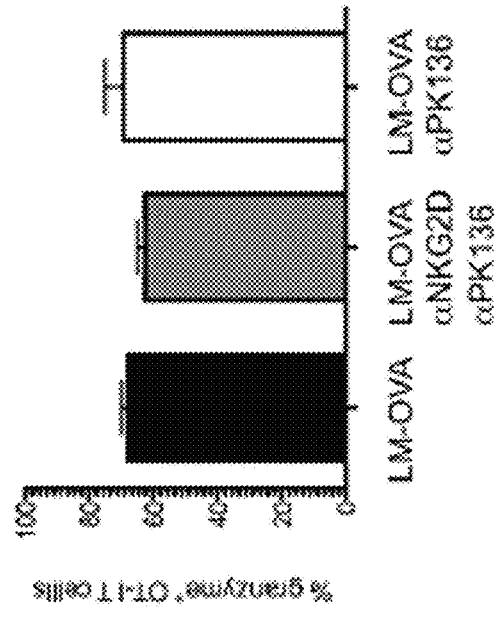
FIG. 21A
FIG. 21B
FIG. 21C

Left=RMA cells
Right=RMA-Rae1 cells

FIG. 27
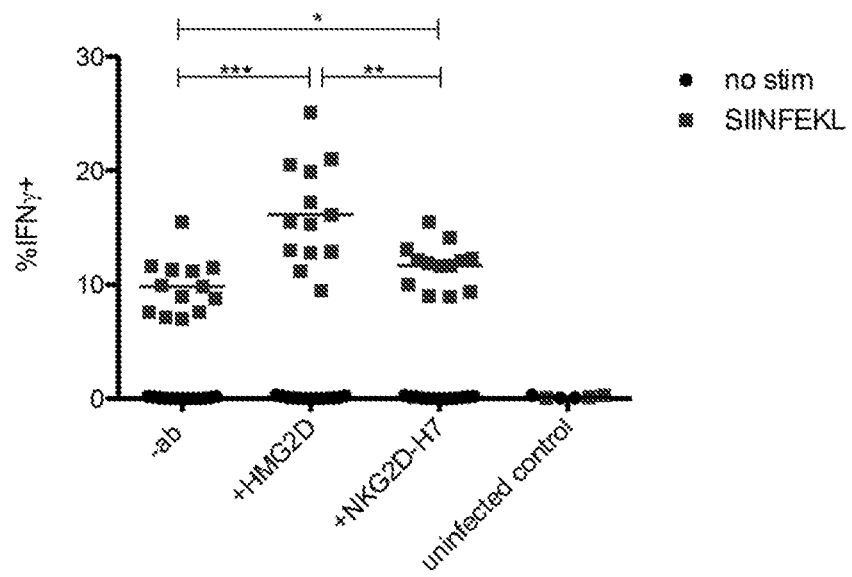
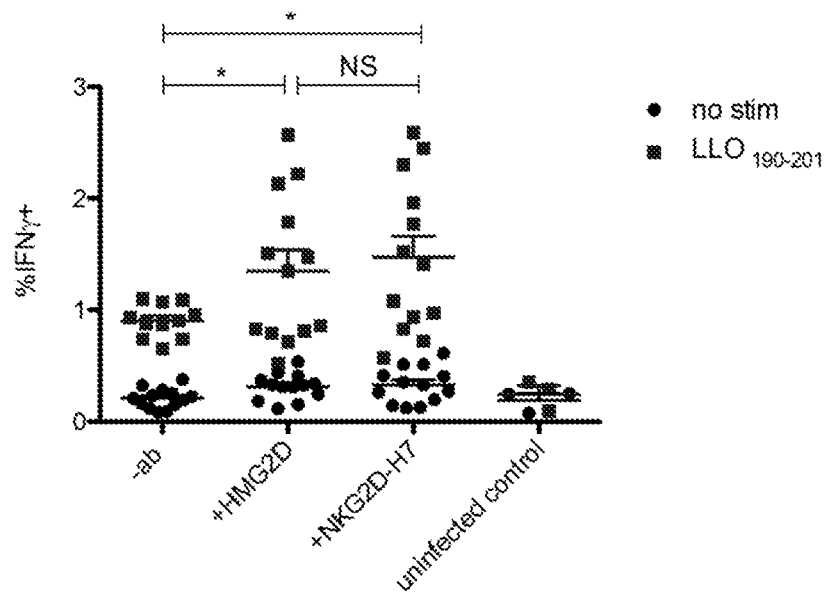

FIG. 28
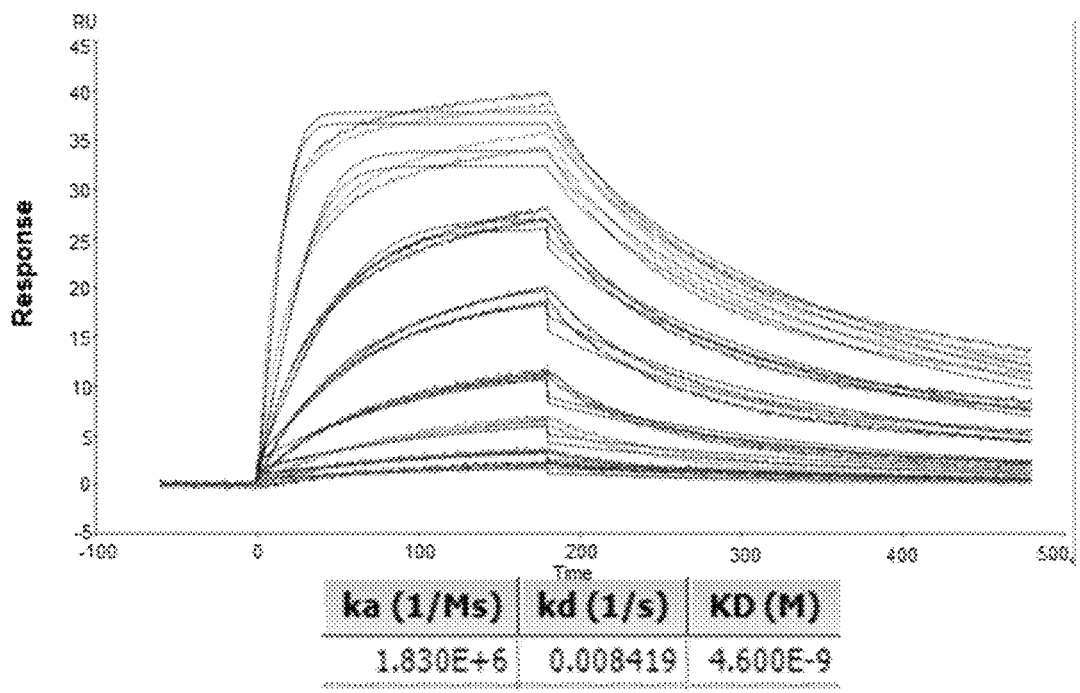
1:1 binding model
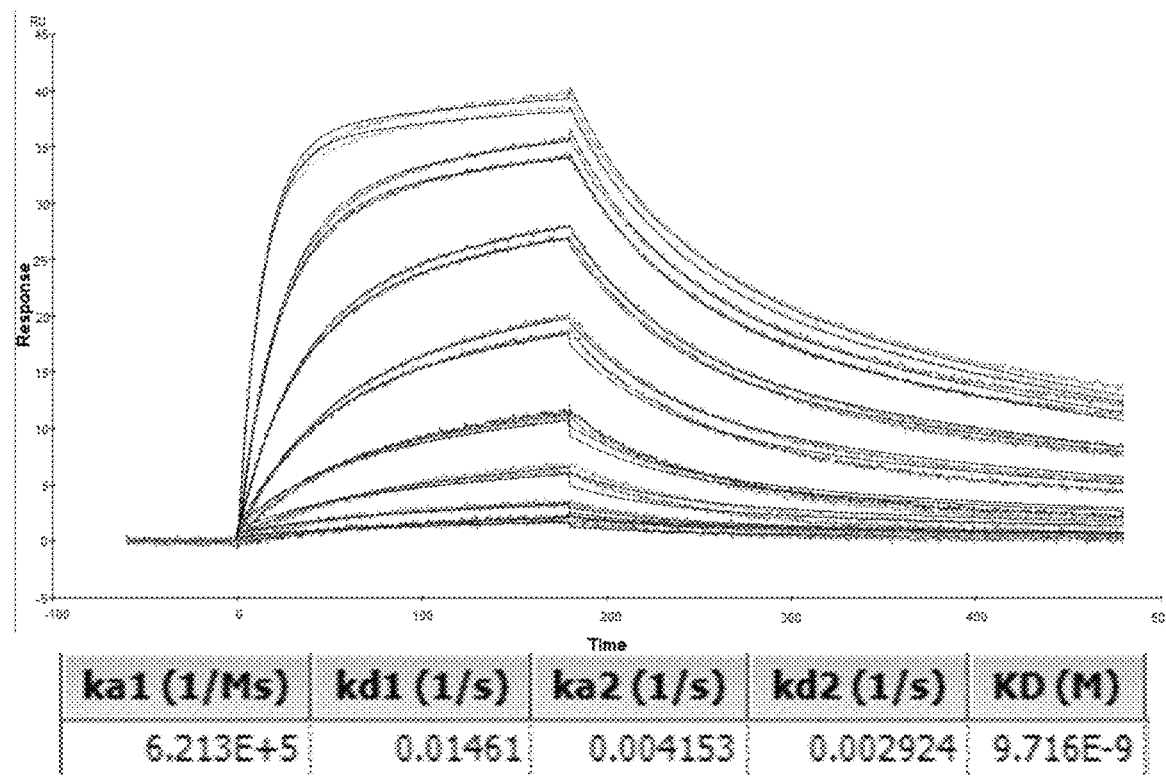
Two State Reaction model

FIG. 29

SEQ ID NO: 45: *H. sapiens* Scn
QDSTSDLIPAPPLSKVPLQQNFQDNQFQGKWYVVGLAGNAILREDKDPQKMYATIYELKE
DKSYNVTSVLFRKKKCDYWIRTFVPGCQPGEFTLGNIKSYPGLTSYLVRVVSTNYNQHAM
VFFKKVSQNREYFKITLYGRTKELTSELKENFIRFSKSLGLPENHIVFPVPIDQCIDG SEQ ID NO: 46: *M. musculus* Scn
QDSTQNLIPAPSLLTVPLQPDFRSDQFRGRWYVVGLAGNAVQKKTEGSFTMYSTIYELQE
NNSYNVTSILVRDQDQGCRYWIRTFVPSSRAGQFTLGNMHRYPQVQSYNVQVATTDYN
QFAMVFFRKTSENKQYFKITLYGRTKELSPELKERFTRFAKSLGLKDDNIIFSVPTDQCIDN SEQ ID NO: 47: *R. norvegicus* Scn
QDSTQNLIPAPPLISVPLQPGFWTERFQGRWFVVGLAANAVQKERQSRFTMYSTIYELQE
DNSYNVTSILVRGQGCRYWIRTFVPSSRPGQFTLGNIHSYPQIQSYDVQVADTDYDQFAM
VFFQKTSENKQYFKVTLYGRTKGLSDELKERFVSFAKSLGLKDNNIVFSVPTDQCIDN SEQ ID NO: 48: *P. troglodytes* Scn
QDSTSDLIPAPPLSKVPLQQNFQDNQFQGKWYVVGLAGNAILREDKDPQKMYATIYELKE
DKSYNVTSVLFRKKKCDYWIRTFVPGRQPGEFTLGNIKSYPGLTSYLVRVVSTNYNQHAM
VFFKKVSQNREYFKITLYGRTKELTSELQENFIRFSKSLGLPENHIVFPVPIDQCIDG SEQ ID NO: 49: *G. gorilla* Scn
QDSTSDLIPAPPLSKVPLQQNFQDNQFQGKWYVVGLAGNAILREDKDPQKMYATIYELKE
DKSYNVTSVLFREKAQKCDYWIRTFVPGSQPGEFTLGNIKSYPGLTSYLVRVVSTNYNQH
AMVFFKKVSQNREYFKITLYGRTKELTSELKENFIRFSKSLGLPENHIVFPVPIDQCIDG SEQ ID NO: 50: *P. pygmaeus* Scn
QDSTSDLIPAPPLSKVPLQQNFQDNQFQGKWYVVGLAGNAIRREDKDSQKMYATIYELKE
DKSYNVTSVLFRKKKCDYWIRTFVPGSQPGEFTLGNTKGYPGLTSYLVRVVSTNYNQYA
MVFFKKVSQNREYFKITLYGRTKELTSELKENFIRFSKSLGLPENHIVFPAPIDQCIDG SEQ ID NO: 51: *M. mulatta* Scn
QDSSSDLIPAPPLSKVPLQQNFQDNQFQGKWYVVGLSGNAVGRKDEAPLKMYATIYELK
EDKSYNVTSILFRKEKCDYWIRTFVPGSQPGEFTLGNIQNHPGLTSYVVRVVSTNYKQYA
MVFFKKVSQNKEYFKITLYGRTKELTSELKENFIRFSKSLGLPENHIVFSVPIDQCING SEQ ID NO: 52: *C. jacchus* Scn
QDSPSPLIPAPPLSKVPLQQNFQDNQFQGKWYVVGLAGNAIRREDQDSLKMYATIYELKE
DKSYNVTSVLFRKGKCDYWIRTFVPSSRPGEFKLGNIESHPGLTSYIVRVVNTDYKQHAM
VFFMKASHNRKYFKVTLYGRTKELTSDLKENFTSFSKSLGLTENHIIFPVPIDQCIDG SEQ ID NO: 53: *O. princeps* Scn
QELTMDPTPSPRLIPVPSLRKIHVQKNFQSDQFQGKWYVVGLAGNNIHNSDQEHQQMYS
TTYELKEDGSYNVTSTLLRNQQCDHWIRTFVPGSKLGHFNLGNIKSYPTLKSYLIRVVTTD
YNQFAIVFFRKVYKNNKKFFKIVLYGRTKELSPELRGRFTSFAKTLGLTDNHIVFPAPIGQCI
DD

FIG. 29 (cont'd)

SEQ ID NO: 54: *O. cuniculus* Scn
QDPTPKLIPAPSLRRVPLQRNFQDEQFQGKWYVVGLAGNAVQKREEGQEPMYSTTYEL
NEDRSFNVTSTLLRDQRCDHWIRTFVPTSRPGQYNLGNIKSYPGVKNYIVRVVATDYSQ
YAMMFFRKGSRNKQFFKTTLYGRTKELSPELRERFTRFAKSLGLPDDRIVFPTPIDQCIDD SEQ ID NO: 55: *B. taurus* Scn
RSSSSRLLRAPPLSRIPLQPNFQADQFQGKWYTVGVAGNAIKKEEQDPLKMYSSNYELK
EDGSYNVTSILLKDDLCDYWIRTFVPSSQPGQFTLGNIKSYRGIRSYTVRVVNTDYNQFAI
VYFKKVQRKKTYFKITLYGRTKELTPEVRENFINFAKSLGLTDDHIVFTVPIDRCIDDQ SEQ ID NO: 56: *S. scrofa* Scn
QGTIPNWIPAPPLSKVPLQPNFQADQFQGKWYVVGLAGNAVKKEEQGRFKMYTTTYELK
EDGSYNVISTLLRGQLCDNWIRTFVPSLQPGQFKLGDIKKYSGLQSYVVRVVSTNYSQFA
IVFFKKVSNNQEYFKTTLYGRTKVLSPELKENFVRFAKSLGLSDDNIIFPVAIDQCIDGQ SEQ ID NO: 57: *T. truncatus* Scn
QDSTPNLIPAPPLFRVPLQPNFQPDQFQGKWYIVGLAGNAFKKEKQGQFKMYATTYELK
EDRSYNVTSALLRDERCDHWIRTFVPSSRPGQFTLGNIKGFPGVQSYTVRVATTNYNQF
AIVYFKKVYKNQEYFKTTLYGRTKELTPQLKENFIHFAKSLGLTDEYILFPVPIDKCIDDQ SEQ ID NO: 58 *E. caballus* Scn
RDPAPKLIPAPPLDRVPLQPDFKDDQFQGKWYVVGVAGNAFKKEEQGQFTMYTTTYELK
EDHSYNVTSILLRDQNCDHWIRTFIPSSQPGQFNLGDIKRYFGVQSYIVRVADTDYNQFAI
VFFRKVYKNQEYFKTTLYRRTKELTPELREKFISFAKSLGLTDDHIIFPVPIDQCIDEE SEQ ID NO: 59: *M. murinus* Scn
QDSKEKLIPAPPLLRVPLQPDFQDDQFQGKWYVVGLAGNAVSKEEQGQFTMYTTTYELK
DHSYNVTSTLLRNGKCDYWIRTFVLTSQPGQFALGNINRYPGIQSYTVRVVTNYNQFAI
VFFKKVSENKEYFKTTLYGRTKELPPELKENFIRFAKSLGLTEDHIIYPVPIDQCIDD SEQ ID NO: 60: *L. africana* Scn
QTHSPTLIPAPPLLRVPLQPDFQDDKFQGKWYVIGLAGNAVEKKEQGQFKMYTTTYELKE
DGSYNVTSTLLQEDGKCSYWIRTFVPSFQPGQFNLGNIKNFPGLQSYTVRVTATNYNQF
AIVFFKKVSKNGEYFKTTLYGRTKELTPELKERFIRFAKSLGLSDHIIFPVPIDRCIDDA SEQ ID NO: 61: *P. capensis* Scn
QEPTPLIPAPPLSSIPLKPNFHNDKFQGKWYVVGVAGNAITKEKDPSLMYTTTYELRDDG
SYNVTSTQFREKINCTHWTRTFVPTSQPGQFSLGNIDKYPHLSSYTVRVTATNYNYFAIV
YFKKVSKNQEYFKTTLYKRIKKLTHGLKKHFIQFAKSLGLPDNHITFLVPTDRCIDDA SEQ ID NO: 62: *C. familiaris* Scn
QDSTPSLIPAPPPLKVPLQPDFQHDQFQGKWYVIGIAGNILKKEGHGQLKMYTTTYELKD
DQSYNVTSTLLRNERCDYWNRDFVPSFQPGQFSLGDIQLYPGVQSYLVQVVATNYNQY
ALVYFRKVYKSQEYFKITLYGRTKELPLELKKEFIRFAKSIGLTEDHIIFPVPIDQCIDE

NKG2D DECOYS

CROSS-REFERENCE TO RELATED APPLICATIONS

This application is a U.S. National Phase Patent Application based on International Patent Application No. PCT/US2016/061368, which claims priority to U.S. Provisional Patent Application No. 62/253,590 filed Nov. 10, 2015, the entire contents each of which are incorporated by reference herein.

REFERENCE TO SEQUENCE LISTING

A computer readable text file, entitled "DN1SQ6253.txt (Sequence Listing.txt)" created on or about Nov. 8, 2016, with a file size of 89.4 KB, contains the Sequence Listing for this application and is hereby incorporated by reference in its entirety.

STATEMENT OF GOVERNMENT INTEREST

This invention was made with government support under grant CA174470 awarded by the National Institutes of Health. The government has certain rights in the invention.

FIELD OF THE DISCLOSURE

Single chain, multimerized, and/or glycosylated NKG2D decoys are described. The NKG2D decoys have high affinity and avidity for surface bound and soluble NKG2D ligands and can be used to (i) identify NKG2D ligands; (ii) treat cancer, graft vs. host disease (GVHD), and inflammatory conditions; and (iii) potentiate an immune response against a vaccine as well as many other potential uses.

BACKGROUND OF THE DISCLOSURE

NKG2D is a receptor found on the surface of many immune system cells, such as essentially all natural killer cells and CD8 T cells, subsets of CD4 T cells, and most gamma delta T cells. Ligand binding to the NKG2D receptor results in immune cell stimulation. While NKG2D-based stimulation of immune cells can be beneficial, it is also associated with numerous pathological conditions such as a number of inflammatory conditions. Moreover, activation of the immune system through NKG2D binding can dampen the effectiveness of vaccine administrations.

There are multiple molecules that serve as stimulating ligands for the NKG2D receptor. Most of these NKG2D ligands (NKG2DL) are not expressed or are expressed at low levels in normal cells. However, the expression of NKG2DL is upregulated in various pathological conditions. As one example, certain types of cancer cells express NKG2DL. Expression of NKG2DL also occurs in intestinal epithelial cells and under conditions of stress or infection.

Earlier studies targeted the NKG2D pathway as a potential cancer immunotherapy. These studies focused on monoclonal antibodies made against one particular NKG2DL, MICA. This work is described in, for example, WO 2008/036981. Briefly, it was observed that induction of high-titer antibodies against MICA in cancer patients elicited an anti-tumor response. As stated, however, there are numerous NKG2DL beyond MICA. Human ligands for NKG2D include MICA, MICB, and the RAET1/ULBP family (e.g., RAET1E/ULBP4, RAET1G/ULBP5, RAET1H/ULBP2, RAET1/ULBP1, RAET1L/ULBP6, and RAET1N/ULBP3).

Recognizing that it would be beneficial to target more than one NKG2DL, WO2010/080124 describes construction of a chimeric molecule comprising one NKG2D monomer (i.e., one half of a functional NKG2D homodimer binding domain) and an Fc portion for the treatment of cancer. WO2010/080124 explains that this NKG2D-Fc chimera can target any or all NKG2DL that are expressed on human tumor cells, and that they are thus capable of mediating tumor cell destruction through complement lysis and antibody-dependent cell-mediated cytotoxicity (ADCC). The described NKG2D-Fc chimera promotes efficient cross-presentation (e.g., priming) by dendritic cells, leading to the induction of potent T cell responses against the tumor. Moreover, WO2010/080124 states that this chimera is capable of binding and sequestering any "shed" (e.g., soluble or released) NKG2DL produced by tumor cells.

SUMMARY OF THE DISCLOSURE

While WO2010/080124 describes an interesting chimeric construct to more broadly neutralize a number of NKG2D ligands (NKG2DL), whether expressed on a tumor cell surface or shed, aspects of the chimeric construct detract from its ability to strongly bind and suppress the actions of NKG2DL. This is because, in part, NKG2D only binds its ligands with moderate affinities. Moreover, NKG2D must form a homodimer to effectively bind its ligands. Thus, at least two monomeric chimeric constructs of WO2010/080124 must be present to effectively bind a NKG2DL. While a sufficient number of chimeric constructs could potentially be administered at a local tumor site, the dosing required to achieve binding of shed ligands within the circulation (e.g., disseminated tumor cells, blood cancer cells) could be prohibitively high.

The present disclosure describes NKG2D decoys that include at least two NKG2D monomers within a construct so that each construct includes at least one functioning NKG2D homodimer. Thus, one construct can effectively bind and neutralize a NKG2DL whether cell bound or shed, even in the circulation. The NKG2D decoys can also have additional beneficial attributes that further enhance NKG2DL binding and sequestration. These further attributes include one or more of: expression as a single chain construct; multimerization to form avid decoys that tightly, and more competitively, bind NKG2DL; and/or glycosylation. Glycosylation can contribute to proper protein folding and facilitate protein-protein interactions.

The described NKG2D decoys can be used to (i) identify unknown or locate NKG2DL; (ii) treat cancer, graft vs. host disease (GVHD), and inflammatory conditions; and (iii) potentiate an immune response against a vaccine, as well as many other potential uses.

BRIEF DESCRIPTION OF THE FIGURES

Many of the drawings submitted herein are better understood in color, which is not available in patent application publications at the time of filing. Applicant considers the color versions of the drawings as part of the original submission and reserves the right to present color images of the drawings in later proceedings.

FIG. 2. Grouping of 47 epithelial ovarian cancer study cases based on NKG2D positivity, and summary of clinical parameters.

FIG. 3A, Box and whisker plots in graph depict % NKG2D$^+$ cancer cells in patients with (yes) and without (no) disease recurrence. Vertical lines in boxes represent quartiles. Whiskers extend to the furthest value within 1.5 times the inner quartile range. Each dot represents one patient's % NKG2D$^+$ value; the distribution along the Y-axis is randomized for visualization. Dots are colored by NKG2D$^+$ subgroup and those beyond the whiskers are considered outliers. The P value results from likelihood ratio test. FIG. 3B, Kaplan-Meier curve comparing progression-free survival of patients in the NKG2D Low (top line) and NKG2D High (bottom line) groups. The P value for the difference between NKG2D subgroups was determined by the log-rank test. FIG. 3C, Box and whisker plots depicting % NKG2D$^+$ cancer cells in patients grouped based on FIGO stage. The P value results from likelihood ratio test.

FIG. 4. Association between % NKG2D$^+$ cancer cells and disease recurrence.

FIG. 5. Clinical characteristics of epithelial ovarian cancer cases included in in vitro and xenotransplant assays.

FIG. 6. High plasticity marker expression among NKG2D$^+$ ovarian cancer.

FIG. 7A, Examples (EOC6, EOC7, and EOC8) of flow cytometry histogram pairs displaying ALDEFLUOR fluorescence profiles of non-hematopoietic (CD45-) NKG2D$^+$ or NKG2D$^-$ cancer cells. Open and filled grey profiles show ALDH1 activity in the absence and presence of the ALDH1 inhibitor DEAB, respectively. Numbers above bars represent % cells scoring high for ALDH1 activity. FIG. 7B, Flow cytometry dot plots depict gates and histograms below show corresponding NKG2D expression profiles of ALDEFLUOR$^{high}$ and ALDEFLUOR$^-$ cancer cells. Boxed gates in upper dot plots represent cells with high ALDH1 activity (at right), and cells certain to lack ALDH1 activity (at left). Dot plots of DEAB (+DEAB)-treated cell samples serve to set background ALDH1 activity. Open and filled grey histogram profiles display stainings for NKG2D and isotype Ig control, respectively. Numbers in histograms indicate mean fluorescence intensity ratios (MFIR). Data shown are representative of seven HGS EOC specimens (EOC6 through EOC12).

FIG. 8A, Phase contrast micrographs of tumor spheres formed by NKG2D$^+$ or NKG2D$^-$ cancer cells FACSAria-sorted from EOC16, EO17 and EO18 specimens. Cell numbers plated are indicated below each micrograph pair. FIG. 8B, Display of sphere (>100 μm) numbers formed by NKG2D$^+$ or NKG2D$^-$ cancer cells FACSAria-sorted from specimens EOC16 through EOC23, and plated at the indicated cell numbers. Due to specimen size limitations, not all cell concentrations could be plated per EOC sample (shaded fields). Serial numbers represent spheroids generated in serial passages. FIG. 8C, Flow cytometry dot plots showing NKG2D and NKG2DL expression on single cells dispersed from spheres formed by NKG2D$^+$ cancer cells. Vertical lines separate positive from negative NKG2D staining and are drawn based on isotype Ig background fluorescence. FIG. 8D, Bar graph displaying average numbers (from triplicate wells seeded with 5×10$^3$ cells) of spheres (>100 μm) formed by NKG2D$^+$ cancer cells left untreated (filled grey bars) or transduced with NKG2D RNAi (black bars) or control scrRNAi (hatched bars). Open bars represent average numbers of spheres formed by NKG2D$^-$ cancer cells. FIG. 8E, Bar graph showing average numbers (from triplicate wells seeded with 5×10$^3$ cells) of spheres formed by NKG2D$^+$ cancer cells in the presence of control isotype Ig (filled grey bars), anti-NKG2DL Abs (black bars), or anti-NKG2D Ab (hatched bars). Open bars represent average numbers of spheres formed by NKG2D$^-$ cancer cells. FIG. 8F, Display of xenograft tumor incidence as numbers of tumors developed per number of inoculations of 5×10$^3$ or 1×10$^4$ ex vivo FACSAria-sorted NKG2D$^+$ or NKG2D$^-$ cancer cells into NSG mice. Frequencies of tumor initiating cells were computed using ELDA. EOC34 and EOC35 represent HGS EOC cases, and EOC36 represents a Type I ovarian cancer. FIG. 8G, Flow cytometry dot plots of NKG2D and NKG2DL expression on single cells isolated from xenograft tumors derived from NKG2D$^+$ cancer cells. Vertical lines separate positive from negative NKG2D staining and are drawn based on isotype Ig background fluorescence.

FIGS. 9A-9C. Attributes of spheres and xenograft tumors derived from NKG2D$^+$ and NKG2D$^-$ EOC cells. FIG. 9A, Flow cytometry histogram at left: Absence of NKG2D on single cells dispersed from spheres derived from NKG2D$^-$ EOC24 cancer cells. Flow cytometry histogram at right: Presence of NKG2D on single cells dispersed from spheres derived from NKG2D$^+$ EOC24 cancer cells. Open and filled grey profiles show stainings for NKG2D and isotype Ig control, respectively. Data shown are representative of two specimens (EOC24 and EOC25; both HGS EOC). FIG. 9B, Display of sphere (>100 μm) numbers formed by NKG2D$^+$ or NKG2D$^-$ cancer cells FACSAria-sorted from four Type 1 EOC specimens and plated at the indicated cell numbers. Due to specimen size limitations, not all cell concentrations could be plated per EOC sample (shaded fields). FIG. 9C, Flow cytometry histograms showing absence of NKG2D (left) and presence of NKG2DL (right) on tumor cells isolated from a xenograft tumor derived NKG2D-EOC35 cancer cells. Open profiles represent NKG2D and NKG2DL staining, respectively; filled grey profiles represent isotype Ig background fluorescence. Data are representative of each two xenograft tumors derived from NKG2D$^-$ EOC34 and EOC35 cells.

FIGS. 10A-10D. NKG2D stimulates stem cell-like functional capacities in a transfected human tumor line. FIG. 10A, Phase contrast micrographs of tumor spheres formed by MDAH-2774-TF, parental MDAH-2774, and MDAH-2774-TF-KO cells, each plated at 1×10$^3$ cells/well.

FIG. 10B, Bar graph at left summarizes data as number of spheres (>100 μm) counted in three sets of triplicate wells seeded with MDAH-2774-TF, MDAH-2774, and MDAH-2774-TF-KO cells. Bar graph at right represents average numbers of spheres formed by MDAH-2774-TF cells plated in the presence of anti-NKG2DL Abs or isotype control Ig. Data from both graphs are representative of three independent experiments. FIG. 10C, Summary of tumor initiation capacities of MDAH-2774-TF, MDAH-2774, MDAH-2774 mock, and MDAH-2774-TF-KO cells implanted subcutaneously into flanks of NOD/SCID mice at the cell numbers indicated. Numbers in top horizontal line indicate weeks post tumor cell inoculation. Left vertical columns list mouse identification (ID) numbers. Dark and light grey boxes indicate presence and absence of measurable tumors, respectively. White fields indicate that animals were euthanized due to tumor size. FIG. 10D, Display summarizing xenograft tumor incidence expressed as numbers of tumors formed per numbers of inoculations of 1×10$^3$ or 1×10$^2$ MDAH-2774-TF cells into NOD/SCID mice treated with anti-NKG2DL Abs or control Ig, either locally at tumor cell inoculation site or via tail vein injection.

FIG. 12A, Ribbon representations of the crystal structures of the C4bbp heptamerization motif (left) and the NKG2D homodimeric ectodomain recognition unit (right). Disulfide bonds are shown as gray spheres. FIG. 12B, FIG. 12C, Schematic representations of the native NKG2D homodimer and the NKG2D$^{scd}_7$ protomer, detailing key features. FIG. 12D, Schematic representation of the overall molecular arrangement of the NKG2D$^{scd}_7$ multimer. FIG. 12E, Comparative reduced/non-reduced PAGE analysis confirming purity and disulfide bond formation. FIG. 12F, Analytical SEC showing solution monodispersivity of human NKG2D$^{scd}_7$ multimer.

FIGS. 13A, 13B. Sequence of the NKG2D$^{scd}_7$ construct of Example 2 with structural subunits, technical domains, and motifs separated by // in the provided order (SEQ ID NO: 78) and an exemplary sequence of human NKG2D (SEQ ID NO: 76).

FIG. 15A, Flow cytometry histogram profiles show binding of FITC-conjugated NKG2D$^{scd}_7$ to C1R, EL4 or MEL cells transfected with NKG2DL as indicated. Black and light grey profiles represent NKG2D$^{scd}_7$ binding and PBS control fluorescence, respectively. FIG. 15B, Flow cytometry dot plot display of cytotoxicity assays using the NKG2D$^+$ NKL effector cell line and fluorochrome-labeled transfected C1R-MICA (X-axis) and untransfected control C1R (Y-axis) target cells. Cytotoxicity is measured as live ratios of C1R to C1R-MICA cells. Dot plot at left displays target cell populations in the absence of effector NKL cells. Remainder dot plots show NKG2D-mediated cytotoxicity at an effector:target ratio of 1:1 in the presence of NKG2D$^{scd}_7$, anti-MICA Ab, or control isotype Ig. C1R to C1R-MICA ratios are noted in upper right quadrants.

FIGS. 16A-16D. Involvement of NKG2DL in cancer cell NKG2D-driven sphere formation and tumor initiation. FIG. 16A, Graphic display of average numbers (derived from triplicate wells seeded with 5×10$^3$ cells) of spheres (>100 μm) formed by NKG2D$^+$ HGS EOC cells in the presence (black bars) or absence (filled grey bars) of NKG2D$^{scd}_7$. Open bars represent average numbers of spheres formed by matching NKG2D$^-$ cancer cells. FIG. 16B, Bar graph showing average numbers (derived from triplicate wells seeded with 1×10$^3$ cells) of spheres (>100 μm) formed by MDAH-2774-TF cells in the presence or absence of NKG2D$^{scd}_7$. Data are representative of three independent experiments. FIG. 16C, Summary of xenograft tumor incidence expressed as numbers of tumors formed per number of inoculations of NKG2D$^+$ cancer cells into NSG mice, treated locally or systemically with NKG2D$^{scd}_7$ or control PBS. EOC40 and EOC41 represent HGS EOC; EOC42 represents Type I ovarian cancer. Numbers of cells injected were guided by specimen size. FIG. 16D, Summary of xenograft tumor incidence expressed as numbers of tumors formed per number of inoculations of ex vivo isolated unsorted cancer cells into NSG mice. EOC43-derived cells were transduced with NKG2D RNAi or control scrRNAi; mice inoculated with EOC44 or EOC45 cells received subcutaneous NKG2D$^{scd}_7$ or control PBS. EOC43 and EOC45 are HGS EOC; EOC44 represents a Type I ovarian cancer. C1R-MICA ratios are noted in upper right quadrants.

FIG. 17A, FIG. 17B, Experimental outline; Mice were bled before (day 0) and on day 3 and day 5 after LM infection. Shown is NKG2D and granzyme B expression on OT-I T cells. FIG. 17C, OT-1 BA-CTLs did not express NKp46 on any of these time-points. FIG. 17D, 1×10$^4$ OT-I T cells were adoptively transferred into B6 recipient mice followed by infection with LM-OVA. Shown is a section of the spleen with visible red (RP) and white pulp (WP) architecture on day 7 post-infection. FIG. 17E, OT-I memory cells were generated as outlined in FIG. 17A. OT-I memory cells are evenly distributed at the day 90 memory time-point. FIG. 17F, these mice were then challenged with wild-type LM and analyzed 48 hours later. OT-I T cells are clustered in the WP similarly to the day 7 antigen-specific response.

FIG. 18A, TCR signals are limited during bystander activation. Nur77-GFP mice were infected with 2000 cfu LM-OVA, or injected with aCD3 antibody or left untreated (control). Mice were euthanized for analysis on day 2 after infection and GFP expression level was determined. FIG. 18B, 18C, Data shown are from splenic CD8$^+$ T cells.

FIG. 19A, Mice were infected with 10$^7$ cfu actA$^-$ LM-OVA. Expression of Mult-1 and Rae-1 was determined 24 hours post infection on I-Ab$^+$ CD11c$^+$ cells. NKG2DL expression levels on I-Ab$^+$ CD11c$^+$ cells from infected mice are unshaded and from uninfected control mice are shaded in gray. FIG. 19B, RMA control cells were labeled with a low dose (0.2 μM) of Cell Trace Violet (CTV) and RMA-Rae1 expressing target cells were labeled with a higher dose of CTV (5 μM). The cells were mixed at a 1:1 ratio and incubated with OT-I BA-CTLs for 5 hours in vitro at an E:T ratio of 6:1. The CTV low to high ratio of the remaining live cells was determined by FACS analysis. Dead cells were excluded by propidium iodide staining. 1 μM SIINFEKL pulsed RMA cells served as a positive control group and an RMA+RMA group as a negative control group. FACS-purified OT-I BA-CTLs were isolated on day 3 after LM infection.

FIG. 20A, Mice were left untreated, injected with an NK-depleting antibody (PK136) and an NKG2D blocking antibody (HMG2D), or PK136 alone 2 days before and after an Infection with 2000 cfu LM-OVA. FIG. 20B, Bacterial load in the spleen was determined on day 5. The limit of detection (LOD) is 50 cfu per spleen. FIG. 20C, No difference in granzyme B and IFNγ expression by CD8 T cells on day 5 regardless of HMG2D administration.

FIGS. 21A-21C. The primary CDB T cell response is not affected by blocking αNKG2D antibody. Mice were injected with antibodies and infected with LM-OVA as described in FIG. 20. Mice received 10$^4$ naive OT-I T cells on the day of infection. (FIG. 21A) The size of the OT-I T cell population on day 5 is shown as a % of the total CD8 T cell pool. (FIG. 21B) The percentage of granzyme expressing OT-I T cells in the three experimental groups. (FIG. 21C) The bacteria/load in the spleen on day 5 post infection.

(FIG. 22A) It was first examined whether IL-12/15/18 treatment induces bystander-activation in human CD8 T cells. PBMCs were treated with IL-12/15/1L-18 (each at 100 ng/ml) for 24 hrs. CMV- and flu-specific T cells were identified by tetramer staining. Bystander-activation was determined by examining granzyme B expression. The size of the overall granzyme B inducible population is donor dependent and varies from ~10-40% (data not shown). (FIG. 22B) Flu- and CMV-specific T cells were sorted as in FIG. 22A and then used in a modified VITAL killing assay described in FIG. 19. Shown are data from 3 independent experiments. (FIG. 22C) Flu- and CMV-specific T cells were sorted as in FIG. 22A followed by single-cell RNAseq analysis using the C1 Fluidigm system.

(FIG. 23A) Mice were immunized with $10^6$ cfu of the attenuated ActA$^-$ strain of LM-OVA. One group of mice was treated with blocking αNKG2D antibody to prevent BA-CTL-mediated elimination of APCs. The endogenous (FIG. 23B) CD8 (to OVA) and (FIG. 23C) CD4 (to LLO) T cell response was measured on day 7 post immunization. (FIG. 23C) $5\times10^4$ CTV-labeled, naive OT-1 T cells were incubated with $1\times10^5$ CD11c$^+$ cells isolated from $10^6$ cfu actA$^-$ LM-OVA infected mice (40 hrs post-infection, black), or from uninfected B6 mice pulsed with (left peaks, pos. control) or without (right peaks, neg. control) OVA-peptide (FIG. 23D). CTV dilution was examined after in vitro co-culture for 50 hours. OT-I T cells incubated with DCs from the αNKG2D-treated group proliferated more extensively compared to OT-I T cells incubated with DCs from the control group suggesting that NKG2D treatment preserves OVA antigen-presenting cells.

(FIG. 25A) To show that NKG2D$^{scd}{}_7$ binds to its ligands the NKG2D$^-$ hepatmer was conjugated to FITC and RMA (left) and RMA-Rae1 (right) expressing cells were stained. (FIG. 25B) Using the same setup as in FIG. 20, NKG2D$^{scd}{}_7$ (H7, middle bar) treated mice (100 μg/mouse) have decreased pathogen clearance on day 4.5 following LM infection compared to untreated animals (no Tx, left bar) and similar to the anti-NKG2D treated animals (HMG2D, right bar).

FIG. 27. Treatment with NKG2D$^{scd}{}_7$ induces a significant increase in antigen-specific T cell responses following vaccination.

FIG. 28. VVT MICA Binding to Amine-Coupled NKG2D$^{scd}{}_7$. 240 RUs direct amine-coupled NKG2D$^{scd}{}_7$-Scn; blank immobilized CM5 as reference MICA VVT serial 2-fold dilutions 100 nM-0.78 nM, randomized, duplicates.

FIG. 29. Exemplary sequences of siderocalin orthologs (SEQ ID NOs: 45-62) useful for expression of NKG2D decoys.

DETAILED DESCRIPTION

Figure 1:
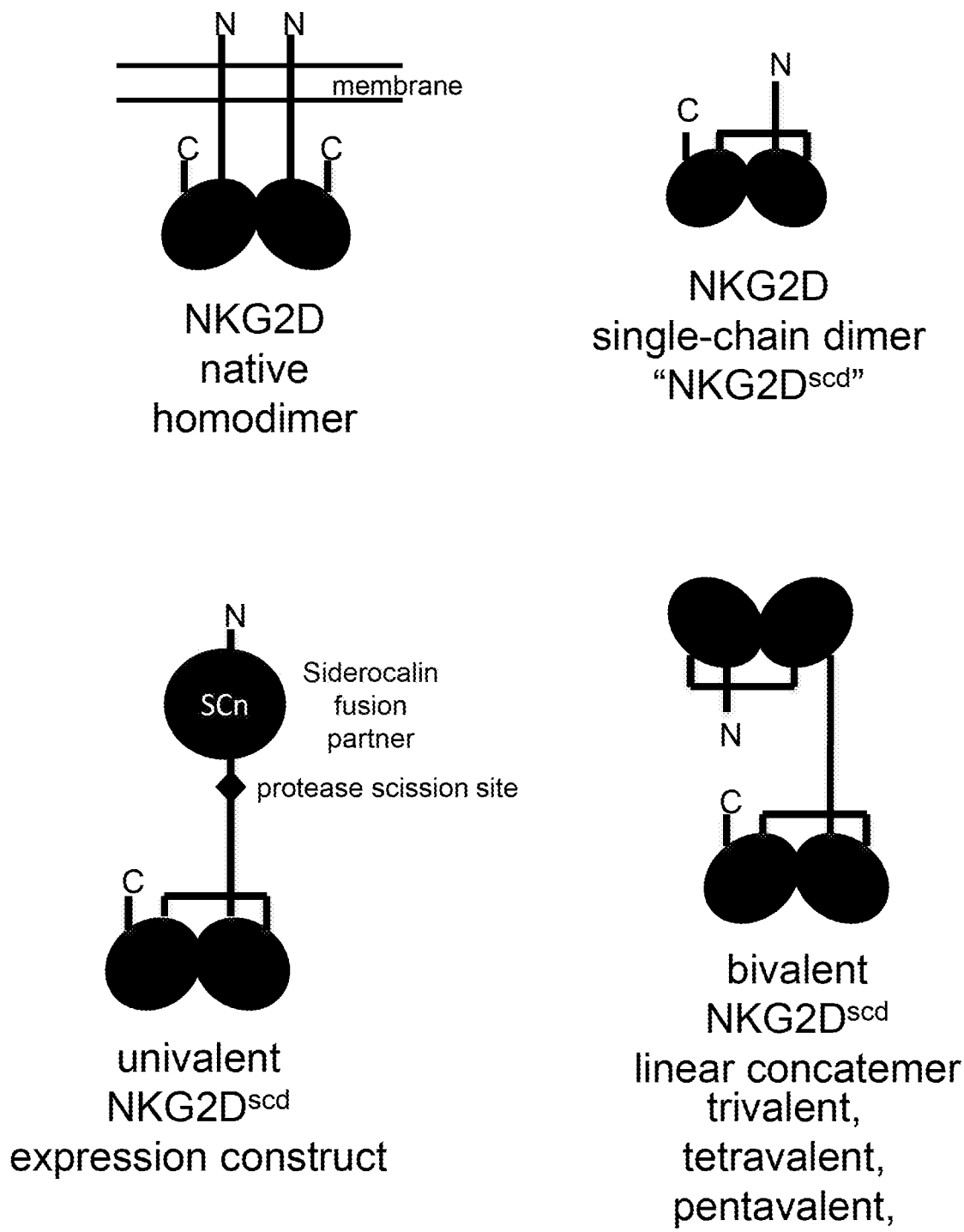
FIG. 1 shows native NKG2D and exemplary formats of NKG2D decoys disclosed herein.

NKG2D is an activating receptor found on the surface of many immune system cells, such as essentially all natural killer cells and CD8 T cells, subsets of CD4 T cells, and most gamma delta T cells. More particularly, NKG2D is a type II transmembrane glycoprotein having an extracellular lectin-like domain. This domain lacks the recognizable calcium-binding sites found in true C-type lectins and binds protein rather than carbohydrate ligands. NKG2D has also been referred to as KLRKI; killer cell lectin-like receptor subfamily K, member 1; CD314; KLR; NKG2-D; FLJ17759; FLJ75772 and D12S2489E.

NKG2D exists as a disulfide-linked homodimer that delivers an activating signal upon ligand binding. Signaling requires association with an adapter protein. Alternative splicing of NKG2D mRNA results in isoforms with different cytoplasmic domains that can associate either with DAP12 to deliver a true activating signal or with DAP10 resulting in a costimulatory signal. NKG2D has been implicated in immune surveillance and the immune response against viral infection. In addition, elevated levels of NKG2D ligands (NKG2DL) have been detected in proliferating cells and many types of cancer. Based on these observations, it has been suggested that expression levels of NKG2DL, MICA in particular, may provide useful information for the detection and/or diagnosis of cancer.

To that end, earlier studies targeting the NKG2D pathway with respect to potential cancer immunotherapy focused on monoclonal antibodies made against the NKG2DL, MICA. This work is described in WO 2008/036981, entitled "Methods for treating MICA-related disorders." Briefly, it was observed that induction of high-titer antibodies against MICA in cancer patients elicited an anti-tumor response.

There are numerous NKG2DL beyond MICA, however. Human ligands for NKG2D include the MIC family (MICA and MICB) and the RAET1/ULBP family. Members of the RAET1/ULBP family include: RAET1E/ULBP4, RAET1G/ULBP5, RAET1H/ULBP2, RAET1/ULBP1, RAET1L/ULBP6, and RAET1N/ULBP3. Mouse ligands for NKG2D include minor histocompatibility antigen 60 (H60) and retinoic acid early inducible transcript (RAE-I).

Recognizing the benefit of binding numerous NKG2DL, WO2010/080124 describes construction of a chimeric molecule including one NKG2D monomer (one half of an NKG2D homodimer binding domain) and an Fc portion for the treatment of cancer. WO2010/080124 explains that the NKG2D-Fc chimera can target any or all NKG2DL that are expressed on human tumor cells, and that they are thus capable of mediating tumor cell destruction through complement lysis and antibody-dependent cell-mediated cytotoxicity (ADCC). The described monomeric NKG2D-Fc chimera promotes efficient cross-presentation (e.g., priming) by dendritic cells, leading to the induction of potent T cell responses against the tumor. Moreover, WO2010/080124 states that this chimera is capable of binding and sequestering any "shed" (e.g., soluble or released) NKG2DL produced by tumor cells.

While WO2010/080124 describes an interesting chimeric construct to more broadly neutralize a number of NKG2DL, whether expressed on a tumor cell surface or shed, aspects of the chimeric construct, detract from its ability to strongly bind and suppress the actions of NKG2DL. This is because, in part, NKG2D only binds its ligands with moderate affinities. Moreover, NKG2D must form a homodimer to effectively bind its ligands. Thus, at least two chimeric constructs of WO2010/080124 must be present to effectively bind and sequester a NKG2DL. While a sufficient number of constructs could potentially be administered at a local tumor site, the dosing required to achieve binding of shed ligands within the circulation (e.g., disseminated tumor cells, blood cancer cells) could be prohibitively high.

The present disclosure describes NKG2D decoys that include at least two NKG2D monomers within a construct such that each construct includes a functioning NKG2D homodimer. Thus, one construct can effectively bind and neutralize a NKG2DL whether cell bound or shed, even into the circulation. The NKG2D decoys can also have beneficial attributes that further enhance NKG2DL binding and sequestration. These further attributes include one or more of: expression as a single chain construct; multimerization to form avid decoys that tightly, and more competitively, bind NKG2DL; and/or glycosylation. Glycosylation can contribute to proper protein folding and facilitate protein-protein interactions.

FIG. 1 depicts a native NKG2D homodimer as well as exemplary formats of NKG2D decoys disclosed herein. As shown, the NKG2D decoys can be provided as, for example, single chain linked dimers (NKG2D$^{scd}$), as bivalent, trivalent, tetravalent, pentavalent (etc.) concatemers; as part of fusion proteins (shown with a siderocalin fusion partner); and as heptavalent multimers, wherein each subunit contains a multimerization motif. Thus, NKG2D decoys can include a single chain including 2 NKG2D monomers that provide one NKG2D homodimeric binding domain (NKG2D homodimer); 4 NKG2D monomers that provide 2 NKG2D homodimers; 6 NKG2D monomers that provide 3 NKG2D homodimers; 8 NKG2D monomers that provide 4 NKG2D homodimers; 10 NKG2D monomers that provide 5 NKG2D homodimers; etc. The heptamerized form of the 2 NKG2D monomers single chain provides 14 NKG2D monomers capable of high affinity, high avidity binding of 7 NKG2DL. FIG. 12 provides additional detail for the heptameric form particularly. The heptameric NKG2D decoy forms from single chain constituents and folds under appropriate conditions. As will be understood by one of ordinary skill in the art, appropriate conditions include (i) physiological conditions (i.e., aqueous solutions of the right pH and salinity), and (ii) "oxidizing" in the sense of the surface of a cell, outside of a cell, or in the secretion pathway of a cell. A commonly used solution condition is "phosphate buffered saline", "PBS", which is a water-based salt solution including disodium hydrogen phosphate, sodium chloride and, in some formulations, potassium chloride and potassium dihydrogen phosphate. The pH can be buffered at 7.4. Oxidizing conditions are achieved by exposure to oxygen in the air, in the absence of specific added reducing agents, such as dithiothreitol. "Oxidizing" is important because the monomer includes disulfide bonds and the heptamer includes inter-chain disulfides which stabilize it. In general, the reducing conditions inside the cytoplasm and nucleus of a cell preclude disulfide formation.

As indicated, in particular embodiments, the NKG2D decoys have high affinity and avidity. High affinity means a dissociation constant, $K_D$, of $10^{-8}$ M or less, in particular embodiments from $10^{-8}$ M to $10^{-14}$ M, or in particular embodiments from $10^{-9}$ M to $10^{-12}$ M. In particular embodiments, high avidity means that a NKG2D decoy binds at least 2 NKG2DL, at least 3 NKG2DL, at least 4 NKG2DL, at least 5 NKG2DL, at least 6 NKG2DL, or at least 7 NKG2DL, at an overlapping time with high affinity. The NKG2DL bound at overlapping times can be the same NKG2DL or can be different NKG2DL.

In particular embodiments, the NKG2D decoys reduce or eliminate NKG2D access to NKG2DL in a physiologically relevant manner. In particular embodiments, such reductions can be demonstrated through in vitro assays wherein native NKG2D signaling is statistically significantly reduced or even prevented. One exemplary in vitro assay is an in vitro NK cell activation assay. Reductions or elimination can also be demonstrated through effective clinical treatments as described in detail elsewhere herein.

Aspects of the current disclosure are now described in more detail.

NKG2D Monomers. NKG2D decoys disclosed herein include at least two NKG2D monomers. The full length sequence of NKG2D has been described in the literature. See, for example, Accession: NP_031386 (SEQ ID NO: 76). Additionally, alternative splice variants of NKG2D have been described. Further relevant NKG2D sequences may be identified by searching databases of DNA or protein sequences, using commonly available search programs such as BLAST. Any NKG2D sequence or splice variant may be used so long as when constructed, the NKG2D decoy binds at least one NKG2DL with high affinity.

NKG2D monomers of the NKG2D decoys may also include partial sequences (i.e., a fragment) of the NKG2D receptor polypeptide, provided that the resulting polypeptide, when constructed as a NKG2D decoy, retains the ability to bind at least one NKG2DL with high affinity. For example, NKG2D monomers of the NKG2D decoys can be shortened at either end of the NKG2D sequence by one or more amino acid residues. More specifically, the N-terminus of the NKG2D sequence can be truncated by 1, 2, 3, 4, 5, 6, 7, 8, 9, 10, 11, 12, 13, 14, 15, 16, 17, 18, 19, 20, 30, 40, 50, 60, 70, 80 or more residues, including all integers in between 1-80. Similarly, the C-terminus of the NKG2D sequence can be truncated by 1, 2, 3, 4, 5, 6, 7, 8, 9, 10, 11, 12, 13, 14, 15, 16, 17, 18, 19, 20, 30, 40, 50, 60, 70, 80 or more residues, including all integers in between 1-80. In particular embodiments, both the N-terminus and the C-terminus may be truncated.

In particular embodiments, all or part of the intracellular portion of NKG2D can be deleted. For example, the NKG2D monomers can include predominantly or completely the extracellular fragment of the NKG2D receptor. Structural analyses have revealed that amino acid residues 78 to 216 (or 150-207) of the human NKG2D sequence correspond to the extracellular portion of the NKG2D, containing ligand-binding sites. For a murine counterpart, the extracellular domain is amino acid residues 78-232, 94-232, 92-232, or 166-223. Accordingly, in particular embodiments, the NKG2D monomers include the corresponding portion of the NKG2D sequence, e.g., amino acid residues 78-216 (or 150-207) of human NKG2D; and/or 78-232, 94-232, 92-232, and/or 166-223 of murine NKG2D.

In particular embodiments, NKG2D monomers can include one or more mutations, for example, at the interface of NKG2D-ligand binding. For comprehensive information regarding the amino acid residues that are involved in receptor-ligand contact, see, for example, Strong & McFarland, 2004, Advances in Protein Chemistry, 68: 281-213; Li et al., May 2001, Nature Immunology, 2(5): 443-451; McFarland & Strong, December 2003, Immunity, 19: 803-812; and MacFarland et al., April 2003, Structure, 11: 411-422. For additional information regarding NKG2D binding to MICA particularly, see, for example, Lengyel et al., 2007, J. Biol. Chem., 282: 30658-666. As particular examples, residues of human NKG2D important for binding to MICA include Y152, Q185, K197, Y199, E201 and N207.

Residues of human NKG2D important for binding to ULBP3 include Y199 and Y152. Residues of murine NKG2D important for binding to RAE-13 include K166, Y168, Y215, K213, E217 and N223. In particular embodiments, therefore, most or all of these residues can be maintained without a mutation or deletion at the position where broad permissibility (e.g., specificity) for multiple NKG2DL is desirable. However, it is also possible to design NKG2D monomers that preferentially bind one ligand over another ligand by strategically introducing a mutation at one or more of these key residues that confer selective ligand-recognition and binding. On the other hand, certain amino acid residues are involved in the binding of various ligands. For example, Y152 and Y199 in human NKG2D, which are equivalent to Y168 and Y215 respectively in the murine counterpart, contribute to the binding of MICA as well as ULBP3. Therefore, in particular embodiments, these residues are unmodified so as to retain broad ligand specificity.

Based on these resources, among others, one of ordinary skill in the art can determine the amino acid residues of NKG2D that contribute to the interaction with a ligand and test the effect of mutations by systematically altering the key residues. In any of the embodiments, the resulting NKG2D monomers are capable of binding an NKG2DL with high affinity when in homodimeric form within a decoy disclosed herein.

Exemplary methods for assaying homodimer/NKG2DL binding include ELISA, surface plasmon resonance analysis, CD analysis, fluorescence quenching, size-exclusion binding assay and isothermal titration calorimetry. For brief descriptions of these assays, see, for example, Lengyel et al. (2007).

Particular embodiments can utilize an exemplary human NKG2D: MGWIRGRRSRHSWEMSEFHNYNLDLKKSDFSTRWQKQRCPWKSKCRENASPFFFC CFIAVAMGIRFIIMVAIWSAVFLNSLFNQEVQIPLTESYCGPCPKNWICYKNNCYQFFDE SKNVVYESQASCMSQNASLLKVYSKEDQDLLKLVKSYHVVMGLVHIPTNGSWQWEDGS ILSPNLLTIIEMQKGDCALYASSFKGYIENCSTPNTYICMQRTV (SEQ ID NO: 1) as a NKG2D monomer or an extracellular fragment thereof. Additional examples of human NKG2D monomers include SEQ ID NO: 76 (FIG. 13B) or an extracellular fragment thereof.

Particular examples of human NKG2D monomers also include:

(SEQ ID NO: 65)
NQEVQIPLTESYCGPCPKNWICYKNNCYQFFDESKNWYESQASCMSQNAS
LLKVYSKEDQDLLKLVKSYHVVMGLVHIPTNGSWQWEDGSILSPNLLTII
EMQKGDCALYASSFKGYIENCSTPNTYICMQRTV;

(SEQ ID NO: 66)
QIPLTESYCGPCPKNWICYKNNCYQFFDESKNWYESQASCMSQNASLLKV
YSKEDQDLLKLVKSYHWMGLVHIPTNGSWQWEDGSILSPNLLTIIEMQKG
DCALYASSFKGYIENCSTPNTYICMQRTV;
and (SEQ ID NO: 79)
SYCGPCPKNWICYKNNCYQFFDESKNWYESQASCMSQNASLLKVYSKEDQ
DLLKLVKSYHWMGLVHIPTNGSWQWEDGSILSPNLLTIIEMQKGDCALYA
SSFKGYIENCSTPNTYICMQRTV.

Particular embodiments can utilize an exemplary murine NKG2D: MSKCHNYDLKPAKWDTSQEQQKQRLALTTSQPGENGIIRGRYPIEKLKISPMFVVRVLAIALAIRFTLNTLMWLAIFKETFQPVLCNKEVPVSSREGYCGPCPNNWICHRNNCYQFFNEEKTWNQSQ ASCLSQNSSLLKIYSKEEQDFLKLVKSYHWMGLVQIPANGSWQWEDGSSLSYNQLTLVEIPKG SCAVYGSSFKAYTEDCANLNTYICMKRAV (SEQ ID NO: 2) or an extracellular fragment thereof as a NKG2D monomer.

Particular examples of murine NKG2D monomers also include:

(SEQ ID NO: 71)
NKEVPVSSREGYCGPCPNNWICHRNNCYQFFNEEKTWNQSQASCLSQNSS
LLKIYSKEEQDFLKLVKSYHVVMGLVQIPANGSWQWEDGSSLSYNQLTLV
EIPKGSCAVYGSSFKAYTEDCANLNTYICMKRAV;
and (SEQ ID NO: 72)
PVSSREGYCGPCPNNWICHRNNCYQFFNEEKTWNQSQASCLSQNSSLLKI
YSKEEQDFLKLVKSYHWMGLVQIPANGSWQWEDGSSLSYNQLTLVEIPKG
SCAVYGSSFKAYTEDCANLNTYICMKRAV.

Single Chains. Particular embodiments of NKG2D decoys use a single-chain including two NKG2D monomers that form a functioning NKG2D homodimer (NKG2D$^{scd}$). Expression of a NKG2D$^{scd}$ decoy can increase the efficiency of protein production and/or can enhance physiologic activity. Protein production efficiency can be improved by expressing the decoy as a NKG2D$^{scd}$ because protein folding is stabilized by intramolecular interactions, and therefore the intramolecular interactions between the two NKG2D monomers (particularly the disulfide bonds promote folding). Furthermore, the physiologic activity of the NKG2D decoys can be enhanced through use of a NKG2D$^{scd}$ because the NKG2D monomers are in the constitutively active (dimer binding domain) form. The NKG2D$^{scd}$ form also dramatically simplifies using the active, homodimeric NKG2D binding domain in engineered protein-based research reagents, and biologic clinical diagnostics and therapeutics, by eliminating the need for two separate polypeptide chain constructs, each encoding an NKG2D monomer, to generate a full NKG2D homodimer binding domain. The NKG2D$^{scd}$ form of NKG2D decoys can also have affinity for ligands improved by joining protomers together which may then be mutated symmetrically or asymmetrically.

Particular embodiments can utilize at least two NKG2D monomers provided above to form a NKG2D$^{scd}$. An exemplary human NKG2D$^{scd}$ includes: NQEVQIPLTESYCGPCP KNWICYKNNCYQFFDESKNWYESQASCMSQNASLLKVYSKEDQDLLKLVKSYHWMGLVHIPT NGSWQWEDGSILSPNLLTIIEMQKGDCALYASSFKGYIENCSTPNTYICMQRTVQIPLTESYCG PCPKNWICYKNNCYQFFDESKNWYESQASCMSQNASLLKVYSKEDQDLLKLVKSYHMGLV HIPTNGSWQWEDGSILSPNLLTIIEMQKGDCALYASSFKGYIENCSTPNTYICMQRTV (SEQ ID NO: 3).

An exemplary murine NKG2D$^{scd}$ includes: NKEVPVSSREGYCGPC PNNWICHRNNCYQFFNEEKTWNQSQASCLSQNSSLLKIYSKEEQDFLKLVKSYHWMGLVQIPA NGSWQWEDGSSLSYNQLTLVEIPKGSCAVYGSSFKAYTEDCANLNTYICMKRAVPVSSREGY CGPCPNN- WICHRNNCYQFFNEEKTWNQSQASCLSQNSSLLKI-
YSKEEQDFLKLVKSYHWMGL
VQIPANGSWQWEDGSSLSYNQLTLVEIPKGSCA-
VYGSSFKAYTEDCANLNTYICMKRAV (SEQ ID NO: 4).

Multimerization. Particular embodiments include a multimeric form of the NKG2D decoy. The NKG2D decoy include NKG2D monomers multimerized by linear concatenation, by ferritin-based multimerization, by coiled-coil multimerization, etc. For example, particular embodiments can utilize an exemplary human bivalent NKG2D$^{scd}$ linear concatemer:

(SEQ ID NO: 5)
NQEVQIPLTESYCGPCPKNWICYKNNCYQFFDESKNWYESQASCMSQNAS

LLKVYSKEDQDLLKLVKSYHWMGLVHIPTNGSWQWEDGSILSPNLLTIIE

MQKGDCALYASSFKGYIENCSTPNTYICMQRTVQIPLTESYCGPCPKNWI

CYKNNCYQFFDESKNWYESQASCMSQNASLLKVYSKEDQDLLKLVKSYHW

MGLVHIPTNGSWQWEDGSILSPNLLTIIEMQKGDCALYASSFKGYIENCS

TPNTYICMQRTVNQEVQIPLTESYCGPCPKNWICYKNNCYQFFDESKNWY

ESQASCMSQNASLLKVYSKEDQDLLKLVKSYHWMGLVHIPTNGSWQWEDG

SILSPNLLTIIEMQKGDCALYASSFKGYIENCSTPNTYICMQRTVQIPLT

ESYCGPCPKNWICYKNNCYQFFDESKNWYESQASCMSQNASLLKVYSKED

QDLLKLVKSYHWMGLVHIPTNGSWQWEDGSILSPNLLTIIEMQKGDCALY

ASSFKGYIENCSTPNTYICMQRTV.

Particular embodiments can utilize an exemplary murine bivalent NKG2D$^{scd}$ linear concatemer: NKEVPVSSREGY-CGPCPNNWICHRNNCYQFFNEEKTWNQSQAS-CLSQNSSLLKI YSKEEQDFLKLVKSYHWWMGLVQI-PANGSWQWEDGSSLSYNQLTLVEIPKGSCAVYGSS-FKAY TEDCANLNTYICMKRAVPVSSREGYCGPCPNN-WICHRNNCYQFFNEEKTWNQSQASCLSQN SSLLKI-YSKEEQDFLKLVKSYHWMGLVQIPANG-SWQWEDGSSLSYNQLTLVEIPKGSCAVYGS SFKAYTEDCANLNTYICMKRAVNKEVPVSSREGY-CGPCPNNWICHRNNCYQFFNEEKTWNQS QAS-CLSQNSSLLKIYSKEEQDFLKLVKSYHWMGLVQI-PANGSWQWEDGSSLSYNQLTLVEIPK GSCAVYGSSFKAYTEDCANLNTYICMKRAVPVSSR-EGYCGPCPNNWICHRNNCYQFFNEEKT WNQSQAS-CLSQNSSLLKIYSKEEQDFLKLVKSYHWMGLVQI-PANGSWQWEDGSSLSYNQLTL VEIPKGSCAVYGSSFKAYTEDCANLNTYICMKRAV (SEQ ID NO: 6).

As indicated, linear concatemers include repeating functional units.

In particular embodiments, C4b multimerization domains are used. C4 binding protein (C4b) is the major inhibitor of the classical complement and lectin pathway. The complement system is a major part of innate immunity and is the first line of defense against invading microorganisms. Orchestrated by more than 60 proteins, its major task is to discriminate between host cells and pathogens and to initiate immune responses when necessary. It also recognizes necrotic or apoptotic cells. Hofmeyer et al., *J. Mol. Biol.* 2013 Apr. 26; 425(8):1302-17.

Full-length native C4b includes seven α-chains linked together by a multimerization (i.e., heptamerization) domain at the C-terminus of the α-chains. Blom et al., (2004) *Mol. Immunol.* 40: 1333-1346. One of the α-chains can be replaced by a β-chain in humans. The wild-type C4b multimerization domain is 57 amino acid residues in humans and 54 amino acid residues in mice. Forbes et al., *PLoS One.* 2012; 7(9): e44943. It contains an amphipathic α-helix region, which is necessary and sufficient for heptamerization, as well as two cysteine residues which stabilize the structure. Kask et al., (2002) *Biochemistry* 41: 9349-9357.

The sequences of a number of C4b domain proteins are available in the art. These include human C4b multimerization domains as well as a number of homologues of human C4b multimerization domain available in the art. There are two types of homologues: orthologues and paralogues. Orthologues are defined as homologous genes in different organisms, i.e. the genes share a common ancestor coincident with the speciation event that generated them. Paralogues are defined as homologous genes in the same organism derived from a gene, chromosome or genome duplication, i.e. the common ancestor of the genes occurred since the last speciation event.

GenBank indicates mammalian C4b multimerization domain homologues in species including chimpanzees, rhesus monkeys, rabbits, rats, dogs, horses, mice, guinea pigs, pigs, chicken, and cattle. Further C4b multimerization domains may be identified by searching databases of DNA or protein sequences, using commonly available search programs such as BLAST.

Particular C4b multimerization domains that can be used include:

| SEQ ID NO. | Sequence |
|---|---|
| 7 | RSAGAHAGWETPEGCEQVLTGKRLMQCLPNPEDVKMALEVYKLSLEIEQLELQRDSARQSTLDKEL |
| 8 | SGRAHAGWETPEGCEQVLTGKRLMQCLPNPEDVKMALEVYKLSLEIEQLELQRDSARQSTLDKELVPR |
| 9 | KKQGDADVCGEVAYIQSVVSDCHVPTAELRTLLEIRKLFLEIQKLKVELQGLSKE |
| 10 | ETPEGCEQVLTGKRLMQCLPNPEDVKMALEVYKLSLEIEQLELQRDSARQSTLDKEL |
| 11 | WETPEGCEQVLTGKRLMQCLPNPEDVKMALEVYKLSLEIEQLELQRDSARQSTLDKEL |
| 12 | CEQVLTGKRLMQCLPNPEDVKMALEVYKLSLEIEQLELQRDSARQSTLDKEL |
| 13 | ETPEGCEQVLTGKRLMQCLPNPEDVKMALEVYKLSLEIEQLELQRDSARQYTLDKEL |

-continued

| SEQ ID NO. | Sequence |
|---|---|
| 14 | ETPEGCEQVLAGKRLMQCLPNPEDVKMALEVYKLSLEIEQLELQRDRARQSTLDK EL |
| 15 | ETPEGCEQVLAGKRLMQCLPNPEDVKMALEVYKLSLEIEQLELQRDRARQSTWDK EL |
| 16 | EVPEGCEQVQAGRRLMQCLADPYEVKMALEVYKLSLEIELLELQRDKARKSSVLR QL |
| 17 | VVPEGCEHILKGRKTMQCLPNPEDVKMALEIYKLSLDIELLELQRDRAKESTVQSPV |
| 18 | EVPKDCEHVFAGKKLMQCLPNSNDVKMALEVYKLTLEIKQLQLQIDKAKHVDREL |
| 19 | EYPEDCEQVHEGKKLMQCLPNLEEIKLALELYKLSLETKLLELQIDKEKKAKAKYSI |
| 20 | EYPEDCEQVHEGKKLMECLPTLEEIKLALALYKLSLETNLLELQIDKEKKAKAKYST |
| 21 | EIAEGCEQVLAGRKIMQCLPKPEDVRTALELYKLSLEIKQLEKKLEKEEKCTPEVQE |
| 22 | EYPEGCEQVVTGRKLLQCLSRPEEVKLALEVYKLSLEIEILQTNKLKKEAFLLREREK NVTCDFNPE |
| 23 | EYPEGCEQVVTGRKLLKCLSRPEEVKLALEVYKLSLEIALLELQIDKPKDAS |
| 24 | EVPENCEQVIVGKKLMKCLSNPDEAQMALQLYKLSLEAELLRLQIVKARQGS |
| 25 | EASEDLKPALTGNKTMQYVPNSHDVKMALEIYKLTLEVELLQLQIQKEKHTEAH |
| 26 | VSAEVCEAVFKGQKLLKCLPNAMEVKMALEVYKLSLEIEKLEQEKRKLEIA |
| 27 | EVPEECKQVAAGRKLLECLPNPSDVKMALEVYKLSLEIEQLEKEKYVKIQEKFSKKE MKQLTSALH |
| 28 | EVLEDCRIVSRGAQLLHCLSSPEDVHRALKVYKLFLEIERLEHQKEKWIQLHRKPQS MK |
| 29 | EGPEDCEIVNKGRQLLQCLSSPEDVQRALEVYKLSLEIERLEQQREKRTSVHRKAH YTKVDGP |
| 30 | EAPEGCEQVLTGRKLMQCLPSPEDVKVALEVYKLSLEIKQLEKERDKLMNTHQKFS EKEEMKDLFFP |
| 31 | EVPEGCEQVLTGKKLMQCLPNPEDVKMALEVYKLSLEIELLELQIDKARQGS |
| 32 | GCEQVLTGKRLMQCLPNPEDVKMALEVYKLSLEIEQLELQRDSARQS |
| 33 | ETPEGCEQVLTGKRLMQCLPNPEDVKMALEVYKLSLEIEQLELQRDSARQS |
| 34 | GSEQVLTGKRLMQSLPNPEDVKMALEVYKLSLEIEQLELQRDSARQSTLDKEL |
| 35 | ETPEGCEQVLTGKRLMQCLPNPEDVKMALEIYKLTLEIEQLELQRDSARQSTLDKE L |
| 36 | ETPEGCEQVLTGKRLMQCLPNPEDVKMALEIYKLSLEIKQLELQRDSARQSTLDKE L |
| 37 | EGCEQILTGKRLMQCLPDPEDVKMALEIYKLSLEIKQLELQRDRARQSTL |
| 38 | ETPEGCEQVLTGKRLMQCLPNPEDVKMALEVYKLSLEIKQLELQRDRARQSTLDKE L |
| 39 | EGCEQILTGKRLMQCLPNPEDVKMALEIYKLSLEIEQLELQRDRARQSTLDK |

In particular embodiments, the C4b multimerization domain will be a multimerization domain which includes (i) G at position 12, (ii) A at position 28, (iii) L at positions 29, 34, 36, and/or 41; (iv) Y at position 32; (v) K at position 33; and/or (vi) C at positions 6 and 18. In particular embodiments, the C4b multimerization domain will be a multimerization domain which includes (i) G at position 12, (ii) A at position 28, (iii) L at positions 29, 34, 36, and 41; (iv) Y at position 32; (v) K at position 33; and (vi) C at positions 6 and 18.

C4b multimerization domains can include any of SEQ ID NOs. 7-39 with an N-terminal deletion of at least 1 consecutive amino acid residues (eg. at least 2, 3, 4, 5, 6, 7, 8, 9, 10 consecutive amino acid residues) in length. Additional embodiments can include a C-terminal deletion of at least 1 consecutive amino acid residues (eg. at least 2, 3, 4, 5, 6, 7, 8, 9, 10 consecutive amino acid residues) in length.

Particular C4b multimerization domain embodiments will retain or will be modified to include at least 1 of the following residues: A6; E11; A13; D21; C22; P25; A27;

E28; L29; R30; T31; L32; L33; E34; I35; K37; L38; L40; E41; I42; Q43; K44; L45; E48; L49; or Q50. Further embodiments will retain or will be modified to include A6; E11; A13; D21; C22; P25; A27; E28; L29; R30; T31; L32; L33; E34; I35; K37; L38; L40; E41; I42; Q43; K44; L45; E48; L49; and Q50. Particular C4b multimerization domain embodiments will include the amino acid sequence "AELR". For additional information regarding C4b multimerization, see WO/91/11461.

Particular embodiments can utilize an exemplary multimerization domain linked to an exemplary human NKG2D$^{scd}$. For example, particular embodiments include the multimerization domain: (SEQ ID NO: 7) linked to the human NKG2D: (SEQ ID NO: 1 or 76) or the murine NKG2D (SEQ ID NO: 2) Particular embodiments include the multimerization domain: (SEQ ID NO: 7) linked to the human NKG2D$^{scd}$: (SEQ ID NO: 3) or linked to SEQ ID NO: 5. Particular embodiments include the multimerization domain: (SEQ ID NO: 7) linked to the murine NKG2D$^{scd}$: (SEQ ID NO: 4) or linked to SEQ ID NO: 6. SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 and/or 39 can also be linked to SEQ ID NO: 1, 2, 3, 4, 5, 6, or 76.

As will be understood by one of ordinary skill in the art, all sequences disclosed herein and all combinations of resulting NKG2D decoys can additionally include additional amino acid sequences to include further beneficial attributes. For example, sequences disclosed herein can include tag peptides which in particular embodiments can provide an epitope to which an anti-tag antibody can selectively bind. The epitope tag generally can be placed at the amino- or carboxyl-terminus of the NKG2D decoy. However, in particular embodiments, an epitope tag can be placed within the amino acid sequence of a NKG2D decoy. In particular embodiments, an epitope tag can be used as a linker to join a NKG2D domain to a second NKG2D domain and/or to a multimerization domain or another peptide or another type of molecule. In particular embodiments a linker can be GSSGSSG (SEQ ID NO: 40). The presence of such epitope-tagged forms of NKG2D decoys can be detected using an antibody against the epitope tag. Also, provision of the epitope tag enables the NKG2D decoy to be readily purified by affinity purification using an anti-tag antibody or another type of affinity matrix that binds to the epitope tag; this also can be useful for binding the NKG2D decoy to a support for heterogeneous screening methods. Various tag polypeptides and their respective antibodies are well known in the art. Examples include a flag tag (e.g., DYKDE (SEQ ID NO: 41); poly-histidine tags (e.g., HHHHHH (SEQ ID NO: 42)) or poly-histidine-glycine tags (e.g., GSHHHHHH (SEQ ID NO: 43); GTKHHHHHH (SEQ ID NO: 44)); the flu HA tag polypeptide and its antibody 12CA5 (Field et al., *Mol. Cell. Biol.*, 8:2159-2165 (1988)); the c-myc tag and the 8F9, 3C7, 6E10, G4, B7 and 9E10 antibodies thereto (Evan et al., *Molecular and Cellular Biology*, 5:3610-3616 (1985)); and the Herpes Simplex virus glycoprotein D (gD) tag and its antibody (Paborsky et al., *Protein Engineering*, 3(6):547-553 (1990)). Other tag polypeptides include the KT3 epitope peptide (Martin et al., *Science*, 255:192-194 (1992)); tubulin epitope peptide (Skinner et al., *J. Biol. Chem.*, 266:15163-15166 (1991)); and the T7 gene 10 protein peptide tag (Lutz-Freyermuth et al., *Proc. Natl. Acad. Sci. USA*, 87:6393-6397 (1990)).

In particular embodiments, the NKG2D decoy includes an intervening linker between an NKG2D monomer, a second NKG2D monomer and/or a multimerization domain (e.g., C4b multimerization domain). In general, the amino acids within the linker sequences are not deleterious to the biological function (e.g., NKG2DL binding affinity) of the NKG2D decoy, and may even be beneficial to biological function. Alternatively, a NKG2D decoy can lack linker sequences, but for the linker sequence between NKG2D monomers. Particular embodiments can include flexible linkers described elsewhere herein and/or Gly-Ser linkers (e.g., GGS). In particular embodiments, rigid linker sequences, such as proline-rich sequences may also be used.

NKG2D decoys may additionally include additional domains such as additional antigen or antigenic fragment (e.g., 2, 3, 4, 6, 8, 10 additional antigens or antigenic fragments).

"Variants" include protein sequences having one or more amino acid additions, deletions, stop positions, or substitutions, as compared to a protein sequence disclosed elsewhere herein.

An amino acid substitution can be a conservative or a non-conservative substitution. Variants of protein sequence disclosed herein can include those having one or more conservative amino acid substitutions. A "conservative substitution" or "conservative amino acid substitution" involves a substitution found in one of the following conservative substitutions groups: Group 1: A, G, S, T; Group 2: D, E; Group 3: N, Q; Group 4: R, K, H; Group 5: I, L, M, V; and Group 6: F, Y, W.

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the alpha-helical or beta-sheet structure); the charge or hydrophobicity of the molecule at the target site; or the bulk of the side chain. Non-conservative substitutions which in general are expected to produce the greatest changes in the protein's properties are those in which (i) a hydrophilic residue (e.g. S or T) can be substituted for (or by) a hydrophobic residue (e.g. L, I, F, V, or A); (ii) a C or P can be substituted for (or by) any other residue; (iii) a residue having an electropositive side chain (e.g. K, R, or H) can be substituted for (or by) an electronegative residue (e.g. Q or D); or (iv) a residue having a bulky side chain (e.g. F), can be substituted for (or by) one not having a bulky side chain, (e.g. G). Additional information is found in Creighton (1984) Proteins, W.H. Freeman and Company.

Variants of protein sequences disclosed herein also include proteins with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a protein sequence disclosed herein.

Variants of proteins disclosed herein include proteins that share: 70% sequence identity with any of SEQ ID NO: 1-79; 75% sequence identity with any of SEQ ID NO: 1-79; 80% sequence identity with any of SEQ ID NO: 1-79; 81% sequence identity with any of SEQ ID NO: 1-79; 82% sequence identity with any of 1-79; 83% sequence identity with any of SEQ ID NO: 1-79; 84% sequence identity with any of SEQ ID NO: 1-79; 85% sequence identity with any of SEQ ID NO: 1-79; 86% sequence identity with any of SEQ ID NO: 1-79; 87% sequence identity with any of SEQ ID NO: 1-79; 88% sequence identity with any of SEQ ID NO: 1-79; 89% sequence identity with any of SEQ ID NO: 1-79; 90% sequence identity with any of SEQ ID NO: 1-79; 91% sequence identity with any of SEQ ID NO: 1-79; 92% sequence identity with any of SEQ ID NO: 1-79; 93% sequence identity with any of SEQ ID NO: 1-79; 94% sequence identity with any of SEQ ID NO: 1-79; 95% sequence identity with any of SEQ ID NO: 1-79; 96% sequence identity with any of SEQ ID NO: 1-79; 97% sequence identity with any of SEQ ID NO: 1-79; 98% sequence identity with any of SEQ ID NO: 1-79; or 99% sequence identity with any of SEQ ID NO: 1-79.

"Percent (%) amino acid sequence identity" with respect to the sequences identified herein is defined as the percentage of amino acid residues in a candidate sequence that are identical with the amino acid residues in the reference sequence for each of the NKG2D monomer(s), the multimerization domain (e.g., C4b), a non-NKG2D fusion partner, etc., and/or the complete fusion after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program (Altschul et al., Methods in Enzymology, 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix BLOSUM62.

Variants will typically exhibit the same qualitative biological activity and elicit a substantially similar biological response as a reference peptide, although variants can be selected to modify the characteristics of a reference peptide as needed. Screening of variants can be performed using assays of NK cell activities, as known in the art. In particular embodiments, there is no statistically-significant difference in a biological effect in an in vitro NK cell activation assay between a variant peptide and a reference peptide.

Covalent modifications of NKG2D decoys are included within the scope of the disclosure. One type of covalent modification includes reacting targeted amino acid residues of NKG2D decoys with an organic derivatizing agent that is capable of reacting with selected side chains or the N- or C-terminal residues of NKG2D decoys. Derivatization with bifunctional agents can be useful, for instance, for crosslinking NKG2D decoys to a water-insoluble support matrix or surface for use in the methods described below, or for in vivo stability. Commonly used crosslinking agents include 1,1-bis(diazoacetyl)-2-phenylethane, glutaraldehyde, N-hydroxysuccinimide esters (e.g., esters with 4-azidosalicylic acid), homobifunctional imidoesters, including disuccinimidyl esters (e.g., 3,3'-dithiobis(succinimidylpropionate), bifunctional maleimides (e.g., bis-N-maleimido-1,8-octane) and agents such as methyl-3-((p-azidophenyl)dithio) propioimidate, and 1-ethyl-3-(-3-dimethylaminopropyl)carbodiimide hydrochloride.

Other modifications include deamidation of glutaminyl and asparaginyl residues to the corresponding glutamyl and aspartyl residues, respectively, hydroxylation of P and L, phosphorylation of hydroxyl groups of S or T residues, methylation of the amino groups of L, R, and H side chains (see, e.g., T. E. Creighton, Proteins: Structure and Molecular Properties, W.H. Freeman & Co., San Francisco, pp. 79-86 (1983)), acetylation of the N-terminal amine, and/or amidation of any C-terminal carboxyl group. In addition, modifications such as derivitization with polyethylene glycols (and other glycols) to increase the in vivo stability half-life are also included.

Glycosylation. In particular embodiments, the NKG2D decoys are glycosylated. Glycosylation is a type of post-translational modification that refers to the covalent attachment of sugars to proteins. Functions of glycosylation include contributing to proper protein folding, and facilitating cell-to-cell and/or protein-protein interactions.

Sugars that can be linked to proteins through glycosylation include glycans and monosaccharides, such glucose and fucose. Glycans are polysaccharides with sugar subunits linked by glycosidic bonds. Sugars that can be present in glycans include mannose, sialic acid, GlcNAc, galactose, and fucose. Glycans are a diverse class of molecules and can vary in the type of sugar moieties present, in the length of the chains of sugars, and in structure (branched or unbranched sugar chains). There are three major classes of glycans involved in protein glycosylation; N-linked glycans, O-linked glycans, and phospho-linked glycans.

In particular embodiments, the NKG2D decoys are N-linked glycosylated. N-linked glycans attach to the nitrogen atom of certain amino acids including N and R. In eukaryotic cells, N-linked glycosylation occurs during translation in the endoplasmic reticulum. Therefore, proteins that encode a signal peptide that signals for translation within the endoplasmic reticulum can become N-linked glycosylated. An N-linked glycosylation site can include N-X-(S), where X is any amino acid.

In particular embodiments, the human NKG2D monomer has three N-linked glycosylation sites (all N×S sequences), meaning a NKG2D$^{sed}$ with two monomers has six. Crystallography performed on embodiments disclosed herein confirms that all potential N-linked oligosaccharide sites can be glycosylated.

In particular embodiments, the NKG2D decoys are O-linked glycosylated. O-linked glycans attach to the hydroxyl (OH) of amino acids including S, T, Y, hydroxyl-K, and hydroxyl-P. In eukaryotic cells, O-linked glycosylation occurs in the Golgi apparatus. An O-linked glycosylation site can include (S or T)-X-X-P, where X is any amino acid.

In particular embodiments, the NKG2D decoy is glycosylated due to protein production using a eukaryotic cell expression system. All domains of life (eukaryote, bacteria, and archaea) are capable of protein glycosylation. However, glycosylation machinery can differ across domains and even across species. Therefore, a protein that is glycosylated when expressed in an autologous system may not become glycosylated upon expression in a heterologous system. One specific reason is if the glycosylation site of the protein is not recognized by the cell type used for expression.

Particular embodiments disclosed herein may become glycosylated due to expression methods used. For example, in particular embodiments, NKG2D decoys disclosed herein are formed using the Daedalus expression system as described in Pechman et al., Am J Physiol 294: R1234-R1239, 2008. The Daedalus system utilizes inclusion of minimized ubiquitous chromatin opening elements in transduction vectors to reduce or prevent genomic silencing and to help maintain the stability of decigram levels of expression. This system can bypass tedious and time-consuming steps of other protein production methods by employing the secretion pathway of serum-free adapted human suspension cell lines, such as 293 Freestyle. Using optimized lentiviral vectors, yields of 20-100 mg/l of correctly folded and post-translationally modified, endotoxin-free protein of up to 70 kDa in size, can be achieved in conventional, small-scale (100 ml) culture. At these yields, most proteins can be purified using a single size-exclusion chromatography step, immediately appropriate for use in structural, biophysical or therapeutic applications. Bandaranayake et al., Nucleic Acids Res., 2011 (November); 39(21). In some instances, purification by chromatography may not be needed due to the purity of manufacture according the methods described herein.

Siderocalin (Scn), also known as Lipocalin-2 or neutrophil gelatinase-associated lipocalin, is a member of the lipocalin family that binds siderophores, a type of small chelator, with very high affinity (in the sub-nanomolar range). Scn also has an exceptionally stable protein structure, and therefore is an ideal binding partner for fusion proteins, as the stability of the Scn domain can impart stability on the whole fusion protein. Additionally, Scn naturally contains a secretion signal, so Scn can be a useful fusion partner for of a variety of peptides, proteins, and protein domains, including when extracellular expression is desired. Further, Scn possesses a single N-linked glycosylation site, which is involved in correct processing in the ER before secretion.

In particular embodiments, Scn particularly refers to the first isoform of the human ortholog of Scn (SWISS-PROT Data Bank Accession Number P80188. SEQ ID NO: 45 represents P80188 with the first 20 amino acids deleted. Other isoforms of human Scn may also be used (for example, SEQ ID NO: 77). In particular embodiments, Scn can refer to the ortholog expressed by another species, such as the mouse ortholog (SEQ ID NO: 46, which is SWISS-PROT Data Bank Accession Number P11672 with the first 20 amino acids deleted), or the rat ortholog (SEQ ID NO: 47, which is SWISS-PROT Data Bank Accession Number P30152 with the first 20 amino acids deleted). For additional orthologs, see FIG. 29 (SEQ ID NOs: 48-62) and Correnti & Strong, (2013) "Iron Sequestration in Immunity" In Metals in Cells, Encyclopedia of Inorganic and Bioinorganic Chemistry. (Culcotta & Scott, eds.) John Wiley & Sons, pp. 349-59.

In particular embodiments, an exemplary expression construct includes: a signal peptide//a flag tag//a his tag//a linker//a siderocalin//a TEV protease site//NKG2D monomer 1//and NKG2D monomer 2. For example, such a sequence could include:
the signal peptide: METDTLLLWVLLLWVPGSTG (SEQ ID NO: 63) or TDTLLLWVLLLWVPGSTG (SEQ ID NO: 68);
the flag tag: (SEQ ID NO: 41); DYDE (SEQ ID NO: 69); or DYKDDDDK (SEQ ID NO: 74);
the his tag: (SEQ ID NO: 42);
the linker: GGS or SGGGS (SEQ ID NO: 70);
the siderocalin: (SEQ ID NO: 45) or (SEQ ID NO: 77);
the TEV protease site: ENLYFQK (SEQ ID NO: 64);
the NKG2D monomer 1: (SEQ ID NO: 1 or an extracellular fragment thereof); (SEQ ID NO: 76 or an extracellular fragment thereof); (SEQ ID NO: 65); (SEQ ID NO: 66); or (SEQ ID NO: 79); and the NKG2D monomer 2: (SEQ ID NO: 1 or an extracellular fragment thereof); (SEQ ID NO: 76 or an extracellular fragment thereof); (SEQ ID NO: 65); (SEQ ID NO: 66); or (SEQ ID NO: 79).

Together this exemplary sequence with selected options can provide:

```
                                          (SEQ ID NO: 67)
METDTLLLWVLLLWVPGSTGDYKDEHHHHHHGGSQDSTSDLIPAPPLSKV

PLQQNFQDNQFQGKWYVVGLAGNAILREDKDPQKMYATIYELKEDKSYNV

TSVLFRKKKCDYWIRTFVPGCQPGEFTLGNIKSYPGLTSYLVRVVSTNYN

QHAMVFFKKVSQNREYFKITLYGRTKELTSELKENFIRFSKSLGLPENHI

VFPVPIDQCIDGGGSENLYFQKSGGGSNQEVQIPLTESYCGPCPKNWICY

KNNCYQFFDESKNWYESQASCMSQNASLLKVYSKEDQDLLKLVKSYHWMG

LVHIPTNGSWQWEDGSILSPNLLTIIEMQKGDCALYASSFKGYIENCSTP

NTYICMQRTVQIPLTESYCGPCPKNWICYKNNCYQFFDESKNWYESQASC

MSQNASLLKVYSKEDQDLLKLVKSYHWMGLVHIPTNGSWQWEDGSILSPN

LLTIIEMQKGDCALYASSFKGYIENCSTPNTYICMQRTV.
```

In particular embodiments, an exemplary expression construct can include:
the signal peptide: (SEQ ID NO: 63) or (SEQ ID NO: 68);
the flag tag: (SEQ ID NO: 41); (SEQ ID NO: 69); or (SEQ ID NO: 74);
the his tag: (SEQ ID NO: 42);
the linker: GGS or (SEQ ID NO: 70);
the siderocalin: (SEQ ID NO: 45) or (SEQ ID NO: 77);
TEV protease site: (SEQ ID NO: 64);
the linker: GGS or (SEQ ID NO: 70);
the NKG2D monomer 1: (SEQ ID NO: 2 or an extracellular fragment thereof); (SEQ ID NO: 71); or (SEQ ID NO: 72);
and the NKG2D monomer 2: (SEQ ID NO: 2 or an extracellular fragment thereof); (SEQ ID NO: 71); or (SEQ ID NO: 72).

Together this exemplary sequence with selected options can provide:

```
                                          (SEQ ID NO: 73)
TDTLLLWVLLLWVPGSTGDYDEHHHHHHGGSQDSTSDLIPAPPLSKVPLQ

QNFQDNQFQGKWYVVGLAGNAILREDKDPQKMYATIYELKEDKSYNVTSV

LFRKKKCDYWIRTFVPGCQPGEFTLGNIKSYPGLTSYLVRVVSTNYNQHA

MVFFKKVSQNREYFKITLYGRTKELTSELKENFIRFSKSLGLPENHIVFP

VPIDQCIDGGGSENLYFQKSGGGSNKEVPVSSREGYCGPCPNNWICHRNN

CYQFFNEEKTWNQSQASCLSQNSSLLKIYSKEEQDFLKLVKSYHWMGLVQ

IPANGSWQWEDGSSLSYNQLTLVEIPKGSCAVYGSSFKAYTEDCANLNTY

ICMKRAVPVSSREGYCGPCPNNWICHRNNCYQFFNEEKTWNQSQASCLSQ

NSSLLKIYSKEEQDFLKLVKSYHVVMGLVQIPANGSWQWEDGSSLSYNQL

TLVEIPKGSCAVYGSSFKAYTEDCANLNTYICMKRAV.
```

Any and all of these sequences can also incorporate a multimerization domain, such as a C4b multimerization domain selected from SEQ ID NOs. 7-39. For example, SEQ ID NO: 78 of FIG. 13A provides SEQ ID NO: 67 with a C4b multimerization domain (SEQ ID NO: 7 preceded by GS) and an amino acid substitution in the Scn sequence (SEQ ID NO: 77).

Compositions. Generally, NKG2D decoys can be formulated into pharmaceutically useful compositions, whereby therapeutically effective amounts of NKG2D decoys are combined in admixture with a pharmaceutically acceptable carrier. Salts and/or pro-drugs of NKG2D decoys can also be used.

A pharmaceutically acceptable salt includes any salt that retains the activity of the NKG2D decoys and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, procaine, and the amino acids K or R.

A prodrug includes an active ingredient which is converted to a therapeutically active compound after administration, such as by cleavage of a NKG2D decoy or by hydrolysis of a biologically labile group.

In particular embodiments, the compositions include NKG2D decoys of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA.

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the NKG2D decoys or helps to prevent denaturation or adherence to the container wall. Typical stabilizers can include polyhydric sugar alcohols; amino acids, such as R, K, G, Q, N, H, A, ornithine, L-leucine, 2-phenylalanine, E, and T; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on NKG2D decoy weight.

The compositions disclosed herein can be formulated for administration by, for example, injection, inhalation, infusion, insertion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intratumoral, intramuscular, intravesicular, and/or subcutaneous ingestion, injection, or insertion.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as caramel, peppermint, oil of wintergreen, cherry flavoring, orange flavoring, etc. can also be used.

Compositions can be formulated as an aerosol. In particular embodiments, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated containing a powder mix (including flavored mixes) of NKG2D decoys and a suitable powder base such as lactose or starch.

Compositions can also be formulated as suppositories and/or depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers containing at least one NKG2D decoy. Various sustained-release materials have been established and are well known by those of ordinary skill in the art. Sustained-release systems may, depending on their chemical nature, release NKG2D decoys following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly (caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Del.), poly(vinyl alcohol) (PVA), Brij® (Croda Americas, Wilmington, Del.), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies. Any combination of formulation parameters can also be used so long as the combination does not detract from the appropriateness of the administration form (e.g., a flavored suppository).

Kits. Also disclosed herein are kits including one or more containers including one or more of the NKG2D decoys (e.g. in NKG2D$^{scd}$, pre-multimerized, or multimerized form) and/or compositions described herein. Associated with such container(s) can be a notice in the form prescribed by a governmental agency regulating the manufacture, use, or sale of pharmaceuticals or biological products, which notice reflects approval by the agency of manufacture, use, or sale for human administration.

Optionally, the kits described herein further include instructions for using the kit in the methods disclosed herein. In various embodiments, the kit may include instructions regarding preparation of the NKG2D decoys, multimerization of the decoys, and/or compositions for administration; administration of the NKG2D decoys and/or compositions; appropriate reference levels to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In various embodiments, possible side effects and contraindications to further use of components of the kit based on a subject's symptoms can be included.

Methods of Use. Particular embodiments utilize NKG2D decoys to (i) identify NKG2DL; (ii) treat cancer, graft vs. host disease (GVHD), and inflammatory conditions; and (iii) potentiate an immune response against a vaccine as well as many other potential uses. NKG2D decoys bind to NKG2DL with high affinity and/or avidity and block or substantially reduce native NKG2D activation with little to virtually no risk of activation through native NKG2D binding.

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with NKG2D decoys disclosed herein including pharmaceutically-acceptable salts, tautomers, isomers and prodrugs thereof and/or pharmaceutical compositions including the NKG2D decoys including pharmaceutically-acceptable salts, tautomers, isomers and prodrugs thereof. Treating subjects includes delivering therapeutically effective amounts. Therapeutically effective amounts include those that provide effective amounts, prophylactic treatments and/or therapeutic treatments. Therapeutically effective amounts need not produce a full desired outcome (e.g., potentiation of vaccine response), treatment or cure for a condition but can also provide a partial outcome or treatment such as alleviation or improvement of at least one cause or symptom of the condition.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to the assessment of a condition.

A "prophylactic treatment" includes a treatment administered to a subject who does not display signs or symptoms of a condition or displays only early signs or symptoms of the condition such that treatment is administered for the purpose of diminishing, preventing, or decreasing the risk of developing the condition further. Thus, a prophylactic treatment functions as a preventative treatment against a condition. In particular embodiments, prophylactic treatments include vaccines and/or can prevent, reduce, or delay the development or return of a condition.

A "therapeutic treatment" includes a treatment administered to a subject who displays symptoms or signs of a condition and is administered to the subject for the purpose of diminishing or eliminating those signs or symptoms of the condition. The therapeutic treatment can reduce, control, or eliminate the presence or activity of the condition (or its underlying causes) and/or reduce control or eliminate side effects of the condition.

Function as an effective amount, prophylactic treatment or therapeutic treatment are not mutually exclusive, and in particular embodiments, administered dosages may accomplish more than one treatment type.

Identification of NKG2DL. In particular embodiments, NKG2D decoys can be administered to a subject to locate cells or areas of the subject's anatomy bearing NKG2DL. In these embodiments, NKG2D decoys are associated with a detectable label. Following administration, the NKG2D decoys will bind to NKG2DL within the subject, permitting detection of these cells or areas within the subject through the detectable label.

Detectable labels can be detected following administration to a subject using imaging techniques. Examples of imaging techniques include magnetic resonance imaging (MRI), magnetic resonance tomography (MRT), positron emission tomography (PET), computer tomography (CT), single-photon emission computed tomography (SPECT) and optical imaging, such as x-ray.

Detectable labels can include any suitable label or detectable group detectable by, for example, optical, spectroscopic, photochemical, biochemical, immunochemical, electrical, optical or chemical means. Such detectable labels include radiolabels (e.g., $^{35}S$, $^{125}I$, $^{32}P$, $^{3}H$, $^{14}O$, $^{131}I$), radioacoustic labels, enzyme labels (e.g., horseradish peroxidase, hydrolases, alkaline phosphatase), chemiluminescence labels, fluorescence labels (e.g., rhodamine, phycoerythrin, fluorescein, fluorescent proteins, Texas red), fluorescent proteins (e.g. a green fluorescent protein or one of its many modified forms), gold beads, magnetic beads (e.g. Dynabeads™), and biotin (with labeled avidin or streptavidin).

NKG2D decoys also can be utilized to identify and/or characterize NKG2DL in ex vivo and/or in vitro research settings.

Methods to Treat Cancer. Cancer (neoplasia) is characterized by deregulated cell growth and cell division. It has the potential to invade to other parts of the body. In 2015, there is an estimated 1.7 million new cases of cancer and 590,000 cancer deaths in the U.S. There are various types of cancer, including acoustic neuroma, adenocarcinoma, astrocytoma, basal cell cancer, bile duct cancer, bladder cancer, brain cancer, breast cancer, bronchogenic cancer, central nervous system cancer, cervical cancer, chondrosarcoma, choriocarcinoma, colon cancer, craniopharyogioma, ependymoma, Ewing's tumor, fibrosarcoma, glandular cancer, glioma, hemangioblastoma, hepatocellular carcinoma, hepatoma, kidney cancer, leiomyosarcoma, liver cancer, liposarcoma, lung cancer, melanoma, medulloblastoma, medullary cancer, medullary thyroid cancer, menangioma, mesothelioma, myxosarcoma, neuroblastoma, oligodendroglioma, osteogenic sarcoma, ovarian cancer, papillary adenocarcinomas, papillary thyroid cancer, pancreatic cancer, pheochromocytomas papillary cancer, pineal cancer, prostate cancer, renal cell cancer, retinoblastoma, rhabdomyosarcoma, sarcoma, sebaceous gland cancer, seminoma, skin cancer, squamous cell cancer, sweat gland cancer, synovioma, testicular cancer, and/or Wilms' tumor. Cancers also include blood or other liquid cancers (e.g., lymphoma; leukemia).

Effective amounts disclosed herein can cause a statistically-significant effect in an animal model or an in vitro assay relevant to the assessment of a NKG2D decoy as an anti-cancer therapeutic.

In particular embodiments, a "prophylactic treatment" prevents, reduces, or delays metastasis from a primary tumor site and/or prevents, reduces, or delays a cancer recurrence.

Within a subject, a "therapeutic treatment" can decrease the number of cancer cells, decrease the number of metastases, decrease tumor volume, induce apoptosis of cancer cells, induce cancer cell death, induce chemo- or radio-sensitivity in cancer cells, inhibit angiogenesis near cancer cells, inhibit cancer cell proliferation, and/or inhibit tumor growth. Therapeutic treatments can also increase life expectancy, prolong a subject's life, reduce cancer-associated pain, and/or reduce relapse or re-occurrence of the cancer following treatment. In particular embodiments therapeutically effective amounts prevent, reduce, or delay the number or severity of metastatic tumors.

In particular embodiments, a statistically-significant change in a desired direction (e.g., reduction or increase) of one of these parameters is required to determine that a dose provides a therapeutically effective amount.

Additional support for the use of NKG2D decoys in the treatment of cancer comes from Example 2 and Spear et al., *Cancer Immunity*, (1 May 2013) Vol. 13, page 8.

In particular embodiments, treating cancers includes treating NKG2D+ cancers such as ovarian cancer and blood cancers, such as acute myeloid leukemia. In particular embodiments, treating NKG2D+ cancer includes reducing soluble MICA or MICB binding to NKG2D. In particular embodiments, treating NKG2D+ cancer includes measuring soluble MICA or MICB in a subject with NKG2D+ cancer.

Methods to Treat Graft vs. Host Disease (GVHD). GVHD is a generic name for diseases that are caused by the immune reaction of transferred or transplanted immunocompetent cells (graft; e.g., mature T cells) against host (recipient subject) tissues and that can induce severe organ toxicity leading to death in some cases. GVHD can occur despite aggressive immunosuppressive prophylaxis even when the donor is a perfectly matched (HLA identical) sibling. It is a consequence of interactions between antigen presenting cells of recipients and mature-cells of a donor.

GVHD can be divided into acute and chronic forms: the acute or fulminant form of the disease (aGVHD) is normally observed within the first 100 days post-transplant, and is a major challenge to transplants owing to associated morbidity and mortality; the chronic form of graft-versus-host-disease (cGVHD) normally occurs after 100 days. The appearance of moderate to severe cases of cGVHD adversely influences long-term survival.

NKG2D activation plays an important role in GVHD. Thus, administration of NKG2D decoys can provide prophylactic and/or therapeutic treatments against GVHD.

Efficacy of GVHD effective amounts can be assessed using animal models. For example, immunodeficient NOD-.SCIDyc−/− (NSG) mice (e.g., from the Jackson Laboratory) can be irradiated at 2 Gy before injection of $210^6$ total Peripheral Blood Mononuclear cells (PBMC) from healthy donors. Weight loss and survival of injected mice overtime can be assessed as clinical parameters of GVHD appearance and severity. Weight loss can be represented as the percentage of initial weight of the injected mice at different time points after PBMC injection. Blood and spleen cells can also be harvested and frequencies of T cells can be determined by flow cytometry using human-specific fluorescent mAbs.

GVHD can also be manifested (and hence therapeutically effective amounts providing prophylactic and/or therapeutic treatments identified) based on presence and/or severity of intestinal inflammation, sloughing of the mucosal membrane, diarrhea, abdominal pain, nausea, and vomiting. GVHD can be diagnosed via intestinal biopsy. Liver GVHD can be measured by bilirubin level. Skin GVHD results in a diffuse maculopapular rash, sometimes in a lacy pattern. Kidney function can be assessed by measuring creatinine and/or BUN levels. Therapeutically effective amounts disclosed herein can reduce these symptoms and/or preserve organ function in a statistically-significant manner.

Acute GVHD can be staged as follows: overall grade (skin-liver-gut) with each organ staged individually from a low of 1 to a high of 4. Patients with grade IV GVHD usually have a poor prognosis. Therapeutically effective amounts disclosed herein can reduce GVHD scores or prevent occurrence of a grade IV score.

Additional support for the use of NKG2D decoys as an effective treatment against GVHD comes from Karimi et al., *Blood*, prepublished on-line Mar. 18, 2015 doi:10.1182/blood-2015-02-629006 (NKG2D Expression by CD8+ T-Cells Contributes to GVHD and GVT Effects in a Murine Model of Allogeneic HSCT).

Methods to Treat Inflammatory Conditions. Inflammatory conditions refer to any disorder or disease characterized or caused by excessive or uncontrolled inflammation, or any aspect of inflammation such as redness, swelling, heat, and pain. Examples of inflammatory conditions include allergies (e.g., allergic rhinitis/sinusitis, skin allergies (e.g., urticaria/hives, angioedema, atopic dermatitis), food allergies, drug allergies, insect allergies, and rare allergic disorders such as mastocytosisasthma), asthma, arthritis (e.g., osteoarthritis, rheumatoid arthritis, and spondyloarthropathies), gastrointestinal inflammation, neuroinflammatory disorders, and autoimmune disorders.

Autoimmune disorders include any condition, or disease in which the immune system mounts a reaction against self cells or tissues, due to a breakdown in the ability to distinguish self from non-self or otherwise. Examples of autoimmune disorders include Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease, polymyositis, Guillain Barre, Wegener's granulomatosus, polyarteritis nodosa, polymyalgia rheumatica, temporal arteritis, Bechet's disease, Churg-Strauss syndrome, Takayasu's arteritis, and others. Autoimmune disorders can involve any component of the immune system, and can target any cell or tissue type in the body.

U.S. Pat. No. 9,127,064 provides a method of treating inflammatory conditions including autoimmune disorders. More particularly, U.S. Pat. No. 9,127,064 describes a method of treating rheumatoid arthritis, inflammatory bowel disease (IBD) (including Crohn's disease and ulcerative colitis), systemic erythromatosis lupus (SLE), psoriasis, psoriatic arthritis, multiple sclerosis, celiac disease, viral disease (such as, e.g., viral hepatitis), and transplant rejection of various organs and tissues (including heart and bone marrow). These inflammatory conditions are treated by reducing or inhibiting hNKG2D activation, hNK2D-signalling, or activation of hNKG2D-expressing NK or T cells using human or humanized anti-hNKG2D antibodies. The NKG2D decoys disclosed herein are preferable treatments because of the significantly reduced risk of NKG2D binding and activation.

Therapeutically effective amounts providing effective amounts, prophylactic treatments and/or therapeutic treatments can be identified by selecting a relevant animal or clinical model of the particular inflammatory disease at issue and identifying a statistically-significant effect or improvement.

Additional support for the use of NKG2D decoys disclosed herein in the effectiveness against autoimmune disorders such as rheumatoid arthritis, celiac disease and diabetes is provided by Steigerwald et al., *mAbs*, 1:2, 115-127 (March/April 2009).

Methods to Potentiate Immune Responses against a Vaccine. Vaccines increase the immunity of a subject against a particular condition, such as infection by a virus (e.g., HIV, HCV). Therefore, in particular embodiments, a vaccine may be administered prophylactically, for example to a subject that is immunologically naive (e.g., no prior exposure or experience with a condition or limited prior exposure or experience with a condition).

Vaccine efficacy is often significantly decreased in the elderly and in developing countries including vaccines with very well-established efficacy in the U.S. and Europe such as the measles, polio and rotavirus vaccines (e.g., 90% efficacy in Europe vs. 32% in South Africa for the GSK RV1 rotavirus vaccine). While the causes for the efficacy decrease are certainly multi-factorial, a common denominator in these cases is the increased frequency of memory T cells highlighting their great potential as therapeutic target.

In the vaccine context, and not limiting the term as described elsewhere herein, subjects can include those in need of treatment, such as, those with an infection, as well as those prone to have or develop an infection, or those in whom infection is to be prevented, such as those in a high risk group for exposure to a pathogen, such as a virus. For example, NKG2D decoys can be administered to subjects who are at risk of developing a viral infection, or who have been exposed to a pathogen (e.g., virus), to prevent, reduce, or delay the development of infection or disease. In particular embodiments, NKG2D decoys can be administered to a subject likely to have been exposed to a pathogen or to a subject who is at high risk for exposure to a pathogen.

In particular embodiments, a vaccine is a therapeutically effective amount of an antigen in combination with an NKG2D decoy disclosed herein that induce an immune response in a subject against the antigen. The skilled artisan will appreciate that the immune system generally is capable of producing an innate immune response and an adaptive immune response. An innate immune response generally can be characterized as not being substantially antigen specific and/or not generating immune memory. An adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert.

"Immune response" refers to a response of the immune system to a vaccine antigen. In various exemplary embodiments, an immune response to a vaccine antigen can be an innate and/or adaptive response. In particular embodiments, an adaptive immune response can be a "primary immune response" which refers to an immune response occurring on the first exposure of a "naive" subject to a vaccine antigen. For example, in the case of a primary antibody response, after a lag or latent period of from 3 to 14 days depending on, for example, the composition, dose, and subject, antibodies to the vaccine antigen can be produced. Generally, IgM production lasts for several days followed by IgG production and the IgM response can decrease. Antibody production can terminate after several weeks but memory cells can be produced. In particular embodiments, an adaptive immune response can be a "secondary immune response", "anamnestic response," or "booster response" which refer to the immune response occurring on a second and subsequent exposure of a subject to a vaccine antigen. Generally, in a secondary immune response, memory cells respond to the vaccine antigen and therefore the secondary immune response can differ from a primary immune response qualitatively and/or quantitatively. For example, in comparison to a primary antibody response, the lag period of a secondary antibody response can be shorter, the peak antibody titer can be higher, higher affinity antibody can be produced, and/or antibody can persist for a greater period of time.

Thus, in particular embodiments, an immune response against a vaccine antigen will include antibody production against the vaccine antigen.

"Antibodies" refer to polyclonal or monoclonal antibodies that can be induced by vaccine antigen and later protect against its associated pathogen. In particular embodiments, an antibody prevents and/or ameliorates a symptom of a condition caused by a pathogen (e.g, AIDS caused by HIV infection). Thus, in particular embodiments, an antibody can bind to a pathogen based on exposure to the associated vaccine antigen. Without being bound by theory, in particular embodiments, the binding of an antibody to a pathogen can substantially neutralize or inactivate the pathogen. Thus, antibodies are capable of reducing or eliminating a pathologic effect of a pathogen. In particular embodiments, the binding of antibodies to pathogens may decrease or eliminate pathogen infectivity and/or virulence factor activity, including replication, synthesis, and/or toxicity. In particular embodiments, a statistically-significant decrease of one of these parameters upon re-exposure to a pathogen is required to determine that a NKG2D decoy potentiated an immune response against a vaccine, or, in other words, provided a therapeutically effective amount. In particular embodiments, a statistically-significant decrease in lag time to antibody upregulation following re-exposure to a pathogen is required to determine that a NKG2D decoy potentiated an immune response against a vaccine. In particular embodiments, potentiation of an immune response against a vaccine can be demonstrated by a statistically-significant increase in a vaccine parameter following its initial administration (e.g., higher peak antibody titers, higher affinity antibody production, antibody persistence).

For administration, therapeutically effective amounts (also referred to herein as doses) for all uses described herein can be initially estimated based on results from in vitro assays and/or animal model studies. Such information can be used to more accurately determine useful doses in subjects of interest.

The actual dose amount administered to a particular subject can be determined by a physician, veterinarian or researcher taking into account parameters such as physical and physiological factors including target, body weight, severity of condition, type of condition, stage of condition, previous or concurrent therapeutic interventions, idiopathy of the subject and route of administration.

Useful doses can range from 0.1 to 5 μg/kg or from 0.5 to 1 μg/kg. In other non-limiting examples, a dose can include 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1000 μg/kg, 0.1 to 5 mg/kg or from 0.5 to 1 mg/kg. In other non-limiting examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly)

The pharmaceutical compositions described herein can be administered by, without limitation, injection, inhalation, infusion, insertion, perfusion, lavage or ingestion. Routes of administration can include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual ingestion, injection, or insertion.

Example 1

NKG2D Decoy Manufacturing Protocols. Expression constructs were engineered as C-terminus fusions to a human Lipocalin protein Siderocalin (hScn) with N-terminus polyhistidine and short FLAG (SEQ ID NO: 74) affinity tags to facilitate protein expression analysis and purification. A Tobacco Etch Virus (TEV) protease cleavage site (SEQ ID NO: 64) was designed between C-terminus of hScn and N-terminus expression constructs.

Human Embryonic Kidney (HEK) suspension adapted freestyle 293F cells (Invitrogen) were used for protein expression. HEK 293F cells were stably transduced using expression lentivirus using previously outlined protocols (Bandaranayake, et al., supra; and Finton, et al. (2014) Ontogeny of recognition specificity and functionality for the broadly neutralizing anti-HIV antibody 4E10. PLoS Pathogens 10(9):e1004403). Stable lentiviral-based transductions were performed as follow, in brief, plasmids containing appropriate constructs were incorporated into replication incompetent lentiviral particles. HEK-293F cells plated in fresh media at one million per mL in 10 mL of fresh freestyle media were transduced with pseudovirus particles. Cells were incubated at 37° C. with 8% $CO_2$ and 80% humidity. 8-16 hours post transduction; cells were supplemented with 25 mL of fresh freestyle media. Transduction efficiency and protein expression were verified qualitatively by assessing GFP/mCherry expression using EVOS fluorescence imaging systems (Life Technologies). Three days post transduction; cells were expanded at a cell density of 0.5 million per mL.

Large-scale expression and purifications were performed in HEK 293F cells. Supernatant clarification and protein purification were done as described previously (Bandaranayake A D, et al., supra) with minor modification. Briefly, supernatants were harvested by centrifugation at 8000 rpm to remove cells and clarified by passing through 0.22-micron filter (Thermo Scientific). Clarified supernatants were supplemented with 150 mM Sodium Chloride. Affinity tagged protein purification was done using Ni-NTA. Recombinant proteins were further purified by size exclusion chromatography (SEC) using a Superdex 75 or Superdex 200 column (GE Healthcare) running in phosphate-buffered saline (PBS) running buffers. Eluted fractions were analyzed using SDS-PAGE. Protein concentrations were determined using calculated protein extinction coefficients and absorbance at 280 nm as a surrogate measure. Purified recombinant protein is further treated with TEV protease to separate fusion partners and generate soluble protein. Cleaved recombinant protein is further purified using affinity tag purification and SEC based gel filtration.

Example 2

Control of Tumor Initiation by NKG2D Naturally Expressed on Ovarian Cancer Cells. Introduction. The NKG2D lymphocyte receptor enables tumor immune surveillance by stimulating cytotoxic natural killer (NK) cells and CD8 T cells upon engagement of ligands that are induced on cancer cells by malignant transformation (Ullrich et al., Oncoimmunology 2013; 2(10):e26097). However, progressing tumors in humans stifle immune responses by various tactics that include chronic stimulation and functional disabling of lymphocyte NKG2D (Groh et al., Nature 2002; 419(6908):734-8, Groh et al., Nat Immunol 2006; 7(7):755-62, Hanaoka et al., J Immunol 2010; 185 (10):5732-42). In a conceptual twist, this detrimental activity is escalated as some cancer cells (such as subsets of breast, colon, ovarian, and prostate cancer cells) co-opt expression of NKG2D, thereby complementing the presence of its ligands for autonomous stimulation of oncogenic signaling (Benitez et al., Proc Natl Acad Sci USA 2011; 108(10):4081-6). In lymphocytes and cancer cells alike, stable NKG2D expression and function depend on its association with the DAP10 (DNAX-activating protein 10) signaling adaptor, which initiates PI3K-AKT and MAPK (mitogen-activated protein kinase) signaling cascades (Benitez et al., supra, Upshaw et al., Semin Immunol 2006; 18(3): 167-75). In cancer cells, these pathways control various aspects of tumorigenesis (Vivanco et al., Nat Rev Cancer 2002; 2(7):489-501, Normanno et al., Gene 2006; 366(1): 2-16). NKG2D ligands (NKG2DL) include MICA and MICB (MHC class I-related chains A and B) and six members of the ULBP (UL-16 binding protein) family (Eagle & Trowsdale, Nat Rev Immunol 2007; 7(9):737-44). NKG2DL are typically absent from the surface of most normal cells but are induced by oncogenesis-associated cellular stress and other disease conditions (Groh et al., Proc Natl Acad Sci USA 1996; 93(22):12445-50, Raulet et al., Annu Rev Immunol 2013; 31:413-41). NKG2DL are abundant in essentially all types of cancers but display variability in the representation of different ligand types (Groh et al., Proc Natl Acad Sci USA 1999; 96(12):6879-84, McGilvray et al., Int J Cancer 2010; 127(6):1412-20).

In diverse cancer settings, the continuous presence of NKG2DL correlates with poor clinical outcomes (McGilvray et al., Int J Cancer 2010; 127(6):1412-20, Wu et al., J Clin Invest 2004; 114(4):560-8, Cancer Immunol Immunother 2009; 58(5):641-52, Duan et al., Med Oncol 2011; 28(2):466-74, Fang et al., J Exp Clin Cancer Res 2014; 33:76). One plausible explanation considers the role of NKG2DL in promoting tumor immune evasion (Groh et al., Nature 2002; 419(6908):734-8, Groh et al., Nat Immunol 2006; 7(7):755-62, Hanaoka et al., J Immunol 2010; 185 (10):5732-42). An alternative scenario that is not mutually exclusive and tentatively supported by preliminary clinical data, is based on oncogenic effects of cancer cell NKG2D lending selective advantage to NKG2DL expression (Benitez et al., supra). NKG2D signaling may have the capacity to promote cancer cell plasticity and stemness-reprogramming, cellular changes that are considered central to tumor dissemination and metastasis formation (Scheel & Weinberg, Semin Cancer Biol 2012; 22(5-6):396-403). This notion is supported by phenotypic profiling of model tumor lines and ex vivo isolated breast cancer cells (Cai et al., PLoS One 2014; 9(10):e108942). As of yet, however, functional evidence that cancer cell NKG2D may indeed impart bona fide stem-like attributes is missing. This report aims at closing this knowledge gap. Building on a clinical correlation study of ovarian cancer, in vitro experiments and mouse model xenograft assays are presented, providing evidence that links NKG2D signaling to induction of cancer stem cell attributes and tumor initiation.

Materials and Methods. Ex vivo and xenograft ovarian cancer specimens, cell suspensions, and cell lines. Primary epithelial ovarian cancer (EOC) surgical specimens and annotated histopathology, International Federation of Gynecologists and Obstetricians (FIGO) tumor stage, and patient follow-up information were obtained from the Cooperative Human Tissue Network (www.chtn.nci.nih.gov) and the Pacific Ovarian Cancer Research Consortium Specimen Repository under Fred Hutchinson Institutional Review Board protocol #6007/552. Xenograft-derived tumors were harvested in accordance with Fred Hutchinson Institutional Animal Care and Use Committee (IACUC) protocol #1870. Processing of tumor specimens to single cell suspensions used a Human Tumor Tissue Dissociation Kit and a gentleMACS™ Dissociator (both Miltenyi Biotech; Cai et al., PLoS One 2014; 9(10):e108942). Single-cell processing of tumor spheres was in phosphate buffered saline (PBS) with 2 mM EDTA. The MDAH-2774 tumor line (American Type Culture Collection; ATCC) was grown in RPMI-1640/10% fetal bovine serum. The cytotoxic NKL cell line was grown in RPMI-1640/10% human serum/Interleukin 2 (100 IU; Chiron; Robertson et al., Exp Hematol 1996; 24(3):406-15).

Transfectants and siRNA transduction. MDAH-2774-derived NKG2D-DAP10 transfectants (MDAH-2774-TF cells) have been described (Cai et al., PLoS One 2014; 9(10):e108942). Additional transfectants with vector control (MDAH-2774 mock cells), and NKG2D RNAi-transduced MDAH-2774-TF-KO cells or scrambled RNAi controls (MDAH-2774-TF-scrRNAi cells) were generated as described (Benitez et al., supra). C1R-MICA, C1R-MICB, EL4-ULBP1, EL4-ULBP2, EL4-ULBP3, Mel-ULBP4, EL4-ULBP5, and C1R-ULBP6 transfectants have been described (Groh et al., Nat Immunol 2006; 7(7):755-62, Eagle et al., Eur J Immunol 2009; 39(11):3207-16). Silencing of NKG2D in ex vivo ovarian cancer cells was as with the MDAH-2774-TF line.

Engineering a biologic inhibitor of NKG2D signaling. "Single-chain dimer" forms of NKG2D (NKG2D$^{scd}$) were designed using a segment of the N-terminal arm of NKG2D as a linker between domains within the native homodimer. NKG2D$^{scd}$ targeting units were multimerized through fusion with the minimal heptamerization motif from human C4b binding protein (C4bbp) (Hofmeyer et al., J Mol Biol 2013; 425(8):1302-17), yielding highly-avid NKG2D$^{scd}$ heptamers (NKG2D$^{scd}_7$). Both NKG2D$^{scd}$ and NKG2D$^{scd}_7$ proteins were expressed using the Daedalus platform in HEK293F cells (Invitrogen) as fusions with Siderocalin (Scn) to stabilize expression (Bandaranayake et al., supra, Finton et al., PLoS Pathog 2013; 9(9):e1003639). A Tobacco Etch Virus protease (TEV) scission site (EDLYFQ; (SEQ ID NO: 75)) was inserted between the Scn and NKG2D moieties, and N-terminal polyhistidine and FLAG (SEQ ID NO: 74) tags were incorporated to facilitate purification. Recombinant proteins were purified from culture supernatants by immobilized metal chelate affinity, treated with TEV protease to release the Scn fusion partner, and polished by size exclusion chromatography (SEC). Purity and proper folding were confirmed by comparative reduced/non-reduced SDS-PAGE and analytical SEC. Endotoxin levels were checked using the PyroGene rFc assay (Lonza), and NKG2D$^{scd}_7$ was labeled with fluorescein isothiocyanate (Sigma-Aldrich) at a ratio of two fluorophores per protomer. Surface plasmon resonance (SPR) interaction analyses confirming that NKG2D$^{scd}$ and NKG2D$^{scd}_7$ retain proper binding to NKG2DL were performed at 25° C. with Biacore T100 instrumentation on a Series S CM5 chip (GE Healthcare). NKG2D$^{scd}$ and NKG2D$^{scd}_7$ proteins were immobilized using standard amine coupling chemistry, yielding surfaces with 310 or 240 SPR response units (RUs), respectively. A reference surface was generated by activating and deactivating a flow cell in the absence of protein. Serial two-fold dilutions of soluble, wild-type MICA (240 nM to 0.47 nM, or 100 nM to 0.78 nM), produced as previously described (Kim et al., Adv Protein Chem Struct Biol 2008; 75:85-105), were prepared in a running buffer of HBS-EP+ (10 mM HEPES, pH 7.4, 150 mM NaCl, 3 mM EDTA, 0.05% surfactant P-20; GE Healthcare) with 0.1 mg/mL bovine serum albumin. Duplicate MICA samples, interspersed with multiple buffer blanks, were randomly injected at 50 µL/min, with 3 min of association and 5 min of dissociation. Surfaces were regenerated with a 10 sec injection of 10 mM glycine, pH 2.0, followed by 2 min of buffer stabilization. Double-referenced data were fit with a 1:1 binding model using BIAevaluation 2.0.4 software (GE Healthcare).

Sphere formation assay. Tumor cells were cultured at $5 \times 10^3$, $1 \times 10^4$, and $5 \times 10^4$ cells/ml when using ex vivo cancer cells, or $1 \times 10^3$ cells/ml when using tumor lines, in 96-well ultra low attachment plates in mammary epithelial cell growth (MEBM) medium (Lonza) with 0.9% methylcellulose (Sigma Aldrich) (Kwong et al., J Mol Biol 2008; 384(5):1143-56). After 3-4 weeks, >100 µm diameter tumor spheres were microscopically counted in triplicate wells. For serial passaging, primary spheres were dissociated to single cells and replated in MEBM. Cultures were monitored for secondary and tertiary sphere formation for up to four weeks. To block NKG2D-NKG2DL engagement, assays were in the presence of either a cocktail of antibodies (Abs) specific for MICA/B (6D4; BD Pharmingen) and ULBP1-6 [clones 170818 (ULBP1), 165903 (ULBP2,5,6), and 166510 (ULBP3) from R&D Systems; and clone 1H11 (ULBP4; 3)], each at 10 µg/ml, or control isotype immunoglobulin (Ig), or the pan-NKG2DL-binding NKG2D$^{scd}_7$ (10 µg/ml) or PBS control. Agonist anti-NKG2D Ab (clone 149810) was from R&D Systems (Kwong et al., J Mol Biol 2008; 384(5):1143-56).

Animal studies. All animal procedures were approved by Fred Hutchinson IACUC protocol #1870. Female non-obese diabetic/severe combined immunodeficient (NOD/SCID) and NOD scid gamma (NSG) mice (6-8 weeks old) were obtained from the Fred Hutchinson Core Center of Excellence in Hematology (DK-56465 and DK-106829) and housed under pathogen-free conditions at the institutional Comparative Medicine Shared Resource. For implants, mice were anaesthetized with isoflurane and injected subcutaneously into dorsal flanks with either ex vivo isolated cancer cells, or MDAH-2774-derived lines, each in 100 µl growth medium (1:1 PBS/BD Matrigel™ Matrix; BD Bioscience). Tumor development was monitored three times per week until tumor nodules were palpable and then in daily intervals. At experimental endpoints or when a tumor parameter reached 1.5 cm, animals were euthanized and tumors resected. For in vivo NKG2DL masking, mice were treated in weekly intervals (up to 4 weeks post-transplant) with either a cocktail of anti-MICA/B, anti-ULBP1, -ULBP3, -ULBP4, and -ULBP5 Abs (see above) or NKG2D$^{scd}_7$ or relevant controls, all administered subcutaneously at the site of tumor cell implants or via tail vein injection. Antibody or NKG2D$^{scd}_7$ dosages were 10 µg per local application or 100 µg per tail vein injection.

Flow cytometry. Ex vivo EOC- or xenograft tumor-derived cell suspensions or sphere-derived single cells (in PBS/10% human serum/0.15% sodium azide) were variably incubated with pretitrated Ab-fluorochrome conjugates to NKG2D (clone 1D11; APC), CD45 (clone 2D1; APC-H7), CD44 (clone G44-26; PerCP-Cy5.5) (all BD Pharmingen), and EpCAM (clone 9C4; Alexa Fluor 488; Biolegend). NKG2DL expression was examined using an Ab cocktail (see above). Anti-H2Dd (clone 34-2-12; Biolegend) was used for exclusion of murine cells. DAPI was used for live/dead cell distinction. Isotype Igs were used as controls and background fluorescence subtracted. Testing for tumor cell aldehyde dehydrogenase activity was with the ALDEFLUOR™ kit (Stemcell Technologies) according to the manufacturer's instructions. Briefly, tumor cells were incubated with ALDEFLUOR {boron, [N-(2,2-diethoxyethyl)-5 [(3,5-dimethyl-2H-pyrrol-2-ylidene-kN)methyl]-1H-pyrrole-2-propanamida to KN1]difluoro-, (T-4)-(9Cl)} in the absence or presence of ALDH1 activity inhibitor diethylaminobenzaldehyde (DEAB) for 30 min at 37° C. followed by one wash using ALDEFLUOR assay buffer (Stemcell Technologies) and surface staining for NKG2D, CD45 and EpCAM. DEAB-treated cells served to set baseline ALDH1 activities. To confirm binding of NKG2D$^{scd}_7$ to all NKG2DL, corresponding transfectants (see above) were incubated with FITC-conjugated NKG2D$^{scd}_7$ (2 µg/ml) or PBS control for 30 min on ice followed by two PBS washes.

Stained cells were analyzed using a BD LSRII flow cytometer (BD Biosciences) and FlowJo software (Tree Star). Cell sorting was on a FACSAria™ (BD Biosciences).

Cytotoxicity assay. CellTrace™ Violet (Life Technologies)-labeled C1R-MICA and Oregon GreenR 488 (ThermoFisher Scientific)-labeled C1R-mock target cells were mixed at equal numbers and exposed to NKL cells at 1:1 effector to target (E:T) ratios in the presence or absence of NKG2D$^{scd}{}_{7}$ (10 µg/ml) or PBS control. Anti-MICA/B Ab 6D4 (10 µg/ml) served as positive blocking control. Following 4 h incubation at 37° C., E:T cell mixes were stained using LIVE/DEAD Fixable Aqua Dead Cell Stain Kit (Molecular Probes) and analyzed by flow cytometry. Ratios of live C1R-mock to C1R-MICA cells were used as measure of cytotoxic activity.

Statistical analyses. Frequencies of NKG2D$^+$ cancer cells were divided into subgroups represented by NKG2D Low (≤median % NKG2D$^+$ cells) and NKG2D High (>median % NKG2D$^+$ cells). Logistic regression was used to assess the relationship of NKG2D subgroups with disease recurrence and tumor stage (I/II vs. III/IV). Models were adjusted for patient age and odds ratios (OR) from these models refer to the increase in odds of outcome (disease recurrence or high tumor stage) for the NKG2D High subgroup compared to NKG2D Low. P-values were derived from likelihood ratio statistics and are two-sided. Kaplan-Meier curves and the log-rank test were used to analyze progression-free survival rates between the subgroups. All analyses were performed using R version 3.3.1 (R Core team. R: A language and environment for statistical computing. R Foundation for Statistical Computing, Vienna, Austria, 2006 URL https://www.R-project.org/). Extreme Limiting Dilution Analysis (ELDA) was as described (Hu & Smyth, J Immunol Methods 2009; 347(1-2):70-8).

Results. Correlation between NKG2D positive cancer cells and negative disease outcomes in epithelial ovarian cancer. In a previous study of a mixed cohort of breast, ovarian, colon, and prostate cancers, positive correlations were recorded between the frequencies of cancer cells bearing NKG2D (NKG2D$^+$ cancer cells) and tumor stage (Benitez et al., supra). This relationship could possibly reflect NKG2D effects on induction and/or maintenance of cancer stem-like traits. However, this interpretation is premature due to study limitations such as the inclusion of aggregate data from heterogeneous cancer cases and lack of disease outcome information. A follow-up study was therefore devised that focused on epithelial ovarian cancer (EOC) and addressed outcome. EOCs typically express abundant NKG2DL, which are strongly associated with negative disease outcomes (McGilvray et al., Int J Cancer 2010; 127(6):1412-20, Li et al., Cancer Immunol Immunother 2009; 58(5):641-52). Oncogenic effects of cancer cell NKG2D could thus be particularly apparent in this malignancy.

Figure 3A:
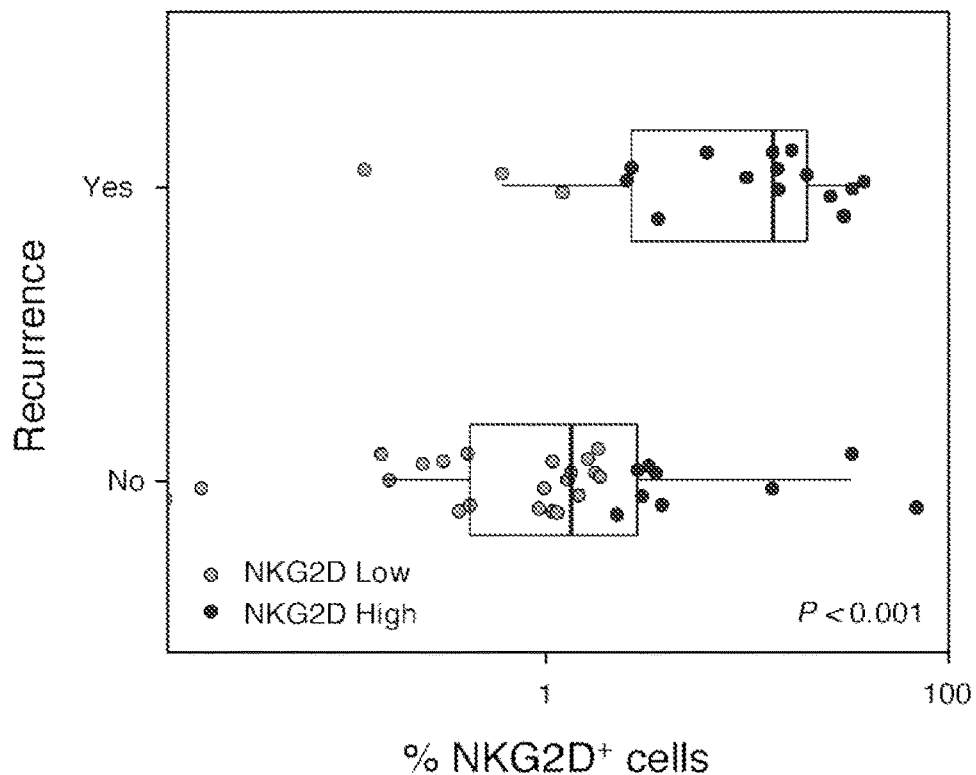
FIGS. 3A-3C. Negative clinical effects of cancer cell NKG2D in HGS EOC patients.
Figure 3B:
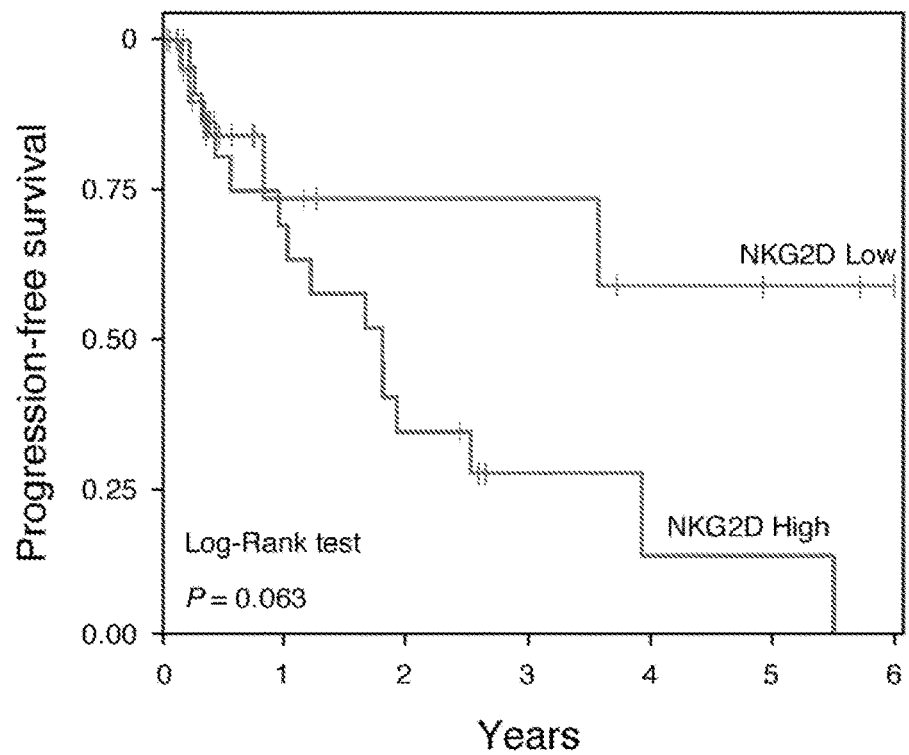
Figure 3C:
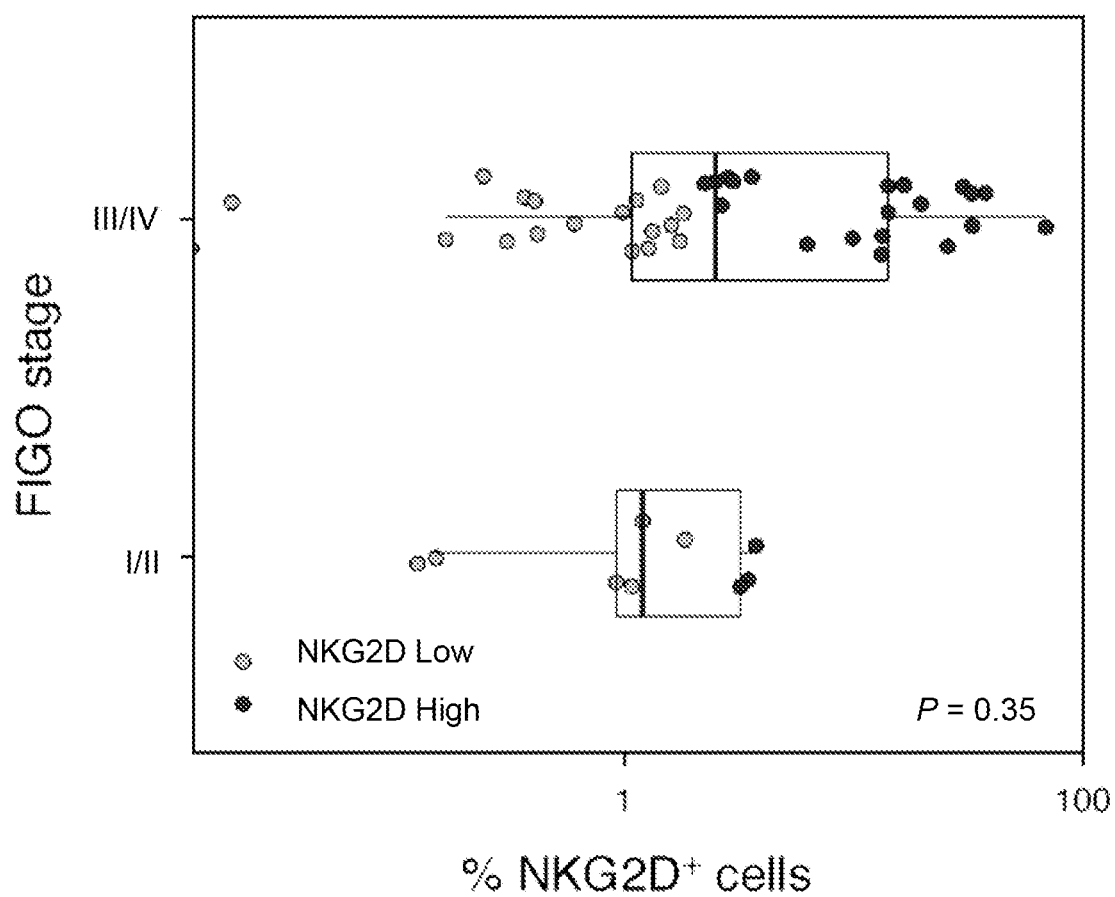

It was previously determined that cell surface flow cytometry of ex vivo isolated tumor cells is the method of choice for enumerating cancer cells expressing signaling competent NKG2D (Benitez et al., supra). A total of 47 primary EOC surgical specimens (procured between January 2009 and June 2015) were thus processed to cell suspensions and examined by flow cytometry for frequencies of cancer cells (defined as CD45-EpCAM$^+$) positive for surface NKG2D. EpCAM is a bona fide cancer cell marker although expression levels can vary substantially (Munz et al., Cancer Res 2009; 69(14):5627-9). Hence, all non-hematopoietic (CD45-) cells with above threshold EpCAM staining were scored as cancer cells. All tumors represented high grade serous (HGS) carcinoma, the most prevalent histological subtype among EOC (Kurman et al., Am J Pathol 2016; 186(4):733-47). FIGO stage and disease outcome annotations are summarized in FIG. 2. Patient treatments uniformly involved primary surgery followed by chemotherapy. Postoperative follow-up periods varied. Consistent with previous findings, NKG2D$^+$ cancer cells were present in all but one of the EOC specimens with frequencies between 0.1 and 66.9% (median 1.79%; FIG. 2). No NKG2D positivity was recorded among CD45-EpCAM-cells. For statistical appraisal of relationships between frequencies of NKG2D$^+$ cancer cells and clinical parameters, the cases studied were split into subgroups represented by NKG2D Low (≤median % NKG2D cells) and NKG2D High (>median % NKG2D$^+$ cells) (FIG. 2). As per likelihood ratio test, the odds of disease recurrence were significantly greater for the NKG2D High subgroup {OR=12.4; 95% confidence interval [CI]= (3.0, 70.3); P<0.001; FIG. 3A and FIG. 4}. Moreover, median progression-free survival rates were higher among the NKG2D Low subgroup cases (6+ years versus 1.8 years; P=0.063; FIG. 3B). Lastly, the NKG2D High subgroup, though not significant, tended to have higher tumor stages (FIGO III/IV) than the NKG2D Low subgroup [OR=2.1; 95% CI=(0.5, 11.1); P=0.35; FIG. 3C]. Altogether, these results implied negative clinical effects of cancer cell NKG2D.

Figure 7A:
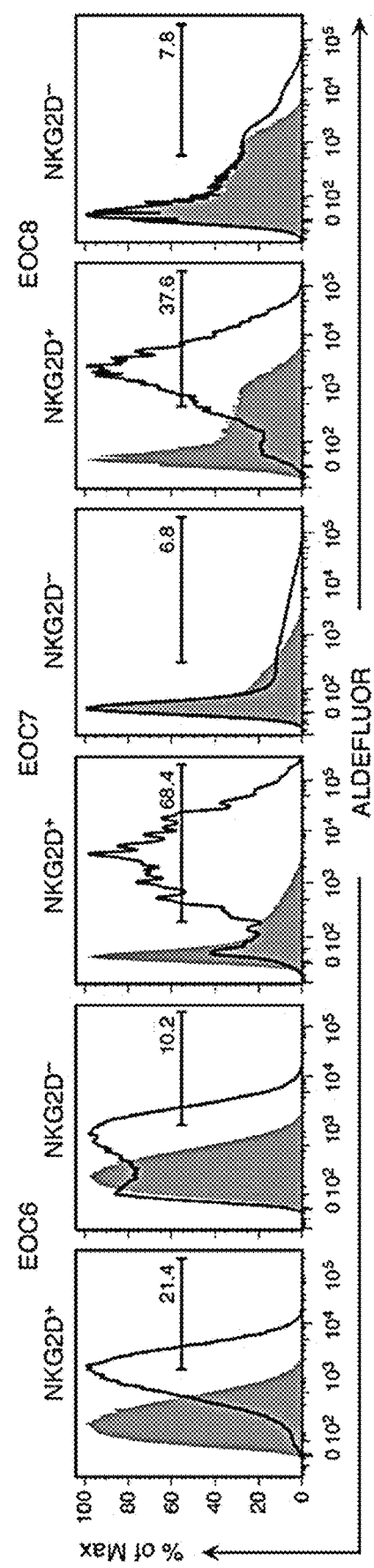
FIGS. 7A, 7B. Association of NKG2D with high ALDH1 activity in ex vivo HGS EOC cells as measured by ALDEFLUOR substrate conversion.
Figure 7B:
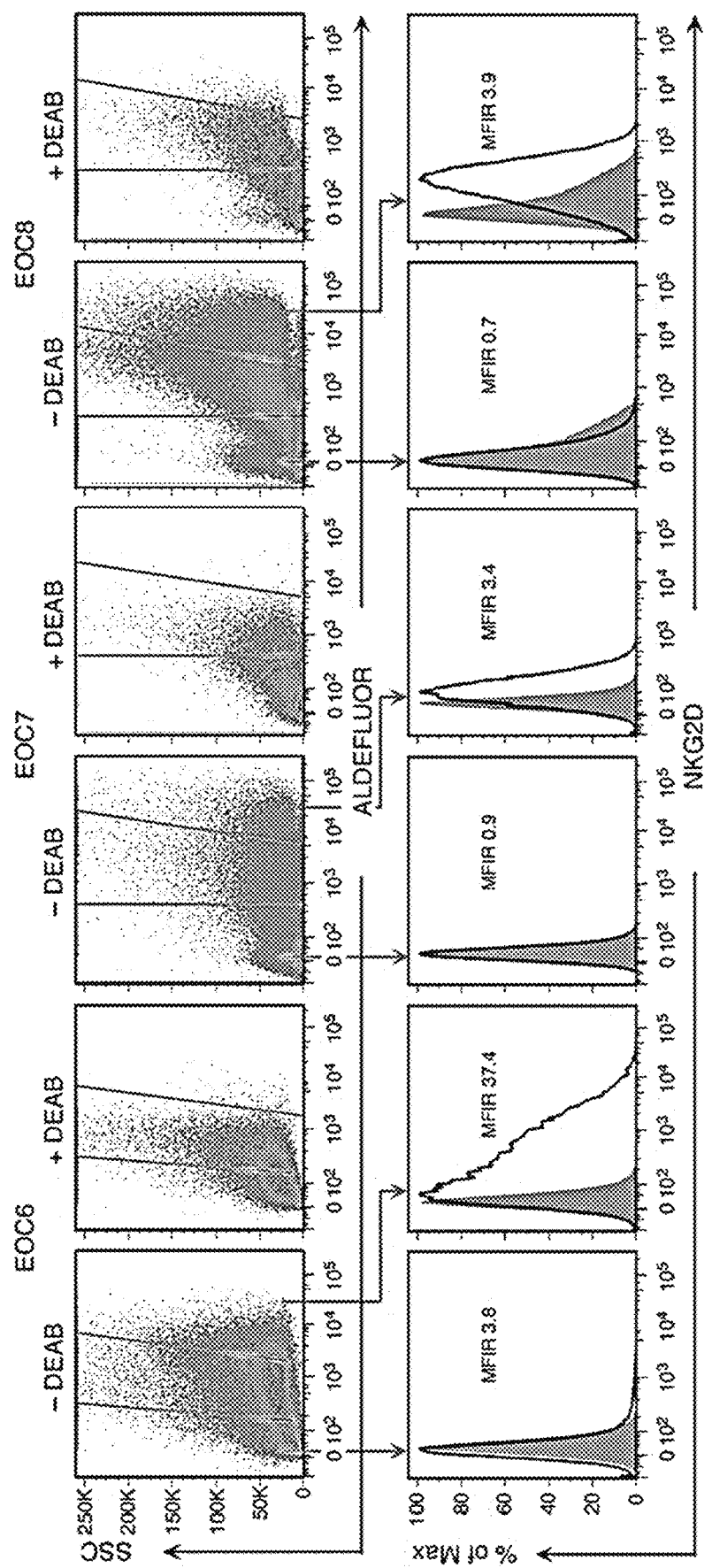

Association of NKG2D with markers of cellular plasticity among ex vivo ovarian cancer cells. With breast cancer cells, expression of NKG2D preferentially segregates with marker profiles characteristic of the epithelial-mesenchymal transition and metastable capacities (Cai et al., PLoS One 2014; 9(10):e108942). To test whether similar relationships apply to HGS EOC, ex vivo isolated tumor cell suspensions were examined by multi-parameter flow cytometry for non-hematopoietic (CD45-) NKG2D and markers of high plasticity traits represented by EpCAM together with CD44, or high aldehyde dehydrogenase (ALDH1) enzymatic activity (Silva et al., Cancer Res 2011; 71(11):3991-4001, Strauss et al., PLoS One 2011; 6(1):e161864, Kuroda et al., PLoS One 2013; 8(6):e65158). In a first set of five tumor specimens (EOC1 through EOC5; see FIG. 5 for clinical parameters of EOC specimens used throughout the remainder of study), proportions of EpCAM$^+$ CD4$^+$ cells were larger among NKG2D$^+$ as compared to NKG2D$^-$ cell populations [33.5% (+/−36.2) versus 3.5% (+/−3.3); FIG. 6]. A second set of seven CD45-tumor cell suspensions was examined for NKG2D and ALDH1 activity, which is considered the most stringent read-out for high cancer cell plasticity and was determined by ALDEFLUOR substrate conversion assay. All samples showed substantial overlaps between expression of NKG2D and ALDH1 activity, with a mean proportion of 30.2% (+/−19.4) of NKG2D$^+$ cells scoring high for ALDH1 activity, and most ALDEFLUOR$^{high}$ cells staining positive for NKG2D (FIGS. 7A and 7B; FIG. 6). EOC is a heterogeneous disease commonly classified by histology and grade as Type I or Type II (predominantly HGS) (Kurman et al., Am J Pathol 2016; 186(4):733-47). Analysis by flow cytometry of three Type I EOC specimens recapitulated the findings obtained earlier with the panel of HGS EOCs, suggesting EOC subtype independence (FIG. 6). Hence, it was concluded that EOC cell populations with surface NKG2D are enriched for cells with phenotypic attributes that have been associated with high cellular plasticity and stem cell-like functions.

Figure 8A:
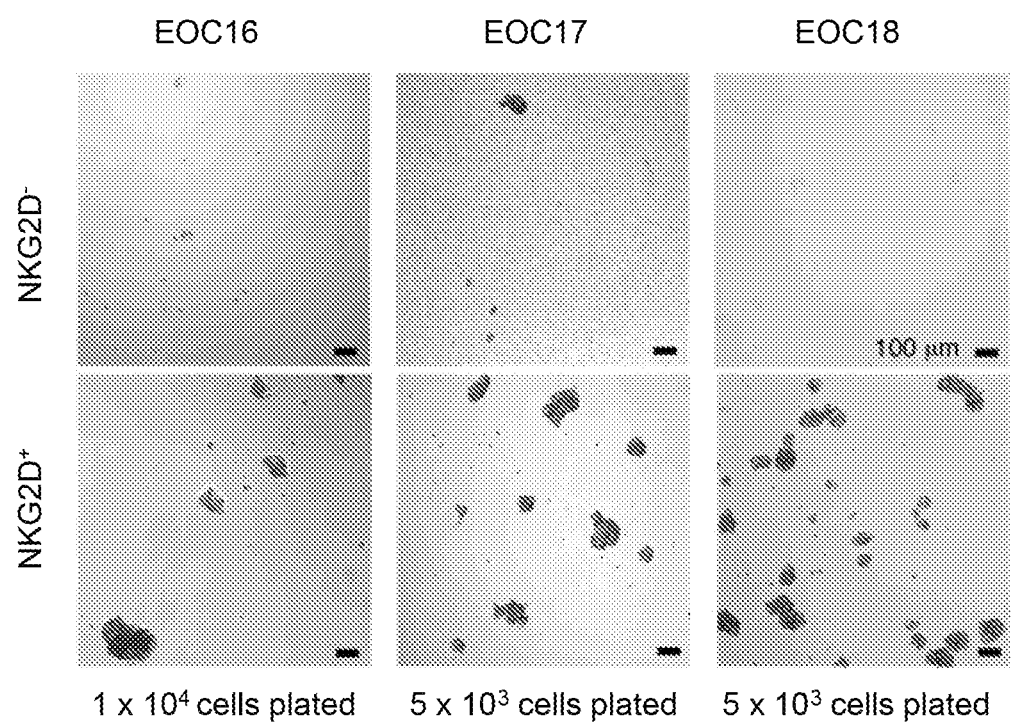
FIGS. 8A-8G. Tumor sphere-formation and tumor initiation by ex vivo NKG2D$^+$ HGS EOC cells.
Figures 8B, 8C:
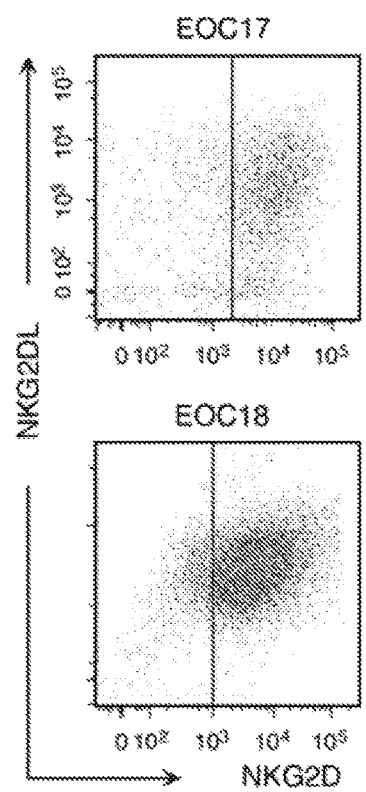

In vitro evidence for functional stem cell-like capacities of NKG2D$^+$ ovarian cancer cells. Stem cell-like cancer cells have the ability to form tumor spheres in cell culture (Dontu et al., Genes Dev 2003; 17(10):1253-70, Liao et al., PLoS One 2014; 9(1):e84941). CD45-NKG2D and control NKG2D⁻ cancer cells from altogether eight ex vivo HGS EOC tumor cell suspensions were FACSAria sorted. Cells were cultured under classical adherence-independent sphere-formation conditions and monitored for the appearance of spheres over a three-week period. NKG2D⁺ cells from all tumors formed numerous large (>100 µm diameter) spheres, even when plated at low cell densities, whereas control NKG2D⁻ cells generated spheres only when plated at high density and those that developed were rare and typically small (FIGS. 8A, 8B). NKG2D expression in spheres derived from NKG2D⁺ cells was monitored by flow cytometry of single cell-dissociated spheres. Although most cells stably retained NKG2D, some were negative suggesting that NKG2D⁺ cells may be able to give rise to NKG2D⁻ cells (FIG. 8C). Spheres derived from NKG2D⁻ cells remained NKG2D negative (FIG. 9A). Cancer cells usually express diverse combinations of NKG2DL that vary between tumors and individual cells (Groh et al., Proc Natl Acad Sci USA 1999; 96(12):6879-84, McGilvray et al., Int J Cancer 2010; 127(6):1412-20, Li et al., Cancer Immunol Immunother 2009; 58(5):641-52). Presence of NKG2DL on sphere cells, a prerequisite for NKG2D signaling, was confirmed using a cocktail of Abs to all NKG2DL (MICA/B and ULBP1 through ULBP6; FIG. 8C). To test for self-renewal capacity of sphere forming cells, primary spheres derived from NKG2D⁺ or control NKG2D⁻ cells (from specimens EOC22 and EOC23; FIG. 8B) were dissociated, and equal cell numbers plated for examination of secondary and tertiary sphere formation. Consistent with a relationship between NKG2D expression and stem cell-like attributes, only spheres originating from NKG2D⁺ cells could be passaged (FIG. 8B; Dontu et al., Genes Dev 2003; 17(10):1253-70).

Figure 8D:
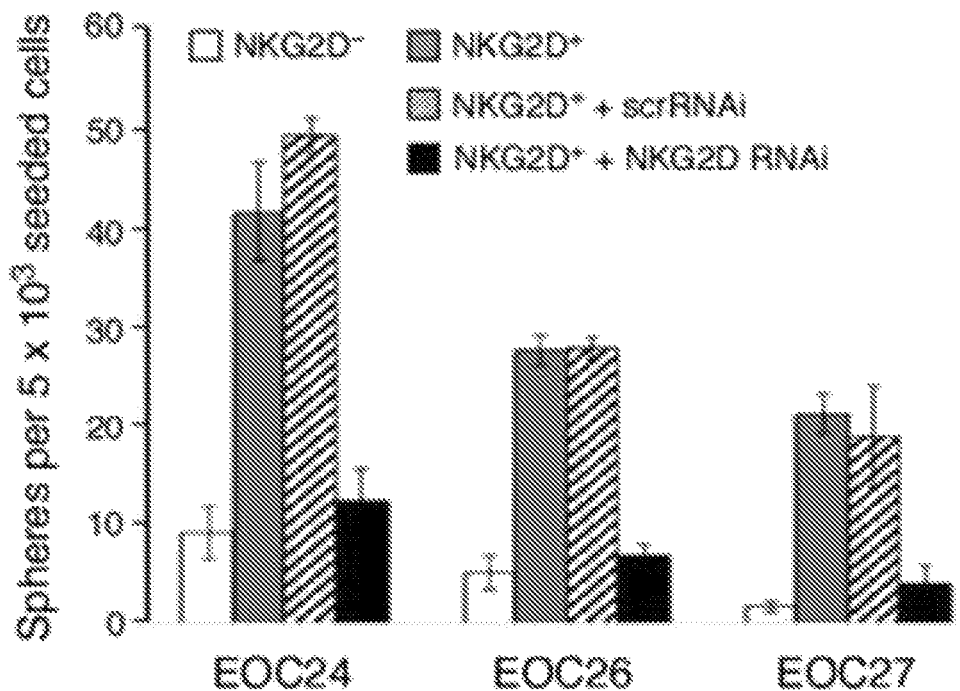
Figure 8E:
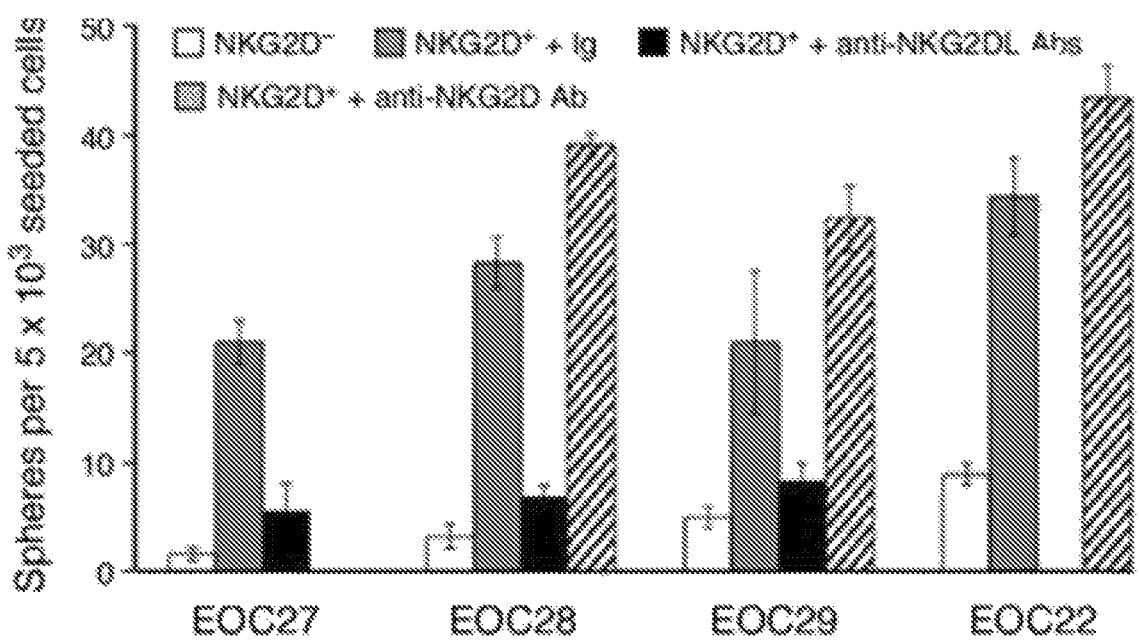

In support of a causal involvement of NKG2D in sphere formation, the sphere-forming abilities of NKG2D⁺ cancer cells were significantly reduced when NKG2D was depleted by recombinant lentivirus-mediated RNAi targeting whereas control scrambled RNAi had no effect (FIG. 8D). Similarly, culture of NKG2D⁺ cancer cells in the presence of anti-NKG2DL Abs diminished their sphere formation capacity (FIG. 8E), thus indicating that NKG2D signaling triggered by ligand engagement underlied the observed effect. Conversely, exposure of NKG2D cancer cells to an agonist anti-NKG2D antibody enhanced sphere formation (FIG. 8E). As with Type II EOC, sphere formation of Type I EOC-derived NKG2D⁺ cancer cells also exceeded those of their NKG2D⁻ counterpart (FIG. 9B).

Figures 8F, 8G:
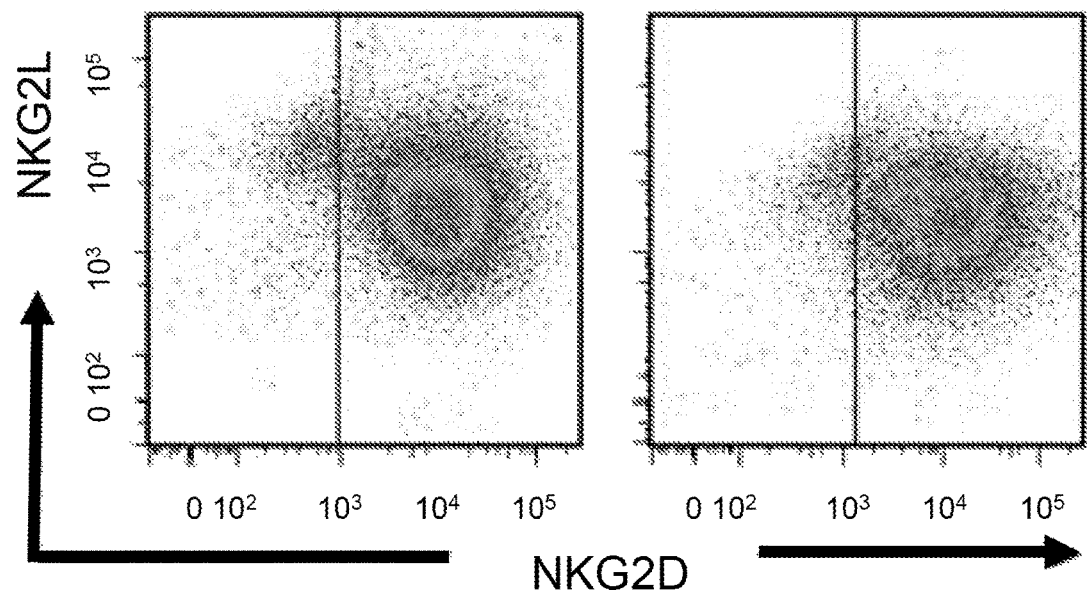

In vivo evidence for stem cell-like capacities of NKG2D⁺ ovarian cancer cells. Experimental proof of stem-cell like functions requires documentation of efficient tumor-initiating capacities upon xenografting in immunodeficient mice (Ponti et al., Cancer Res 2005; 65(13):5506-11). FACSAria-sorted CD45-NKG2D⁺ or control NKG2D⁻ cells from two HGS EOC tumor cell suspensions were subcutaneously inoculated at dosages of 5×10³ and 1×10⁴ cells into flanks of NSG mice. Three out of seven 5×10³ and six out of eight 1×10⁴ NKG2D⁺ cell implants initiated tumors as early as six weeks post inoculation. In contrast, only one of eight 1×10⁴ NKG2D⁻ cell implants led to tumor formation 14 weeks post inoculation (FIG. 8F). Extreme Limiting Dilution Analysis (ELDA) is commonly used for computational comparisons of enriched and depleted populations in stem cell assays (Hu & Smyth, J Immunol Methods 2009; 347(1-2):70-8). Application of ELDA-based calculations revealed significant differences in the frequencies of cells with tumor-initiating abilities among NKG2D⁺ as opposed to NKG2D-populations (FIG. 8F). Similar differences in tumor-initiating capacities were recorded with NKG2D⁺ and NKG2D⁻ cells isolated from a Type 1 EOC specimen (EOC36) (FIG. 8F). Flow cytometry of NKG2D⁺ implant-derived xenografts confirmed that NKG2D and NKG2DL were stably maintained on most tumor cells (FIG. 8G). However, as with the in vitro tumor sphere cultures, xenografts contained cells that lacked NKG2D, suggesting that NKG2D⁺ cells can give rise to NKG2D⁻ cells (FIG. 8G). Tumors derived from NKG2D⁻ cells remained NKG2D negative (FIG. 9C). Altogether, these data suggest that NKG2D⁺ ovarian cancer cell populations are enriched for cells with stem cell-like tumor-initiating abilities.

Figure 10A:
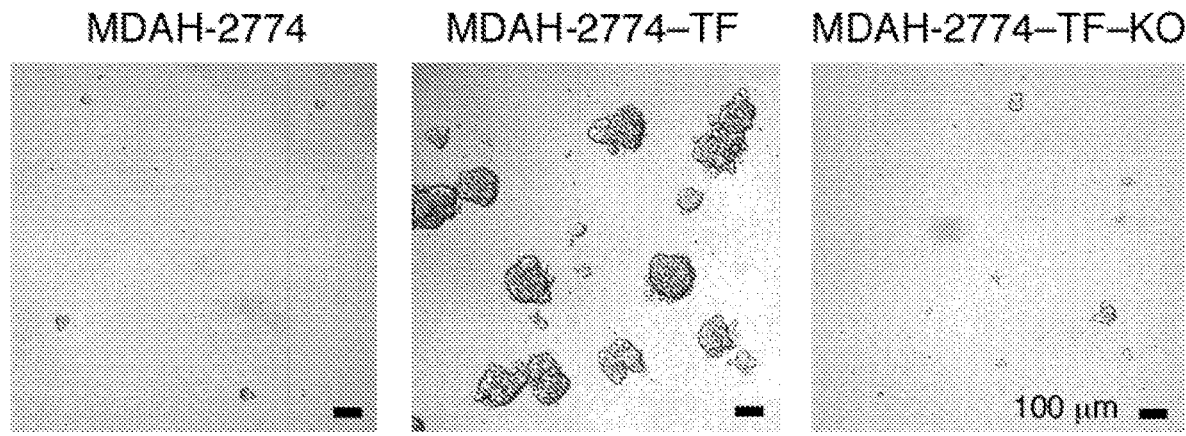
Figure 10B:
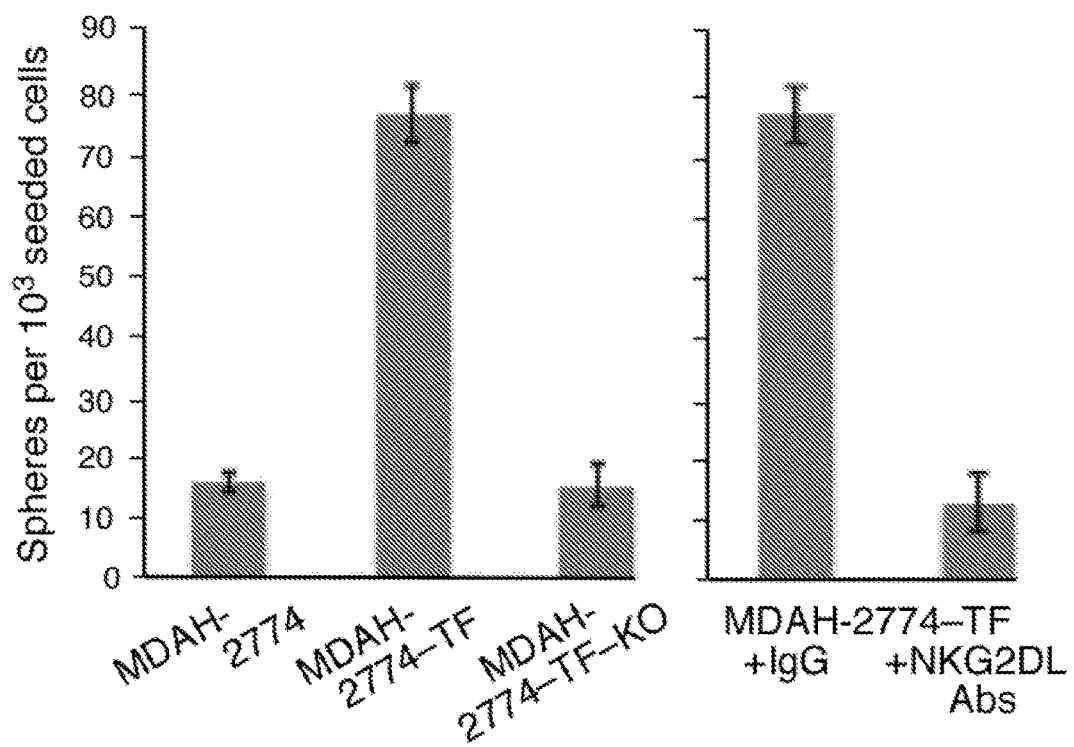

NKG2D signaling stimulates cancer stem cell-like tumor initiation. Direct involvement of NKG2D in tumor initiation was initially explored using experimental variants and controls of the MDAH-2774 ovarian tumor line which lacks endogenous NKG2D. Cells transfected with signaling competent NKG2D-DAP10 (MDAH-2774-TF) or vector control (MDAH-2774 mock), or transduced with NKG2D RNAi (MDAH-2774-TF-KO) or scrambled RNAi control (MDAH-2774-TF-scrRNAi) have been previously established or were newly made (Cai et al., PLoS One 2014; 9(10):e108942). MDAH-2774-TF cells recapitulated sphere-formation as recorded with ex vivo NKG2D⁺ ovarian cancer cells (FIGS. 10A and 10B) and were thus considered suitable for in vivo tumor initiation experiments in NOD/SCID mice.

Figure 11:
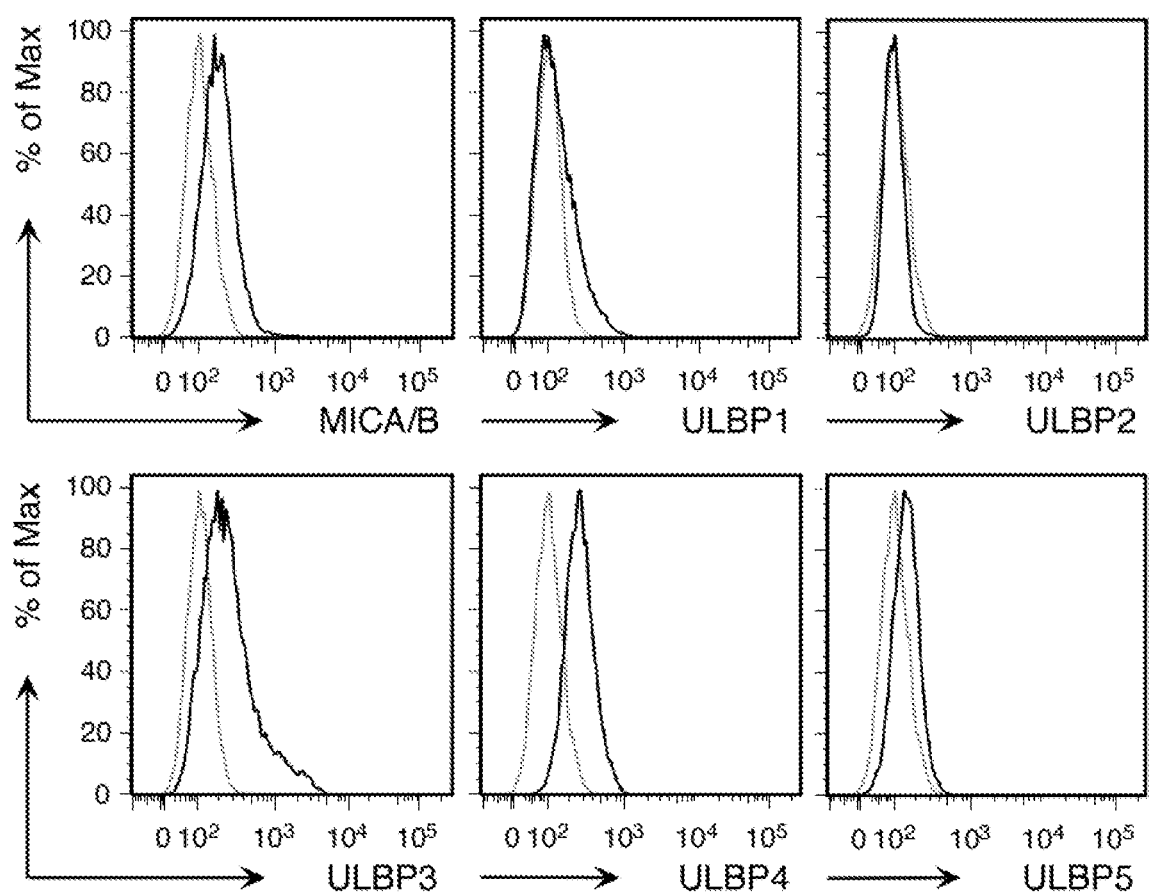
FIG. 11. Flow cytometry histogram profiles of the MDAH-2774 tumor line stained for NKG2DL, MICA/B and ULBP1-5.

In limiting dilution xenograft assays, three of four implants of as few as 100 MDAH-2774-TF cells formed tumors. Saturating tumor take with untransfected or mock transfected MDAH-2774 cells required implants of 1×10⁴ cells (FIG. 10C). NKG2D depletion in MDAH-2774-TF-KO cells restored negative control tumor formation rates (FIG. 10C). Involvement of NKG2D signaling by ligand engagement was formally confirmed by grafting mice with saturating (1×10⁴) or limiting (1×10²) MDAH-2774-TF cell numbers and administration of NKG2DL Abs (see FIG. 11 for expression of NKG2DL). Ab administration, either at the cell inoculation site or via tail vein injections, enhanced latency and reduced or prevented tumor formation (FIG. 10D).

To reinforce significance of these cell line-based experiments, tumor initiation by ex vivo NKG2D⁺ ovarian cancer cells sorted from HGS EOC37 (see FIG. 5) and transduced with NKG2D RNAi or control scrRNAi were examined. None of four 1.5×10⁴ cell implants of NKG2D-silenced cells led to tumor formation in NSG mice, whereas three of four control cell inoculations generated tumors. Altogether, these results establish a link between NKG2D and the tumor initiating potential residing within NKG2D⁺ ovarian cancer cell populations.

Figure 12A:
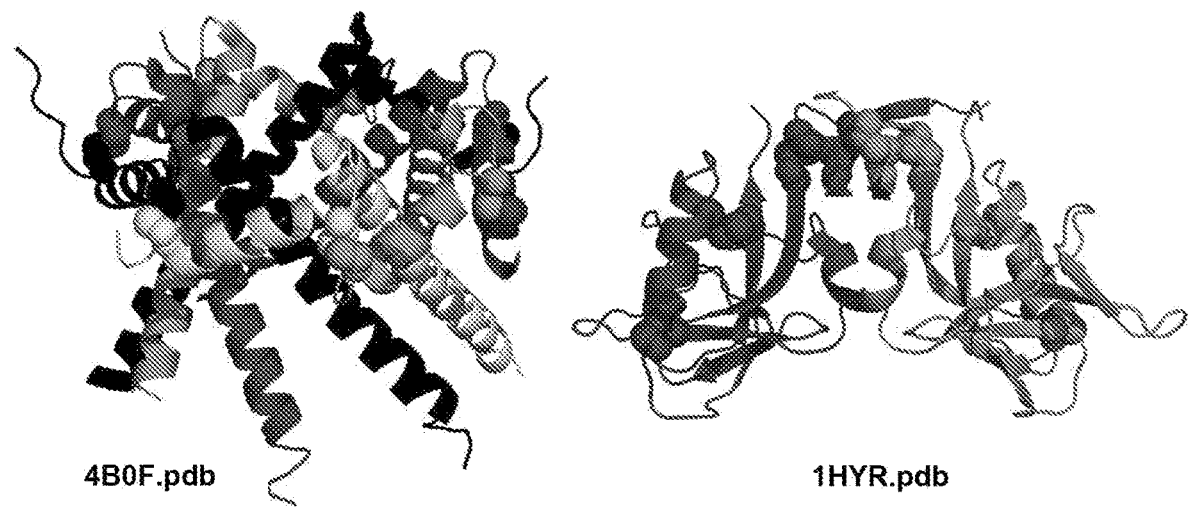
FIGS. 12A-12F. Engineering and properties of soluble NKG2D multimer.
Figure 12B:
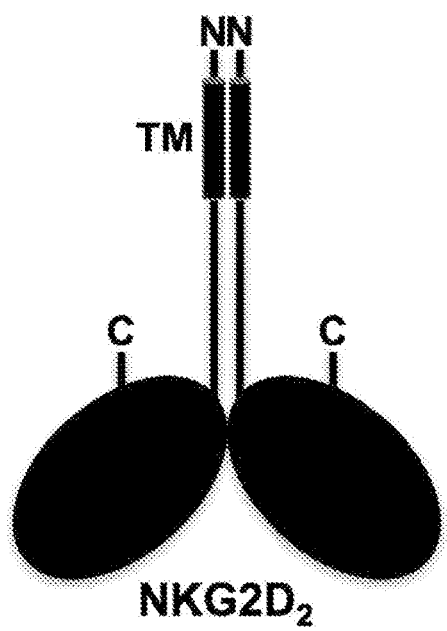
Figure 12C:
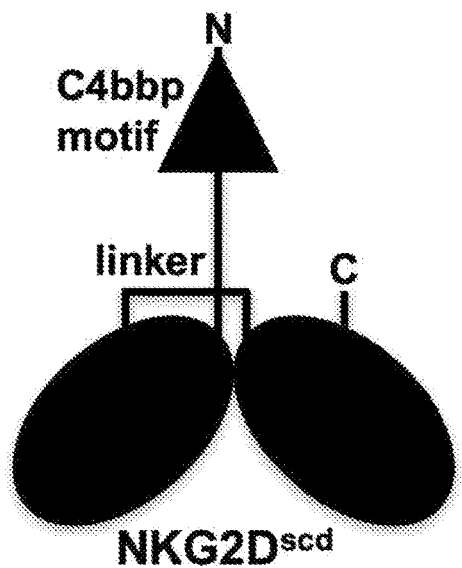
Figure 12D:
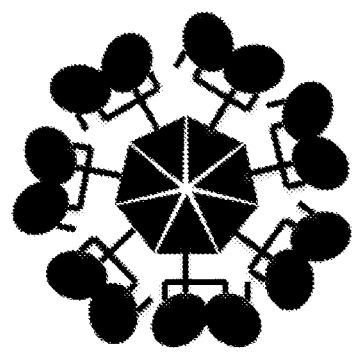
Figure 12E:
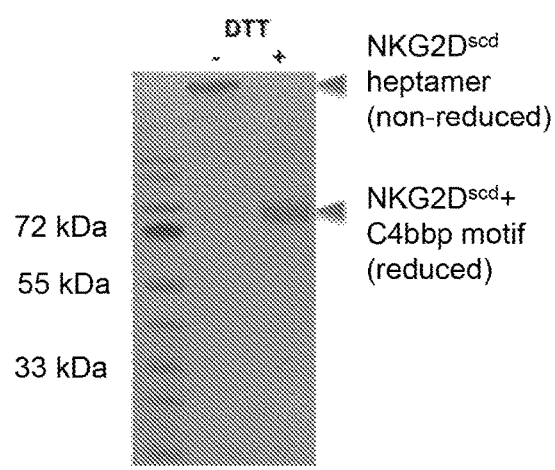
Figure 12F:
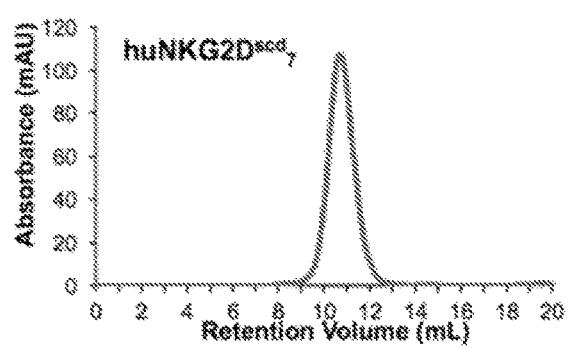
Figure 14:
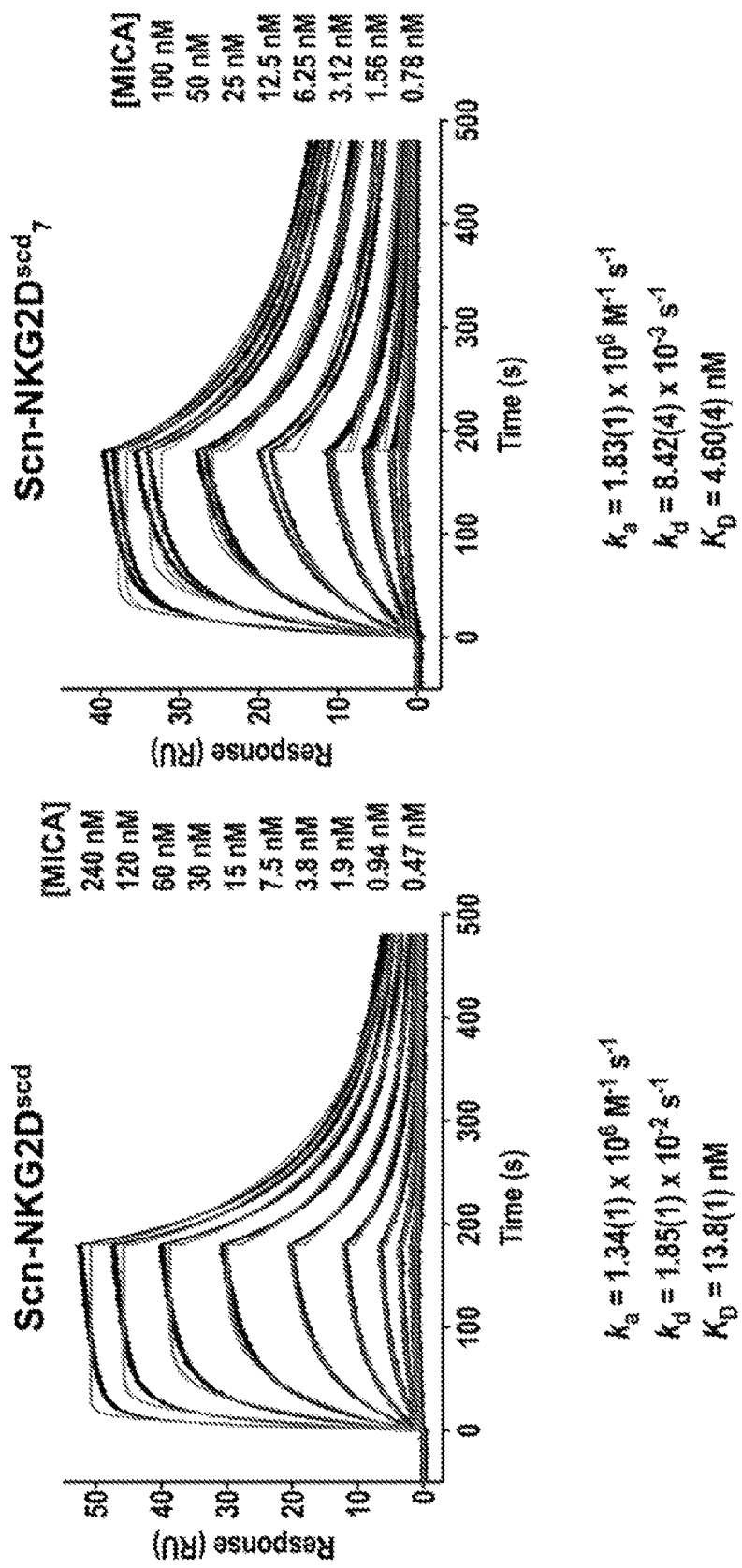
FIG. 14. SPR analysis of the binding of soluble wild-type MICA analytes to chip-coupled Scn– NKG2D$^{scd}_7$ (left) and Scn– NKG2D$^{scd}_7$ (right). Duplicate SPR response curves are shown in black, with overlaid kinetic fits. Analyte concentrations are listed to the right of each graph. Estimated binding constants are listed below each graph.
Figure 15A:
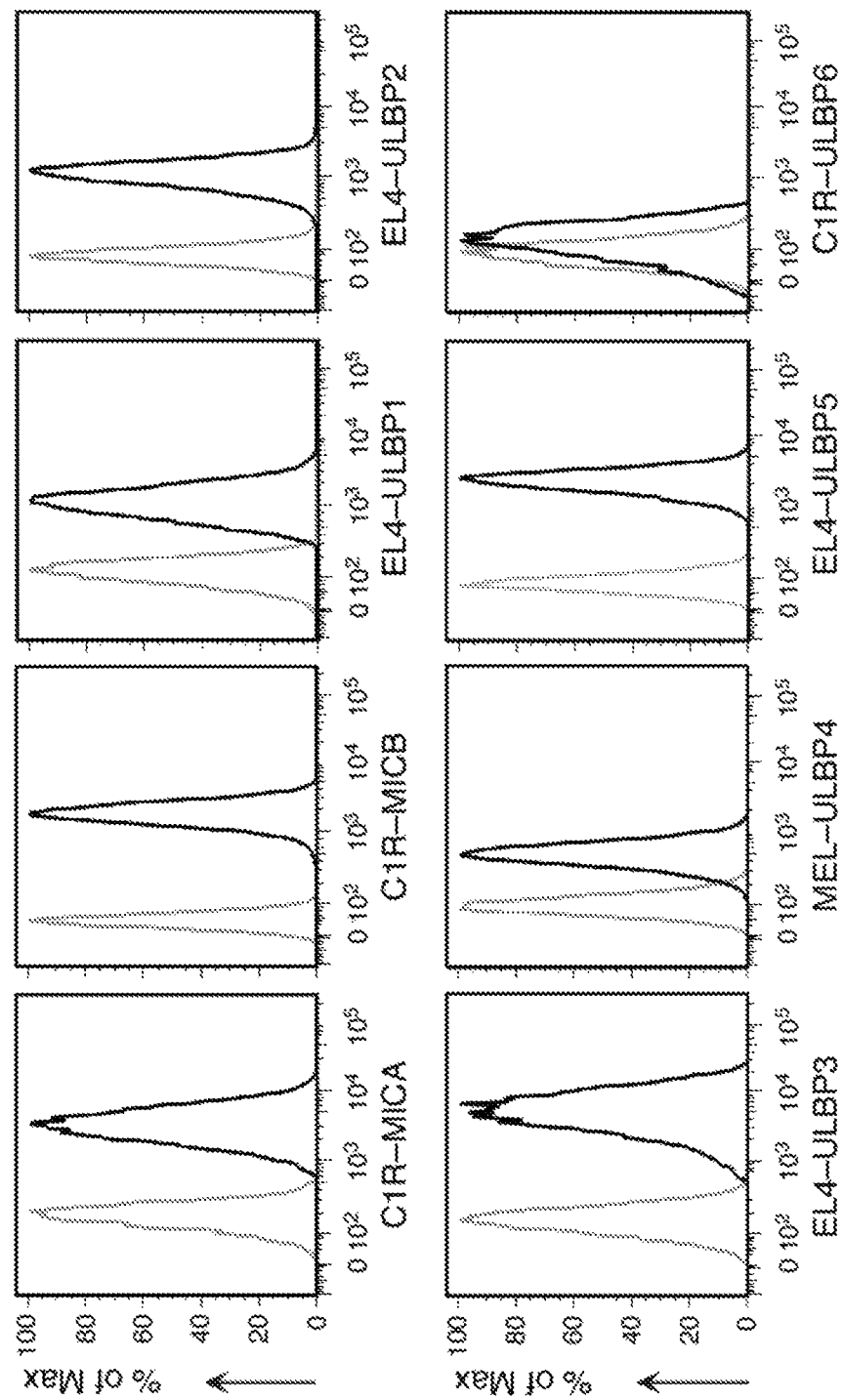
FIGS. 15A, 15B. Functional characterization of NKG2D$^{scd}_7$.
Figure 15B:
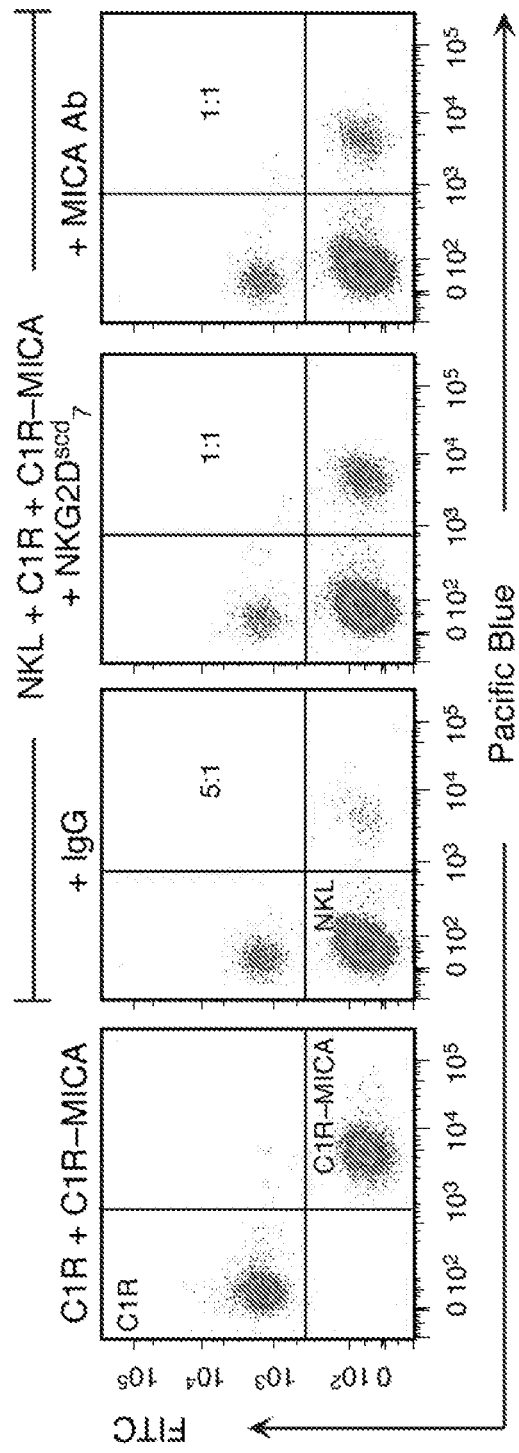

Blockade of tumor initiation by pan ligand-reactive NKG2D-based multimer. Cancers express diverse combinations of NKG2DL with variability between tumors (Groh et al., Proc Natl Acad Sci USA 1999; 96(12):6879-84, Groh et al., Proc Natl Acad Sci USA 1999; 96(12):6879-84, Li et al., Cancer Immunol Immunother 2009; 58(5):641-52). Confirmation of NKG2DL involvement in NKG2D-driven tumor initiation thus required an all-inclusive ligand masking approach. With pan-reactive Abs unavailable, a soluble form of NKG2D suitable for global ligand binding (FIG. 12; FIG. 13) was developed. To stabilize folding, the native NKG2D homodimer was reengineered as a single-chain unit (NKG2D$^{scd}$), analogous to an Ab single-chain Fv construct (FIGS. 12A-12C). To enable tight binding, avidity was seven-fold increased by fusing a multimerization domain to the NKG2D$^{scd}$ (FIGS. 12C, 12D). Solution biochemistry ascertained proper folding of the heptamerized single-chain reagent (NKG2D$^{scd}_7$; FIGS. 12E, 12F). Functionality of NKG2D$^{scd}_7$ was initially confirmed by SPR binding analyses (FIG. 14). Binding of NKG2D$^{scd}_7$ to all human NKG2DL was confirmed using individual transfectants and flow cytometry (FIG. 15A). Moreover, in a cytotoxicity assay, NKG2D$^{scd}_7$ but not solvent control interfered with lysis of NKG2DL expressing target cells by the NKG2D$^+$ NKL NK cell line (FIG. 15B; Kim et al., J Immunol Methods 2007; 325(1-2):51-66). In sphere forming assays, NKG2D$^{scd}_7$ inhibited sphere formation by ex vivo NKG2D$^+$ ovarian cancer or MDAH-2774-TF cells (FIGS. 16A, 16B).

Thereafter, NKG2D$^{scd}_7$ was used for testing of an involvement of NKG2DL in tumor initiation by ex vivo NKG2D$^+$ ovarian cancer cells. Administrations (either locally at cell inoculation sites or systemically) prevented or reduced tumor formation, thus formally linking NKG2DL engagement and NKG2D stimulation to the tumor-initiating capacity of NKG2D$^+$ ovarian cancer cells (FIG. 16C). To assess the relative contribution of NKG2D to overall tumor initiation capacity, NSG mice were engrafted with unsorted EOC cells and NKG2D stimulation disabled by NKG2D RNAi transduction or NKG2D$^{scd}_7$-mediated ligand masking. Unlike the controls, none of the experimental implants generated tumors, suggesting a prominent role of NKG2D and its ligands in EOC tumorigenicity (FIG. 16D).

Discussion Expression of cell surface receptors encoded within the human NK gene complex is typically restricted to cells of hematopoietic origin. An exception is NKG2D, which, in addition to its normal distribution on CD8 T cells and NK cells, is also found on variable proportions of cancer cells in diverse types of epithelial malignancies. Previous in vitro studies and correlative clinical observations have provided preliminary evidence for a role of cancer cell NKG2D in high plasticity reprogramming but its full oncogenic potential has remained unknown. It is now shown that NKG2D$^+$ ovarian cancer cells have the capacity for self-renewing sphere formation and efficient tumor initiation upon implantation into immunodeficient mice. Without being bound by mechanism, formal evidence that ligand engagement and hence NKG2D stimulation underlie this functional capacity is provided. The described results further suggest that NKG2D-driven tumor initiation accounts for a significant portion of the overall tumor initiation potential of a given ovarian cancer. The cancer cell NKG2DL-NKG2D signaling axis may thus represent an important regulator of tumorigenesis and dissemination, offering an explanation for the negative clinical associations found between frequencies of NKG2D$^+$ cancer cells or abundance of NKG2DL expression and disease outcome (see FIG. 3; McGilvray et al., Int J Cancer 2010; 127(6):1412-20, Wu et al., J Clin Invest 2004; 114(4):560-8, Cancer Immunol Immunother 2009; 58(5):641-52, Duan et al., Med Oncol 2011; 28(2):466-74, Fang et al., J Exp Clin Cancer Res 2014; 33:76). The tumor initiating role of NKG2D applies to malignancies other than ovarian cancer studied here, such as any cancer harboring NKG2D$^+$ cells (e.g., breast, colon, prostate, etc; see Benitez et al., supra, Guilloton et al., Leukemia 2005; 19(12):2206-14, Tang et al., Immunologic research 2016; 64(3):754-64).

Example 3

Enhancement of Vaccine Response. The memory CD8 T cell compartment can be activated by inflammatory cues even in the absence of a T cell receptor signal. This process is referred to as bystander-activation of memory T cells and has been observed following different infections. The contribution of these cells to host immunity was poorly understood until it was recently reported that bystander-activated memory CD8 T cells play a crucial role in controlling early pathogen replication following infection. It was demonstrated that bystander-activated memory CD8 T cells express granzyme B and can directly kill target cells in a TCR-independent, innate-like fashion. In stark contrast to their beneficial effect for host immunity following infection, recent data provides strong evidence that these bystander-activated T cells decrease antigen availability following vaccination by eliminating antigen-presenting cells.

NKG2D as a key molecule in this process and NKG2D decoys disclosed herein can be used as an antagonist to enhance vaccine efficacy by inhibiting bystander-activated CD8 T cell function. Without being bound by theory, following vaccination, bystander-activated memory T cells eliminate dendritic cells that present antigen and thereby decrease antigen availability and diminish primary adaptive immune responses. By inhibiting this innate-like function of memory CD8 T cells, vaccine efficacy is enhanced by preserving antigen-presenting cells.

Data described herein shows that inhibiting NKG2D-NKG2DL interactions increases the number of antigen-presenting dendritic cells and the ensuing CD4 and CD8 T cell response. Considering the limited frequency of memory phenotype cells in 8 wk old, SPF-housed B6 mice compared to a human T cell compartment, a much greater effect of bystander-activation on subsequent immune responses is predicted. Data is presented demonstrating that primary human influenza-specific CD8 T cells become bystander-activated. Interestingly, some CMV (pp65)-specific T cells already almost uniformly express granzyme B, a feature they share with human Natural Killer (NK) cells (while mouse NK cells do not express granzyme B ex vivo).

Acquisition of innate-like effector function in the absence of cognate TCR signals. An experimental system with defined TCR specificity was first used to determine BA-CTL phenotype and function. Memory T cells were generated by transferring low numbers of congenically marked, naïve OT-I T cells into B6 mice. OT-I cells recognize the SIINFEKL (N4) epitope of chicken ovalbumin (OVA). Mice were infected with a recombinant strain of vesicular stomatitis virus (VSV-OVA) to prime OT-I T cells. 30 days after the VSV-OVA infection, mice were infected with wild-type *Listeria monocytogenes* (VVT-LM), which does not express any antigen with agonist properties for OT-I T cells (i.e., does not prime naïve OT-I T cells) to induce bystander-activation (FIG. 17A). The majority of resting memory OT-I T cells expressed NKG2D, but not granzyme B before the VVT-LM challenge (day 0, FIGS. 17A and 17B—this time point is 30 days after the VSV-OVA infection). Half of the OT-I memory cells expressed granzyme B on day 3 after the VVT-LM infection thus displaying a BA-CTL phenotype (FIG. 17B), but this percentage decreased on day 5 post VVT-LM infection suggesting that BA-CTL function is temporary and wanes by the time the primary effector response becomes robust. There was no significant change in the frequency of OT-I T cells (data not shown) before and after the VVT-LM infection. Finally, the location of memory OT-I T cells were interrogated before (FIG. 17E) and after (FIG. 17F) bystander-activation. Bystander-activation changes the OT-I T cell distribution from uniformly distributed to clustered, which very closely resembles the clusters formed in a primary antigen-specific T cell response (FIG. 17D). It was found that these clusters are co-localized with

*Listeria*-infected cells (data not shown) suggesting that bystander-activated cells migrate to and cluster at the site of infection.

Figure 18A:
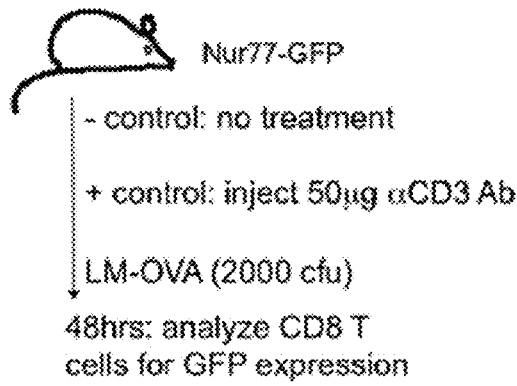
FIGS. 18A-18C.
Figure 18B:
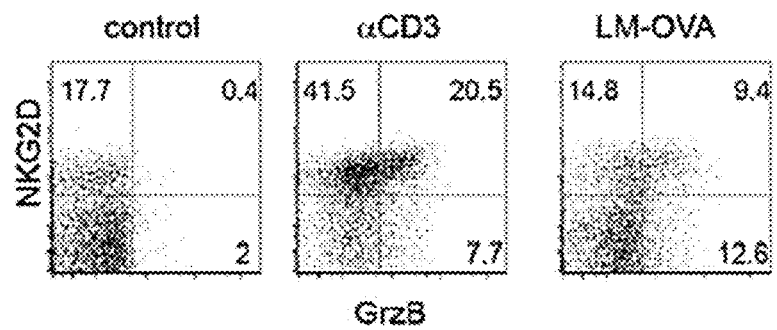

The respective roles of the TCR and cytokines in bystander-activation. It was considered whether generation of BA-CTLs could (a) be completely independent of TCR signals, (b) depend on a basal signal (TCR tickling) or (c) depend on stronger than basal signals, possibly provided by cross-reactivity of the activated T cell to available antigen at any point of the activation process (Dontu et al., *Genes Dev* 2003; 17(10):1253-70). BA-CTLs may not necessarily be a homogeneous population and could be composed of some cells that are purely inflammation-activated and others that have cross-reactivity and are activated by TCR signals. To address these possibilities the recently described Nur77-GFP reporter mice (Moran et al. *J. Exp. Med.* 2011; 208:1279-89), in which the GFP expression level in T cells is directly proportional to the strength of the TCR stimulus a T cell receives and, importantly, independent of inflammatory signals were used. This was specifically shown in the context of an LM infection. Most importantly, the Nur77-GFP system is sensitive enough that it reports even very weak TCR signals. To establish the baseline and maximum GFP signal, one group of mice remained untreated and another group received an injection of aCD3 antibody as a positive control for TCR signaling (FIGS. 18A, 18B). naïve Nur77-GFP mice were directly infected with LM-OVA and determined GFP expression levels in the CD44hi NKG2D$^+$ granzyme B$^+$ population 48 hours after the infection (FIG. 18C).

Figure 18C:
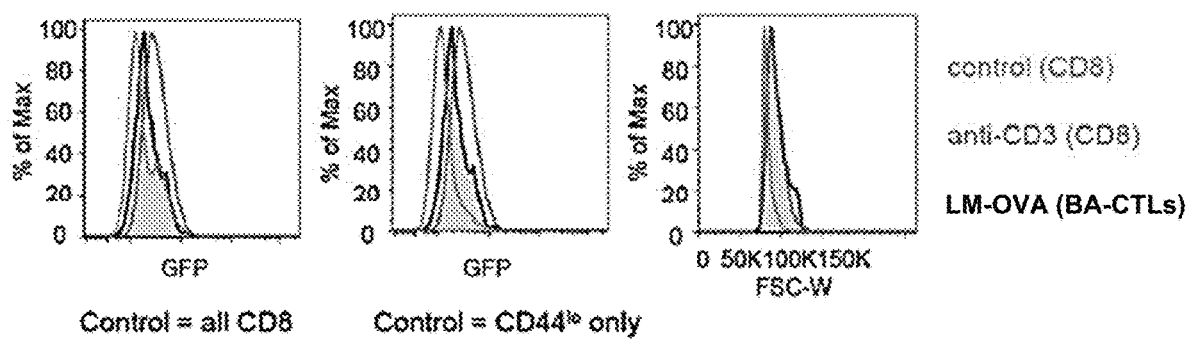

CD44hi NKG2D$^+$ granzyme B$^+$ CD8 T cells in the LM-OVA infected group displayed GFP expression levels higher than CD44lo CD8 T cells, but congruent with the expression levels of the overall CD44lo+hi CD8 control population (black vs. gray lines, FIG. 18C, left and middle panel). BA-CTLs with the brightest GFP signal did not reach the level of GFP expression in the aCD3 treated group (black vs. gray lines, FIG. 18C). It is noteworthy that BA-CTLs and CD8 T cells from the aCD3 treated group were blasting and significantly bigger in size than the baseline control population (FIG. 18C, right panel). The data show that BA-CTLs do not receive TCR stimuli above the threshold of memory phenotype CD8 T cells in an uninfected animal. Together these data suggest that BA-CTLs only receive basal TCR signals during activation.

It was next examined whether exposure to IL-12, IL-15 and IL-18 could directly induce granzyme expression and affect NKG2D expression in naïve and memory phenotype OT-I T cells. Robust granzyme expression in the memory phenotype population (CD44high), but not naïve CD8 T cell population after 24 hours of incubation with IL-12/15/18 (data not shown and 11) was found. Recent work describes a key role for monocytes and DCs in mediating bystander activation of memory CD8 T cells (Soudja et al., *Immunity* 2012; 37:549-62). Importantly, all three of these cytokines are expressed early after an infection, which is at least to some extent due to availability of preformed mRNA.

Figure 17A:
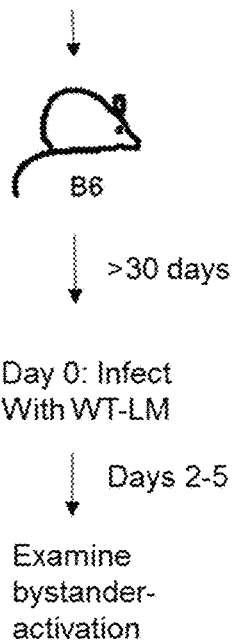
FIGS. 17A-17F. Memory OT-I T cells temporarily become BA-CTLs and cluster during bystander-activation.
Figure 17B:
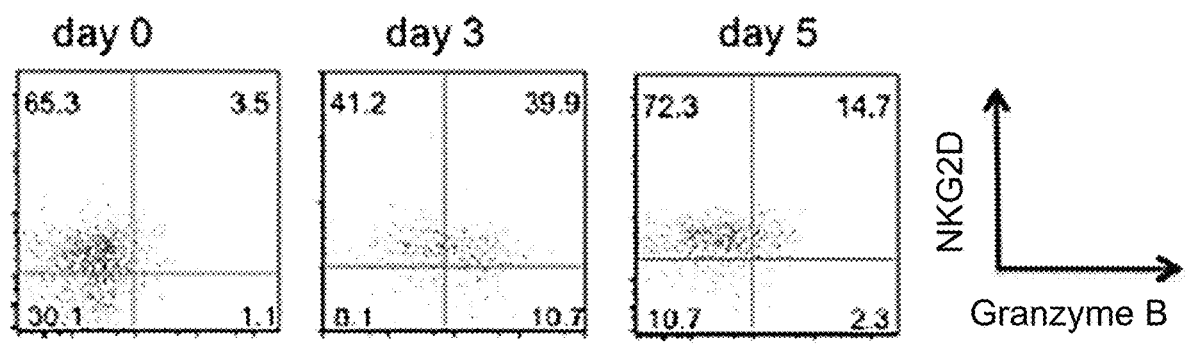
Figure 17C:
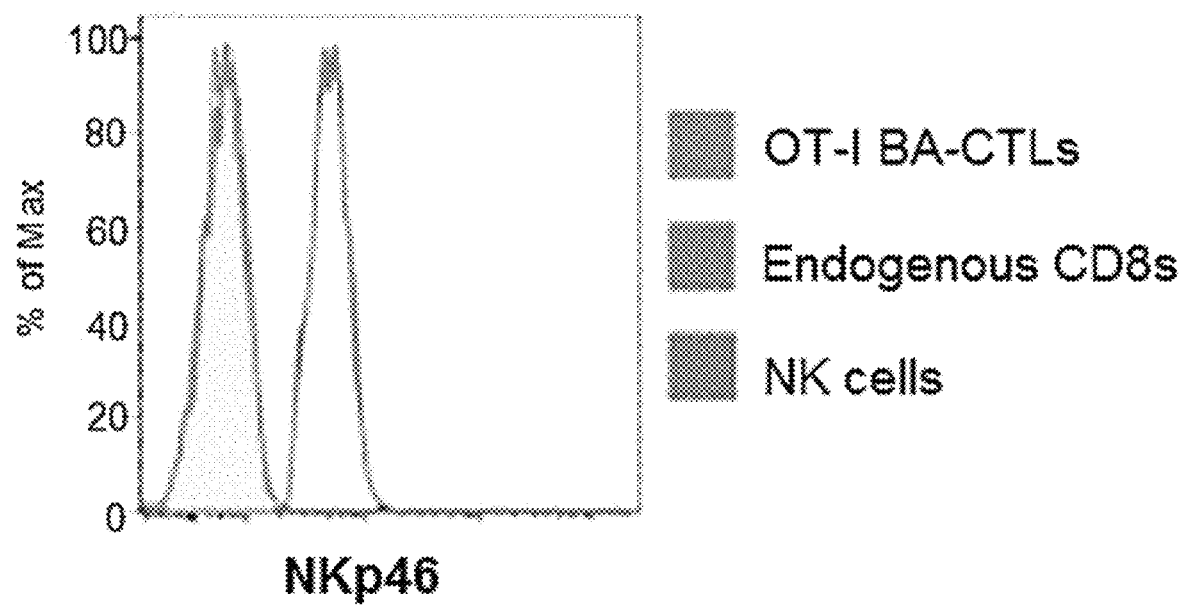
Figure 17D:
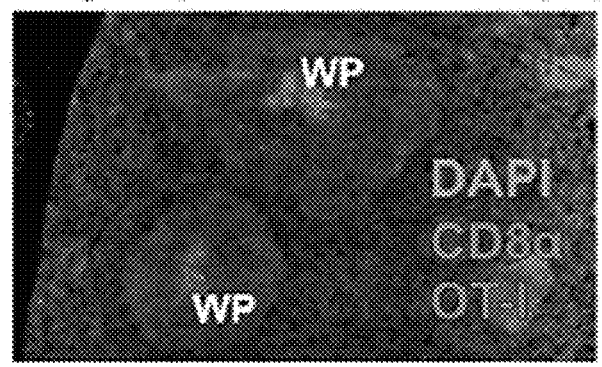
Figure 17E:
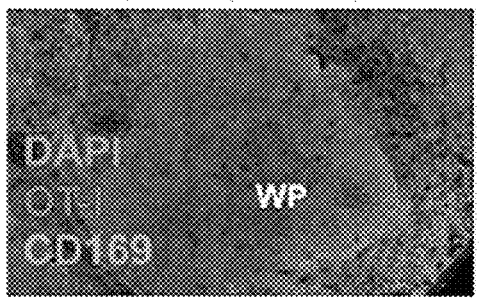
Figure 17F:
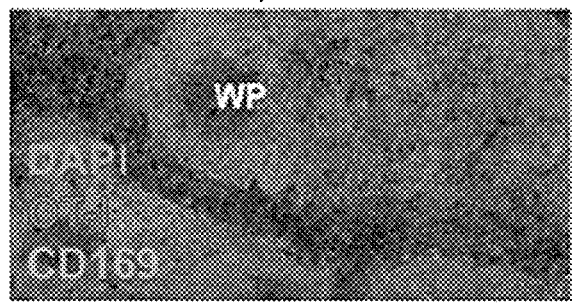
Figure 19A:
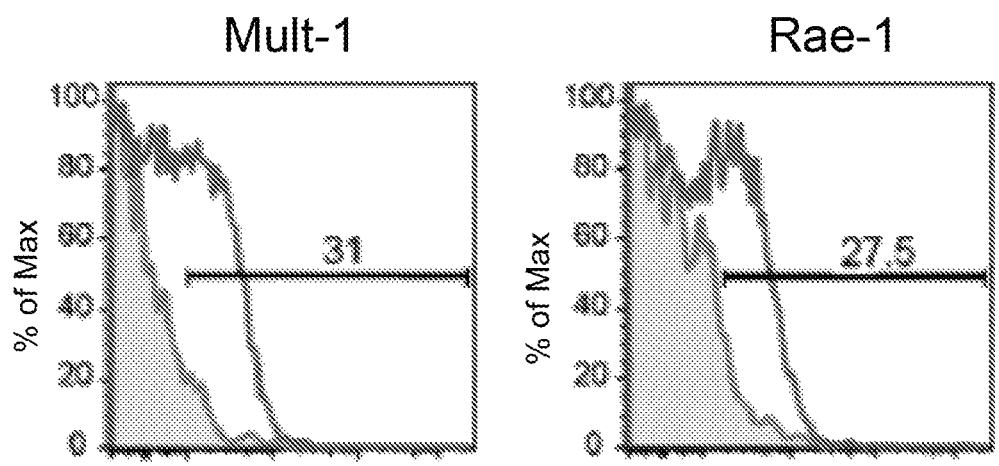
FIGS. 19A, 19B. Expression of NKG2DL on target cells following infection and direct killing by BA-CTLs. Immunization with an attenuated pathogen leads to acquisition of NKG2DL expression on APCs and elimination of NKG2DL-expressing target cells.
Figure 19B:
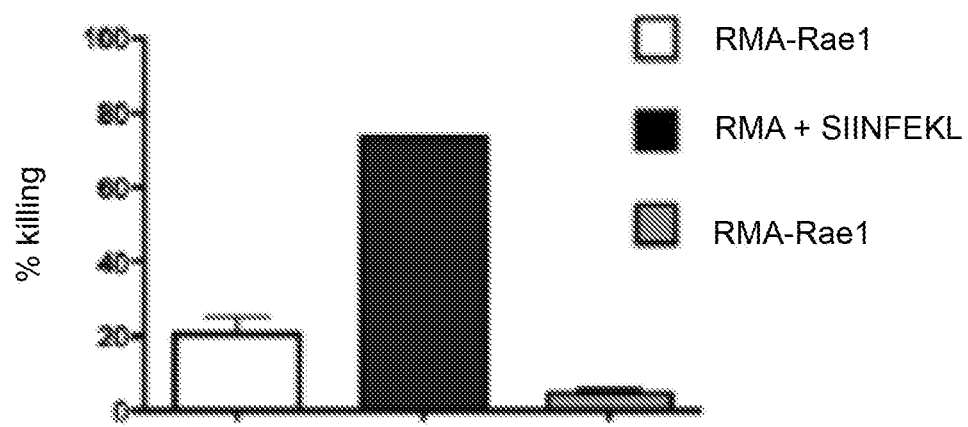

Identifying the target cells. Bystander-activated cells were phenotyped for expression of receptors associated with NK cell activation. NK cells have been shown to have similarities with CD8 memory T cells in phenotype, function and gene expression patterns and expression of inhibitory and activating NK cell receptors has been reported on CD8 T cell populations. BA-CTLs expressed NKG2D (FIGS. 17B, 18B), but did not express the NK lineage-specific receptor NKp46 or the inhibitory receptors Ly49F/I/C/H at any given time (FIG. 17C and data not shown). These data further support the notion that that BA-CTL function is temporary (FIG. 17B) and argues against the possibility that BA-CTLs are differentiating into NK-like cells as reported during pathologic exposure to high levels of IL-15 45. NKG2D was initially cloned and identified as an activating receptor on Natural Killer (NK) cells (Dissen et al., *J. Exp. Med.* 1996; 183:2197-207; Vance et al., *European Journal of Immunology* 1997; 27:3236-41; Ho et al., *Proc. Natl. Acad. Sci. USA* 1998; 95:6320-5; Wu et al., *Science* 1999; 285:730-2), but is also expressed on CD8 effector cells (Wu et al., *Science* 1999; 285:730-2; Bauer et al., *Science* 1999; 285:727-9), where it can function as a costimulatory molecule (Groh et al., *Nature Immunology* 2001; 2:255-60). Its MHC class I-like ligands (the Rae-1 family, H60 and Mult-1 in the mouse and MICA, MICB and the ULBP family in humans (Zafirova et al., *Cellular and Molecular Life Sciences: CMLS* 2011; 68:3519-29)) are expressed following DNA damage (Wu et al., *Science* 1999; 285:730-2; Bauer et al., *Science* 1999; 285:727-9; Gasser et al., *Nature* 2005; 436:1186-90), on certain tumor cells (Wu et al., *Science* 1999; 285:730-2; Bauer et al., *Science* 1999; 285:727-9; Nausch et al., *Oncogene* 2008; 27:5944-58) and on infected and Toll-like receptor (TLR) activated cells (Hamerman et al., *J. Immunol.* 2004; 172:2001-5; Kloss et al., *J. Immunol.* 2008; 181:6711-9). To address if NKG2DL are expressed following an LM infection, mice were infected with 1×10$^7$ cfu actA$^-$ LM-OVA and determined Rae1 and Mult-1 expression 24 hours later. Substantial upregulation of both ligands on CD11c$^+$ I-Ab$^+$ cells in the spleen (FIG. 19A), which are the predominantly infected cells early after infection with LM55 were found. To determine if BA-CTLs can directly lyse NKG2DL expressing target cells, the VITAL in vitro killing assay (Chu et al., *Cell Reports* 2013; 3:701-8) was used. It was found that OT-I BA-CTLs could kill RMA-Rae1 expressing cells (but not RMA cells), albeit less efficiently than SIINFEKL pulsed RMA cells (FIG. 19B). BA-CTL mediated killing of RMA-Rae1 expressing cells is blocked with αNKG2D antibody (data not shown). These data show that BA-CTLs can directly kill target cells in an NKG2D-dependent manner. Higher killing efficiency was observed when the TCR was engaged.

Figure 20A:
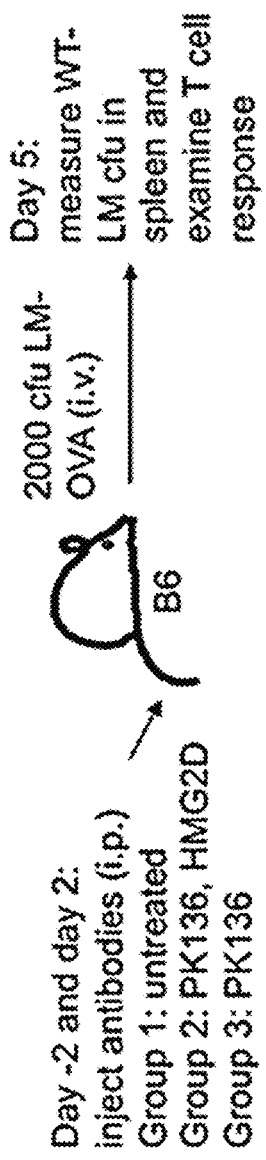
FIGS. 20A-20C. BA-CTL limit early pathogen replication.
Figure 20C:
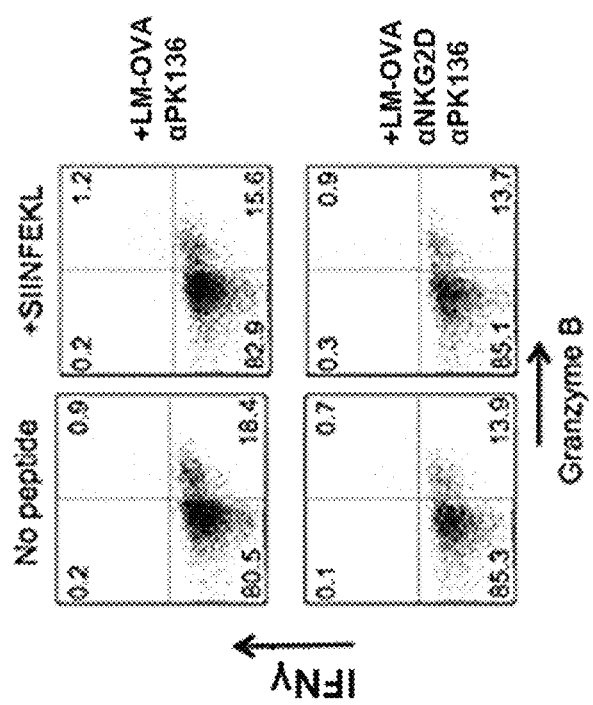
Figure 20B:
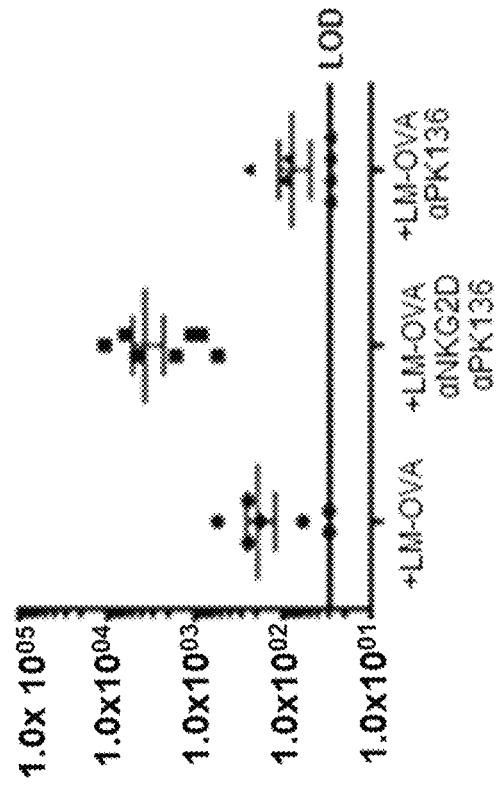

Providing early protection—a crucial role for BA-CTLs. To provide evidence that this BA-CTL-mediated, innate-like killing could occur in vivo, it was asked whether blocking NKG2D on BA-CTLs affects the course of an LM infection. An NKG2D-blocking antibody (Ito et al., *International Immunology* 2008; 20:1343-9) was administered 2 days before and after infecting mice with LM. Mice were also injected with depleting αNK1.1 antibody (clone PK136)57 to eliminate skewing of the results by NK and NKT cells, which can express NKG2D as well (FIG. 20A). NK and NKT cell depletion was confirmed by FACS analysis (data not shown). There was no significant difference in bacterial counts on day 3 post-infection (data not shown) excluding an effect on very early, innate immunity, but a 10-fold increase in bacterial counts on day 5 after infection in αNKG2D antibody treated mice (FIG. 20B). αNKG2D administration did not impair granzyme expression of BA-CTLs (FIG. 20C), suggesting that NKG2D signaling is not required for BA-CTL induction per se. To ensure that the increase in bacterial load was not due to an effect on the primary CD8 T cell response, size, phenotype and function of antigen-specific CD8 T cells in independent follow-up experiments were determined by measuring the response of adoptively transferred OT-I T cells. While αNKG2D antibody treatment did not affect the size (FIG. 21A) or function (FIG. 21B) of the OT-I T cell response on day 5 after infection, αNKG2D antibody treated animals again had significantly higher titers than animals from the two control groups (FIG. 21C; middle panel). Transferring $1\times10^4$ OT-I T cells prior to infection led to the generation of a sizeable effector population on day 5 and these mice had significantly lower bacterial counts compared to untransferred, infected B6 mice (compare FIG. 20B and FIG. 21C). These data show that a 100-fold increase in the precursory frequency (from 100 endogenous CD8 responders 58 to $1\times10^4$ OT-I T cells) and the ensuing accelerated generation of a large pool of effector cells Badovinac et al., *Immunity* 2007; 26:827-41; Marzo et al., *Nature Immunology* 2005; 6:793-9) did lower the bacterial burden. Importantly, a significant impact on bacterial clearance by BA-CTLs was still observed in all three experimental groups (FIG. 21C, middle panel).

These data show that—in the context of an infection—the primary response is unaffected (in size and function) by treatment with NKG2D blocking antibody and thus not responsible for the difference in bacterial clearance in the experimental groups. Since mice were NK and NKT cell depleted, the data strongly support the notion that BA-CTLs are a key mediator of NKG2D-dependent, early bacterial clearance. A potential effect of γ/δ T cells in LM clearance was also excluded using TCR $\delta^{-/-}$ animals in follow-up experiments (data not shown).

Figure 22A:
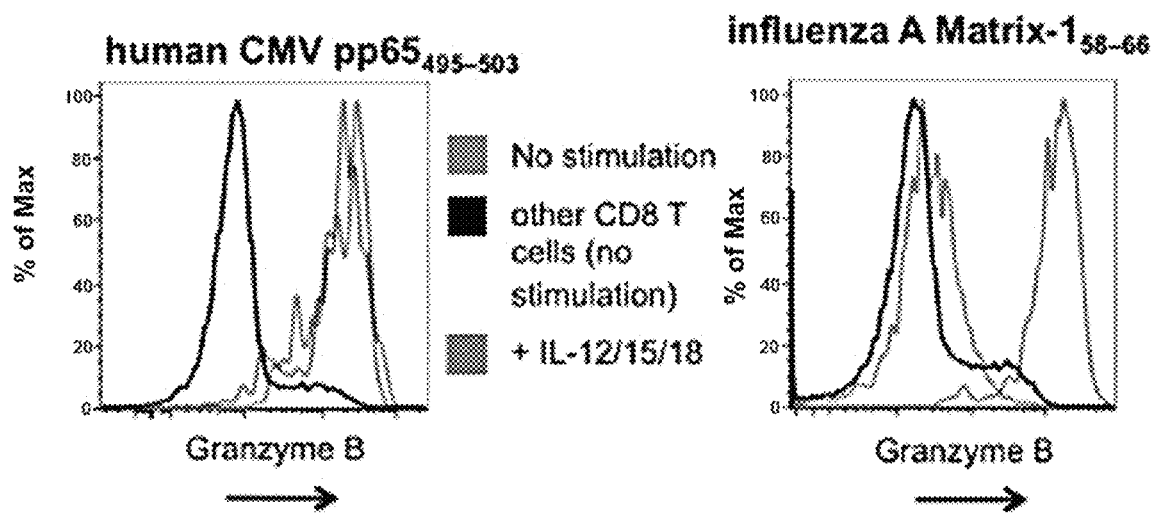
FIGS. 22A-22C. Functional and transcriptional analysis of primary human memory T cells.
Figure 22B:
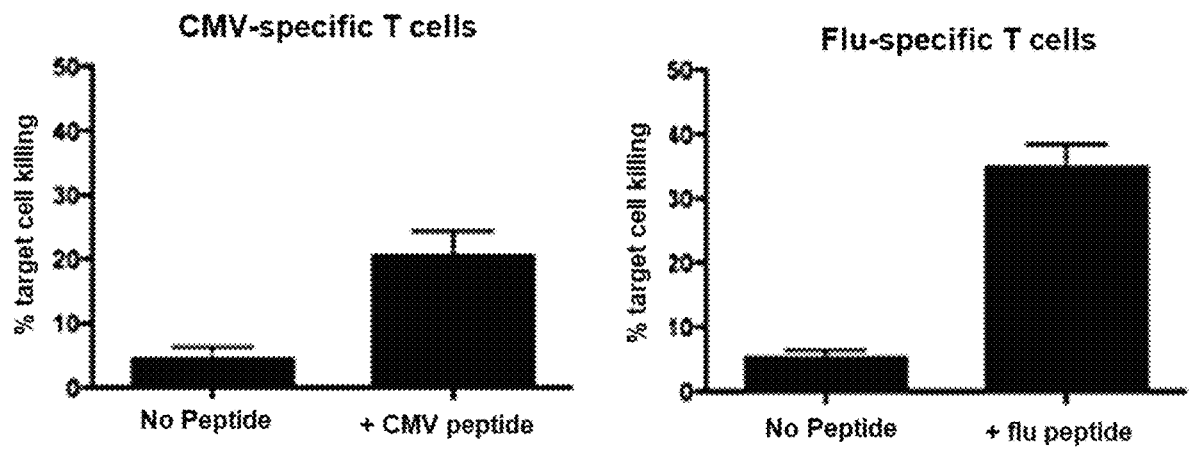
Figure 22C:
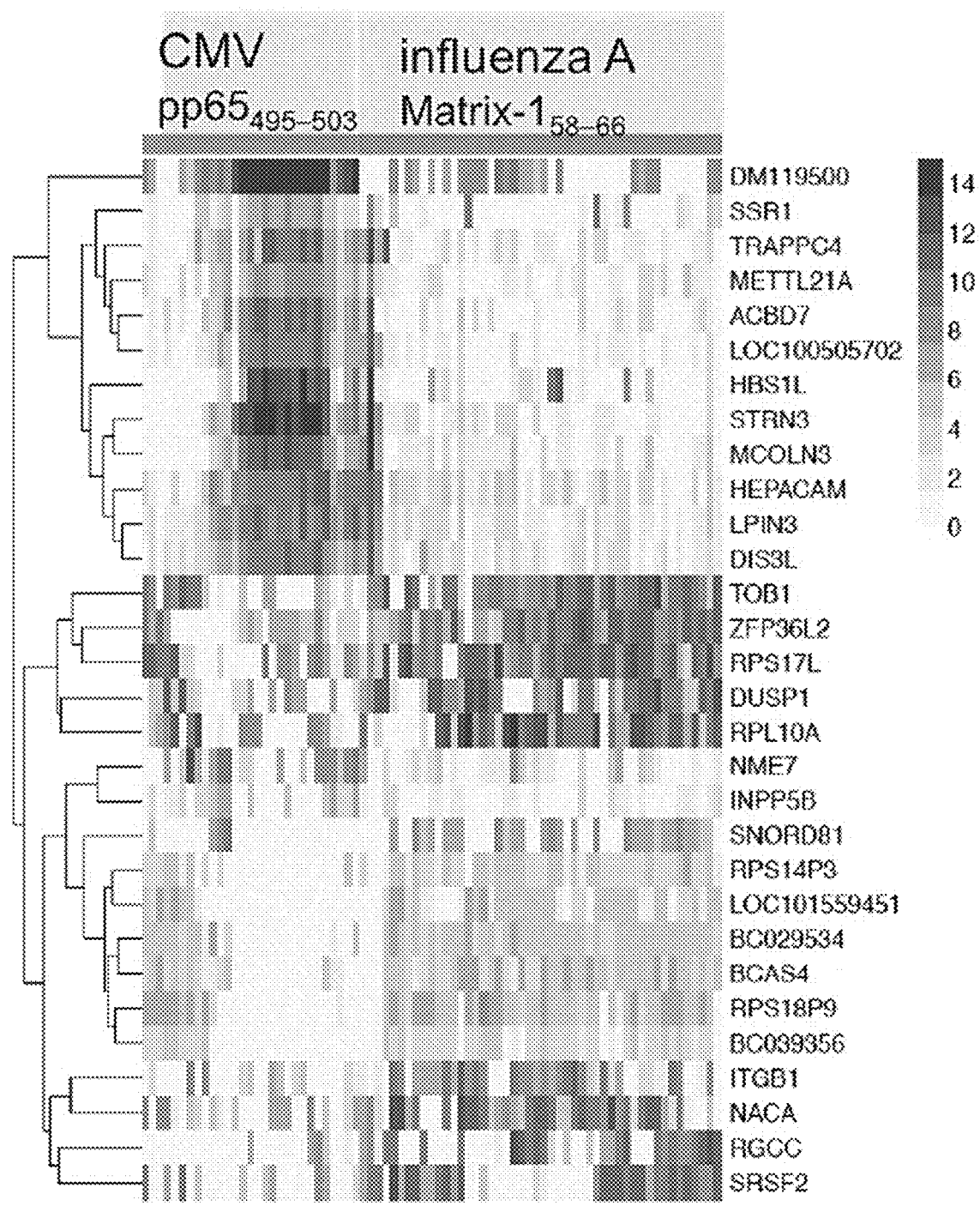

Moving from a mechanistic mouse model system to examining bystander activation in different human CD8 T populations. Many important mechanistic aspects and consequences of bystander-activation can only be addressed in a well-defined experimental system such as the mouse model system. Several pieces of strong evidence argue that bystander-activation is not just a "mouse phenomenon", but actually very similar to bystander-activation in human memory T cells. Following in vitro stimulation NKG2D-dependent, TCR-independent killing of NKG2DL expressing target cells has been demonstrated for human CD8 T cells with an effector memory phenotype in vitro, although its biological significance was not clear (Verneris et al., *Blood* 2004; 103:3065-72). Bystander-activation of memory CD8 T cells has been demonstrated to occur in humans following EBV infection. Influenza-specific CD8 T cells transiently express granzyme during the acute phase of a primary EBV infection in a cohort of college students (Odumade et al., *J. Exp. Med.* 2012; 209:471-8). The authors showed that this was not due to epitope cross-reactivity and influenza-specific CD8 T cells lost granzyme expression after the acute EBV infection phase. To examine if the same mechanisms induce bystander-activation in mouse and human memory T cells, the effect of incubating human PBMCs with IL-12/15/18 for 24 hours was tested. Similar to what has been observed with mouse CD8 T cells before, memory phenotype (CD45RO+) CD28+ CD8 T cells increase their cytotoxic potential (data not shown). The ability of influenza- and CMV-specific T cells to become bystander-activated (FIG. 22A) were specifically interrogated. Influenza-specific memory T cells were granzyme B-ex vivo and IL-12/15/18 treatment was sufficient to induce granzyme B expression. A substantial fraction of the CMV-specific effector memory phenotype CD8 T cells expresses granzyme B directly ex vivo and this was not substantially enhanced by cytokine stimulation, although other granzyme+ effector memory phenotype CD8 T cells increased granzyme expression (data not shown). Both influenza-specific and CMV-specific T cells kill antigen-presenting cells ex vivo (FIG. 22B). This demonstrates that both memory subsets have intact killing function and there is the technical ability to perform these assays with primary, cryopreserved human T cells. When treated with IL-12/15/18, killing was increased in both T cell populations suggesting that both subsets respond to IL-12/15/18 (data not shown). Finally, the heterogeneity of both memory populations on a single-cell transcriptome level was evaluated using the C1 Fluidigm System (FIG. 22C). Importantly, for this experiment flu- and CMV-specific T cells were isolated from the same donor to rule out environmental and genetic differences as factors contributing to transcriptome differences. Although significant differences in gene expression between these two memory subsets were found, the heterogeneity within the population was surprisingly small (FIG. 22C, each single cell is one column). Based on these data it is expected that an antigen-specific memory population will respond in a homogenous manner to bystander-activation. These data also suggest that instead of a single-cell RNAseq approach a more cost-effective small cell number RNAseq approach (1000 cells) will be sufficient for transcriptomics analysis.

Bystander-activated CD8 memory phenotype T cells (BA-CTLs) affect vaccine efficacy. Background and Performed Studies: Shortening the duration of antigen presentation reduces the magnitude of the CD8 T cell response. The relevance of the duration of TCR engagement in dictating the magnitude and function of the antigen-specific CD8 T cell response has been addressed (Prlic et al., *J. Exp. Med.* 2006; 203:2135-43). Antigen was delivered through peptide pulsed DCs carrying a transgene encoding the diphtheria toxin receptor (DTRtg DCs). The DTRtg DCs can be efficiently removed by administration of the toxin without passing on the antigen to host APCs (and without affecting inflammation provided by an ongoing VVT-LM infection). The ability to discontinue antigen presentation within a defined time period allowed demonstration that the early interactions are sufficient to instruct the T cell for functionality, but longer contact with DCs is needed for optimal long-term proliferation and survival. Thus, the magnitude of clonal expansion, but not the functionality of the effector cells, correlated directly with the duration of antigen exposure (as long as systemic inflammation is provided). Based on these data, BA-CTL mediated elimination of APC will shorten the duration of antigen presentation and affect the size of the primary CD8 T cell response when antigen is limited.

Blocking BA-CTLs increases the antigen-specific CD8 T cell response in the context of immunization. To test the hypothesis that inhibiting BA-CTLs increases antigen availability and thus the size of the primary CD8 T cell response, mice were infected with actA⁻ LM-OVA. This strain is attenuated and cannot spread from cell to cell and thus provides a limited amount of antigen (compared to a VVT-LM infection).

Figure 23A:
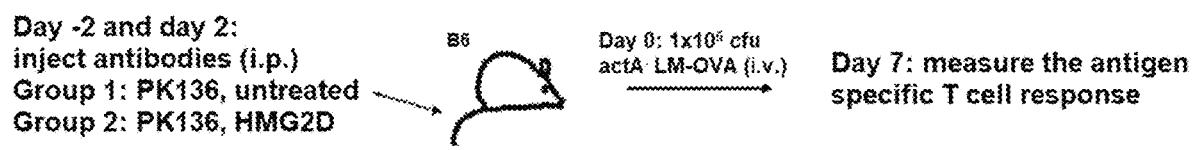
FIGS. 23A-23D. Bystander activation of memory CDB T cells dampens the antigen-specific CD4 and CDB T cell response.
Figure 23B:
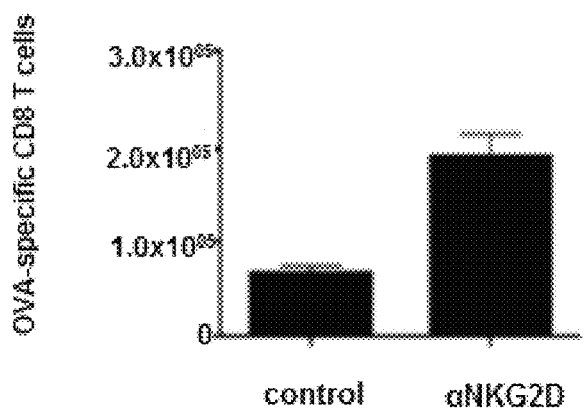
Figure 23C:
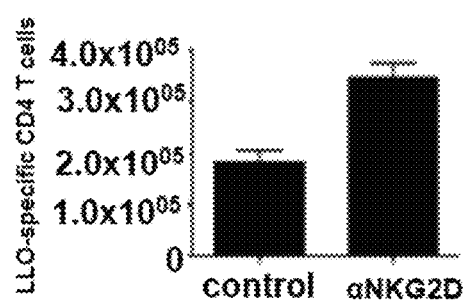
Figure 23D:
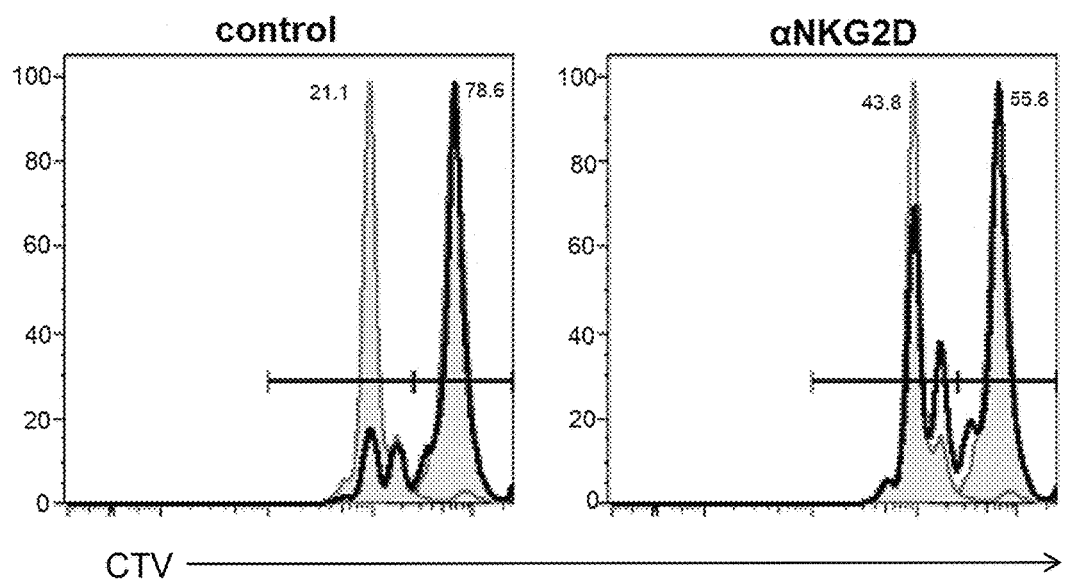
Figure 24:
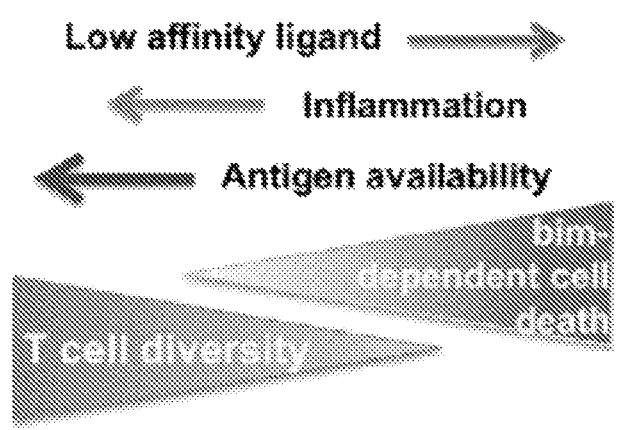
FIG. 24. TCR signal strength and inflammation dictate the magnitude of the primary response in a bim-dependent manner. Low affinity stimulated T cells are more susceptible to bim-mediated cell death, but this can be partially overcome by increasing inflammation. Increasing antigen availability in the context of inflammation can fully overcome the bim-mediated cell death and preserve low affinity T cell responses.
Figure 25A:
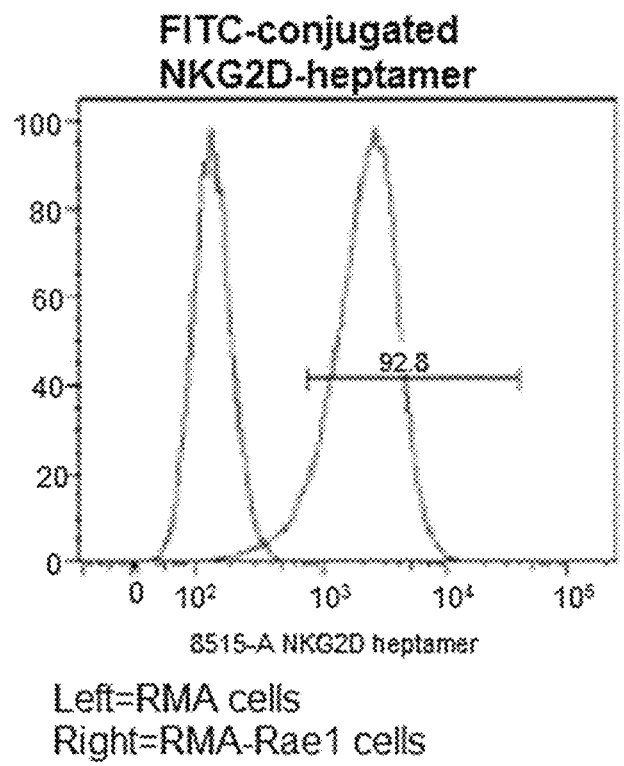
FIGS. 25A-25B. NKG2D$^{scd}{}_7$.
Figure 25B:
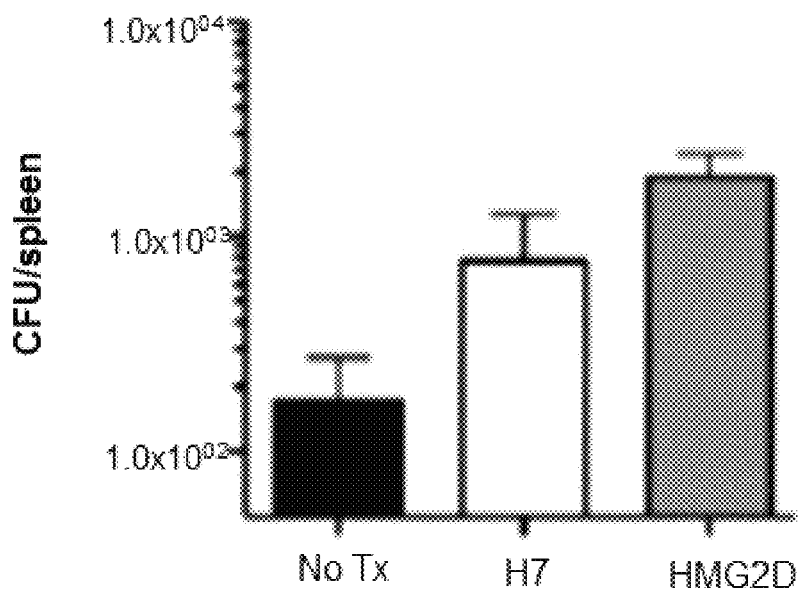
Figure 26:
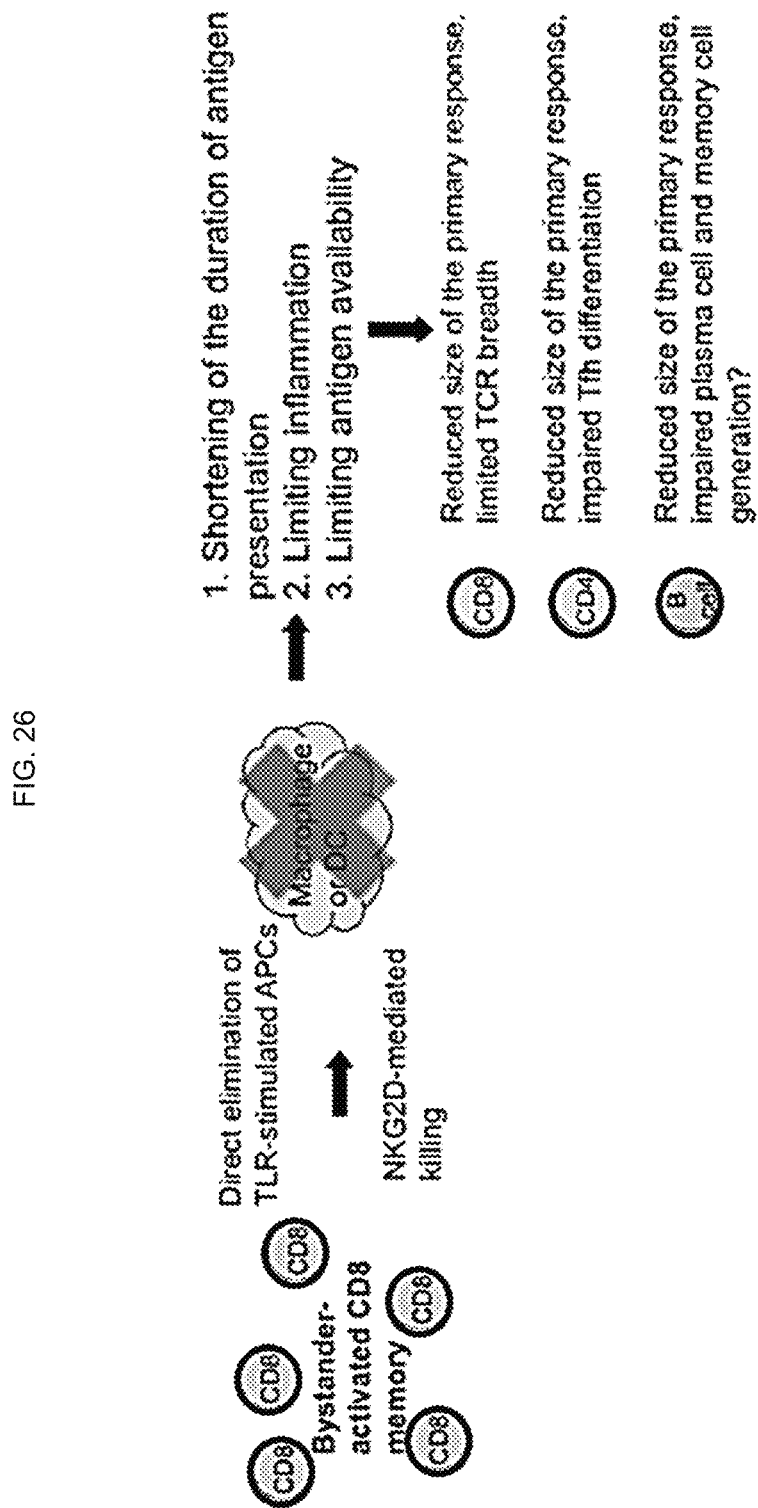
FIG. 26. BA-CTLs affect the magnitude and the quality of a vaccine induced cellular and humoral immune response. It is proposed that BA-CTLs do not simply reduce the size of the T cell and B cell response, but affect the quality of each individual component.

One group of infected mice received PK136 antibody treatment and the other group of infected mice received injections of PK136 and blocking NKG2D antibody (clone HMG2D) on days −2, 0 (=day of infection) and day 2 (FIG. 23A). The endogenous antigen-specific CD4 (to the LLO epitope) and CD8 T cell response (to the SIINFEKL epitope) was analyzed on day 7 post-priming and a significantly increased antigen-specific T cell response was found in mice that received αNKG2D antibody treatment measured by IFNγ secretion in a restimulation assay (FIGS. 23B, 23C). It was next examined if this increased T cell response in αNKG2D treated mice could be due to preservation of APCs. CD11c+ DCs were isolated 40 hours post-infection and cultured them with CTV-labeled OT-I T cells in vitro (FIG. 23D). Enhanced OT-I T cell proliferation was observed when cultured with DCs from the αNKG2D group suggesting that an increased number of DCs presented antigen in this experimental group.

The next layer of complexity—reducing inflammation and TCR signal strength. In addition to limiting the duration of antigen presentation, BA-CTL mediated elimination of APCs might also lower the amount of overall antigen availability and dampen inflammation. It is proposed that this does not only affect the magnitude of the antigen-specific T cell response, but also the breadth of the T cell response. Generating a broad memory T cell population through vaccination is beneficial to overcome pathogen epitope variability. A memory T cell pool becomes broad in TCR diversity by recruiting high and low affinity T cells. the respective roles of TCR signal strength and inflammatory signals in regulating breadth and size of the T cell response was previously addressed and it was found that that bim-mediated cell death affects the size of the effector pool through TCR signal strength- and inflammation-mediated signals, but is overcome when low affinity cells are primed in the context of a replicating pathogen. These recently published data are summarized in FIG. 24. Based on these data it is proposed that BA-CTL mediated elimination of APCs affects the size of the CD8 T cell response and its overall quality (FIG. 24). Recently, it has been demonstrated that the antigen dose impacts the differentiation process of CD4 T cells and shifts the balance between T helper 1 (Th1), T follicular helper (Tfh) and germinal center Tfh (GC-Tfh) cells (Tubo et al., *Cell* 2013; 153:785-96). This data favors a model where strong TCR signaling inhibits Th1 but favors Tfh and GC-Tfh development. This is specifically pertinent to the ensuing B cell response. Putting these data in the context of vaccination, it would suggest that BA-CTL mediated elimination of APCs could shift towards Th1 and away from Tfh cells thus impairing GC development and a potent antibody response.

Generation of an NKG2D$^{scd}_7$ to block NKG2D-ligand interactions. To explore the therapeutic potential of inhibiting NKG2D-ligand interactions an antagonist that does not target NKG2D itself was generated to prevent delivering an activating or inhibitory signal via NKG2D. As the affinity of NKG2D for its ligands is moderate, NKG2D was linked to the human C4b-binding protein heptamerization motif to engineer an NKG2D$^{scd}_7$ (FIG. 12D). Binding to NKG2DL expressing cells was confirmed (FIG. 25A) and it was found that the NKG2D$^{scd}_7$ treatment recapitulates the blocking-antibody treatment (FIG. 25B). NKG2D$^{scd}_7$ is expressed using the Daedalus system (Bandaranayake et al., supra) in the FHCRC Molecular Design & Therapeutics Core facility (endotoxin-free). No toxicity or adverse events were observed in the animals (data not shown), suggesting that the NKG2D$^{scd}_7$ treatment is a feasible and innovative strategy.

Based on described data, it is proposed that BA-CTL mediated elimination of APCs affects the quality of the cellular and humoral immune response (FIG. 26). Without being bound by theory, it is hypothesized that this occurs by limiting antigen availability and dampening inflammation as well as TCR signaling strength (by limiting antigen availability). It is important to stress that all these data are generated in a system with limited antigen availability (transferring peptide pulsed DCs or using a recombinant actA– *Listeria* strain). Thus, it is proposed that in the context of limited antigen availability BA-CTL mediated APC elimination can lead to: (1) a CD8 T cell response that is diminished in overall size, in TCR breadth and function, (2) a CD4 T cell response that is diminished in size and skewed in its function (Th1 vs. Tfh, GC-Tfh) and (3) a humoral response that is diminished in size as an indirect result of reduced Tfh, GC-Tfh availability and a direct result of limited antigen availability.

FIG. 27 shows that treatment with NKG2D$^{scd}_7$ induces a significant increase in antigen-specific T cell responses following vaccination. Animals were mock treated (group 1), treated with anti-NKG2D antibody (100 μg of HMG2D at days −2 and day 2 of vaccination, group 2) or treated with NKG2D$^{scd}_7$ (200 μg of NKG2D$^{scd}_7$ at days −2 and day 2 of vaccination, group 3). Mice in these 3 experimental groups were immunized on day 0 with $1\times10^6$ cfu of actA$^-$ LM-OVA. A negative control group (no immunization) was included (group 4). The magnitude of the antigen-specific CD8 T cell response (left panel) and CD4 T cell response (right panel) was measured 7 days after vaccination using an ex vivo peptide (SIINFEKL for CD8, LLO for CD4) stimulation assay. Data shown are pooled from three independent experiments.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in a NKG2D decoy's ability to reduce NKG2DL binding to native NKG2D in an in vitro binding assay utilizing NK cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Particular embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A single chain protein comprising the formula x-y-z, wherein x comprises a multimerization domain, y comprises a first linker derived from NKG2D, and z comprises an extracellular fragment of NKG2D comprising the formula a-b-a, wherein:
   a comprises SEQ ID NO. 79, and
   b comprises SEQ ID NO. 81 or SEQ ID NO. 82.

2. A single chain protein of claim 1, wherein x comprises SEQ ID NO. 80.

3. A single chain protein of claim 1, wherein y comprises SEQ ID NO. 81 or SEQ ID NO. 82.

4. A single chain protein of claim 1, wherein x comprises SEQ ID NO. 80 and y comprises SEQ ID NO. 81 or SEQ ID NO. 82.

5. A single chain protein of claim 1, wherein y comprises SEQ ID NO. 81 and b comprises SEQ ID NO. 82.

6. A single chain protein of claim 1, wherein x consists of the multimerization domain, y consists of the first linker derived from NKG2D, and z consists of a-b-a.

7. A single chain protein of claim 1, wherein the multimerization domain is a C4b multimerization domain.

8. A single chain protein of claim 1, wherein the multimerization domain is selected from SEQ ID NO. 7-39 and SEQ ID NO. 80.

9. A single chain protein of claim 1, wherein the multimerization domain is directly linked to the first linker derived from NKG2D.

10. A single chain protein of claim 1, wherein y excludes a Gly-Ser linker.

11. A single chain protein of claim 1, wherein the first linker is derived from human NKG2D.

12. A single chain protein of claim 1, wherein y-z comprises SEQ ID NO. 3.

13. A single chain protein of claim 1, wherein the two copies of SEQ ID NO: 79 form an NKG2D homodimer comprising the extracellular binding fragment of NKG2D.

14. A single chain protein of claim 1, wherein z excludes intracellular portions of human or murine NKG2D.

15. A single chain protein of claim 1, comprising SEQ ID NO. 78.

16. A single chain protein of claim 1, multimerized into a heptamer.

17. A single chain protein of claim 1, formulated as a pharmaceutical composition.

* * * * *

SEQUENCE LISTING

```
<160> NUMBER OF SEQ ID NOS: 83

<210> SEQ ID NO 1
<211> LENGTH: 216
<212> TYPE: PRT
<213> ORGANISM: Homo sapiens

<400> SEQUENCE: 1

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30

Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
    50                  55                  60

Ile Arg Phe Ile Ile Met Val Ala Ile Trp Ser Ala Val Phe Leu Asn
```

```
                65                  70                  75                  80
Ser Leu Phe Asn Gln Glu Val Gln Ile Pro Leu Thr Glu Ser Tyr Cys
                    85                  90                  95

Gly Pro Cys Pro Lys Asn Trp Ile Cys Tyr Lys Asn Asn Cys Tyr Gln
                100                 105                 110

Phe Phe Asp Glu Ser Lys Asn Trp Tyr Glu Ser Gln Ala Ser Cys Met
                115                 120                 125

Ser Gln Asn Ala Ser Leu Leu Lys Val Tyr Ser Lys Glu Asp Gln Asp
            130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
                180                 185                 190

Ala Ser Ser Phe Lys Gly Tyr Ile Glu Asn Cys Ser Thr Pro Asn Thr
            195                 200                 205

Tyr Ile Cys Met Gln Arg Thr Val
210                 215

<210> SEQ ID NO 2
<211> LENGTH: 219
<212> TYPE: PRT
<213> ORGANISM: Mus musculus

<400> SEQUENCE: 2

Met Ser Lys Cys His Asn Tyr Asp Leu Lys Pro Ala Lys Trp Asp Thr
1               5                   10                  15

Ser Gln Glu Gln Lys Gln Arg Leu Ala Leu Thr Thr Ser Gln Pro
            20                  25                  30

Gly Glu Asn Gly Ile Ile Arg Gly Arg Tyr Pro Ile Glu Lys Leu Lys
                35                  40                  45

Ile Ser Pro Met Phe Val Val Arg Val Leu Ala Ile Ala Leu Ala Ile
        50                  55                  60

Arg Phe Thr Leu Asn Thr Leu Met Trp Leu Ala Ile Phe Lys Glu Thr
65                  70                  75                  80

Phe Gln Pro Val Leu Cys Asn Lys Glu Val Pro Val Ser Ser Arg Glu
                85                  90                  95

Gly Tyr Cys Gly Pro Cys Pro Asn Asn Trp Ile Cys His Arg Asn Asn
                100                 105                 110

Cys Tyr Gln Phe Phe Asn Glu Glu Lys Thr Trp Asn Gln Ser Gln Ala
            115                 120                 125

Ser Cys Leu Ser Gln Asn Ser Ser Leu Leu Lys Ile Tyr Ser Lys Glu
130                 135                 140

Glu Gln Asp Phe Leu Lys Leu Val Lys Ser Tyr His Trp Met Gly Leu
145                 150                 155                 160

Val Gln Ile Pro Ala Asn Gly Ser Trp Gln Trp Glu Asp Gly Ser Ser
                165                 170                 175

Leu Ser Tyr Asn Gln Leu Thr Leu Val Glu Ile Pro Lys Gly Ser Cys
            180                 185                 190

Ala Val Tyr Gly Ser Ser Phe Lys Ala Tyr Thr Glu Asp Cys Ala Asn
            195                 200                 205

Leu Asn Thr Tyr Ile Cys Met Lys Arg Ala Val
    210                 215
```

<210> SEQ ID NO 3
<211> LENGTH: 262
<212> TYPE: PRT
<213> ORGANISM: Homo sapiens

<400> SEQUENCE: 3

Asn Gln Glu Val Gln Ile Pro Leu Thr Glu Ser Tyr Cys Gly Pro Cys
1               5                   10                  15

Pro Lys Asn Trp Ile Cys Tyr Lys Asn Asn Cys Tyr Gln Phe Phe Asp
            20                  25                  30

Glu Ser Lys Asn Trp Tyr Glu Ser Gln Ala Ser Cys Met Ser Gln Asn
        35                  40                  45

Ala Ser Leu Leu Lys Val Tyr Ser Lys Glu Asp Gln Asp Leu Leu Lys
    50                  55                  60

Leu Val Lys Ser Tyr His Trp Met Gly Leu Val His Ile Pro Thr Asn
65                  70                  75                  80

Gly Ser Trp Gln Trp Glu Asp Gly Ser Ile Leu Ser Pro Asn Leu Leu
                85                  90                  95

Thr Ile Ile Glu Met Gln Lys Gly Asp Cys Ala Leu Tyr Ala Ser Ser
            100                 105                 110

Phe Lys Gly Tyr Ile Glu Asn Cys Ser Thr Pro Asn Thr Tyr Ile Cys
        115                 120                 125

Met Gln Arg Thr Val Gln Ile Pro Leu Thr Glu Ser Tyr Cys Gly Pro
    130                 135                 140

Cys Pro Lys Asn Trp Ile Cys Tyr Lys Asn Asn Cys Tyr Gln Phe Phe
145                 150                 155                 160

Asp Glu Ser Lys Asn Trp Tyr Glu Ser Gln Ala Ser Cys Met Ser Gln
                165                 170                 175

Asn Ala Ser Leu Leu Lys Val Tyr Ser Lys Glu Asp Gln Asp Leu Leu
            180                 185                 190

Lys Leu Val Lys Ser Tyr His Trp Met Gly Leu Val His Ile Pro Thr
        195                 200                 205

Asn Gly Ser Trp Gln Trp Glu Asp Gly Ser Ile Leu Ser Pro Asn Leu
    210                 215                 220

Leu Thr Ile Ile Glu Met Gln Lys Gly Asp Cys Ala Leu Tyr Ala Ser
225                 230                 235                 240

Ser Phe Lys Gly Tyr Ile Glu Asn Cys Ser Thr Pro Asn Thr Tyr Ile
                245                 250                 255

Cys Met Gln Arg Thr Val
            260

<210> SEQ ID NO 4
<211> LENGTH: 262
<212> TYPE: PRT
<213> ORGANISM: Mus musculus

<400> SEQUENCE: 4

Asn Lys Glu Val Pro Val Ser Ser Arg Glu Gly Tyr Cys Gly Pro Cys
1               5                   10                  15

Pro Asn Asn Trp Ile Cys His Arg Asn Asn Cys Tyr Gln Phe Phe Asn
            20                  25                  30

Glu Glu Lys Thr Trp Asn Gln Ser Gln Ala Ser Cys Leu Ser Gln Asn
        35                  40                  45

Ser Ser Leu Leu Lys Ile Tyr Ser Lys Glu Glu Gln Asp Phe Leu Lys
    50                  55                  60

Leu Val Lys Ser Tyr His Trp Met Gly Leu Val Gln Ile Pro Ala Asn
65                  70                  75                  80

Gly Ser Trp Gln Trp Glu Asp Gly Ser Ser Leu Ser Tyr Asn Gln Leu
                85                  90                  95

Thr Leu Val Glu Ile Pro Lys Gly Ser Cys Ala Val Tyr Gly Ser Ser
            100                 105                 110

Phe Lys Ala Tyr Thr Glu Asp Cys Ala Asn Leu Asn Thr Tyr Ile Cys
            115                 120                 125

Met Lys Arg Ala Val Pro Val Ser Ser Arg Glu Gly Tyr Cys Gly Pro
        130                 135                 140

Cys Pro Asn Asn Trp Ile Cys His Arg Asn Asn Cys Tyr Gln Phe Phe
145                 150                 155                 160

Asn Glu Glu Lys Thr Trp Asn Gln Ser Gln Ala Ser Cys Leu Ser Gln
                165                 170                 175

Asn Ser Ser Leu Leu Lys Ile Tyr Ser Lys Glu Glu Gln Asp Phe Leu
            180                 185                 190

Lys Leu Val Lys Ser Tyr His Trp Met Gly Leu Val Gln Ile Pro Ala
            195                 200                 205

Asn Gly Ser Trp Gln Trp Glu Asp Gly Ser Ser Leu Ser Tyr Asn Gln
        210                 215                 220

Leu Thr Leu Val Glu Ile Pro Lys Gly Ser Cys Ala Val Tyr Gly Ser
225                 230                 235                 240

Ser Phe Lys Ala Tyr Thr Glu Asp Cys Ala Asn Leu Asn Thr Tyr Ile
                245                 250                 255

Cys Met Lys Arg Ala Val
            260

<210> SEQ ID NO 5
<211> LENGTH: 524
<212> TYPE: PRT
<213> ORGANISM: Artificial Sequence
<220> FEATURE:
<223> OTHER INFORMATION: human bivalent NKG2Dscd concatamer

<400> SEQUENCE: 5

Asn Gln Glu Val Gln Ile Pro Leu Thr Glu Ser Tyr Cys Gly Pro Cys
1               5                   10                  15

Pro Lys Asn Trp Ile Cys Tyr Lys Asn Asn Cys Tyr Gln Phe Phe Asp
            20                  25                  30

Glu Ser Lys Asn Trp Tyr Glu Ser Gln Ala Ser Cys Met Ser Gln Asn
        35                  40                  45

Ala Ser Leu Leu Lys Val Tyr Ser Lys Glu Asp Gln Asp Leu Leu Lys
    50                  55                  60

Leu Val Lys Ser Tyr His Trp Met Gly Leu Val His Ile Pro Thr Asn
65                  70                  75                  80

Gly Ser Trp Gln Trp Glu Asp Gly Ser Ile Leu Ser Pro Asn Leu Leu
                85                  90                  95

Thr Ile Ile Glu Met Gln Lys Gly Asp Cys Ala Leu Tyr Ala Ser Ser
            100                 105                 110

Phe Lys Gly Tyr Ile Glu Asn Cys Ser Thr Pro Asn Thr Tyr Ile Cys
            115                 120                 125

Met Gln Arg Thr Val Gln Ile Pro Leu Thr Glu Ser Tyr Cys Gly Pro
        130                 135                 140

Cys Pro Lys Asn Trp Ile Cys Tyr Lys Asn Asn Cys Tyr Gln Phe Phe
145                 150                 155                 160

```
Asp Glu Ser Lys Asn Trp Tyr Glu Ser Gln Ala Ser Cys Met Ser Gln
                165                 170                 175
Asn Ala Ser Leu Leu Lys Val Tyr Ser Lys Glu Asp Gln Asp Leu Leu
            180                 185                 190
Lys Leu Val Lys Ser Tyr His Trp Met Gly Leu Val His Ile Pro Thr
        195                 200                 205
Asn Gly Ser Trp Gln Trp Glu Asp Gly Ser Ile Leu Ser Pro Asn Leu
    210                 215                 220
Leu Thr Ile Ile Glu Met Gln Lys Gly Asp Cys Ala Leu Tyr Ala Ser
225                 230                 235                 240
Ser Phe Lys Gly Tyr Ile Glu Asn Cys Ser Thr Pro Asn Thr Tyr Ile
                245                 250                 255
Cys Met Gln Arg Thr Val Asn Gln Glu Val Gln Ile Pro Leu Thr Glu
            260                 265                 270
Ser Tyr Cys Gly Pro Cys Pro Lys Asn Trp Ile Cys Tyr Lys Asn Asn
        275                 280                 285
Cys Tyr Gln Phe Phe Asp Glu Ser Lys Asn Trp Tyr Glu Ser Gln Ala
    290                 295                 300
Ser Cys Met Ser Gln Asn Ala Ser Leu Leu Lys Val Tyr Ser Lys Glu
305                 310                 315                 320
Asp Gln Asp Leu Leu Lys Leu Val Lys Ser Tyr His Trp Met Gly Leu
                325                 330                 335
Val His Ile Pro Thr Asn Gly Ser Trp Gln Trp Glu Asp Gly Ser Ile
            340                 345                 350
Leu Ser Pro Asn Leu Leu Thr Ile Ile Glu Met Gln Lys Gly Asp Cys
        355                 360                 365
Ala Leu Tyr Ala Ser Ser Phe Lys Gly Tyr Ile Glu Asn Cys Ser Thr
    370                 375                 380
Pro Asn Thr Tyr Ile Cys Met Gln Arg Thr Val Gln Ile Pro Leu Thr
385                 390                 395                 400
Glu Ser Tyr Cys Gly Pro Cys Pro Lys Asn Trp Ile Cys Tyr Lys Asn
                405                 410                 415
Asn Cys Tyr Gln Phe Phe Asp Glu Ser Lys Asn Trp Tyr Glu Ser Gln
            420                 425                 430
Ala Ser Cys Met Ser Gln Asn Ala Ser Leu Leu Lys Val Tyr Ser Lys
        435                 440                 445
Glu Asp Gln Asp Leu Leu Lys Leu Val Lys Ser Tyr His Trp Met Gly
    450                 455                 460
Leu Val His Ile Pro Thr Asn Gly Ser Trp Gln Trp Glu Asp Gly Ser
465                 470                 475                 480
Ile Leu Ser Pro Asn Leu Leu Thr Ile Ile Glu Met Gln Lys Gly Asp
                485                 490                 495
Cys Ala Leu Tyr Ala Ser Ser Phe Lys Gly Tyr Ile Glu Asn Cys Ser
            500                 505                 510
Thr Pro Asn Thr Tyr Ile Cys Met Gln Arg Thr Val
        515                 520

<210> SEQ ID NO 6
<211> LENGTH: 524
<212> TYPE: PRT
<213> ORGANISM: Artificial Sequence
<220> FEATURE:
<223> OTHER INFORMATION: murine bivalent NKG2Dscd concatamer

<400> SEQUENCE: 6
```

-continued

```
Asn Lys Glu Val Pro Val Ser Ser Arg Glu Gly Tyr Cys Gly Pro Cys
1               5                   10                  15

Pro Asn Asn Trp Ile Cys His Arg Asn Asn Cys Tyr Gln Phe Phe Asn
            20                  25                  30

Glu Glu Lys Thr Trp Asn Gln Ser Gln Ala Ser Cys Leu Ser Gln Asn
                35                  40                  45

Ser Ser Leu Leu Lys Ile Tyr Ser Lys Glu Gln Asp Phe Leu Lys
    50                  55                  60

Leu Val Lys Ser Tyr His Trp Met Gly Leu Val Gln Ile Pro Ala Asn
65                  70                  75                  80

Gly Ser Trp Gln Trp Glu Asp Gly Ser Ser Leu Ser Tyr Asn Gln Leu
                85                  90                  95

Thr Leu Val Glu Ile Pro Lys Gly Ser Cys Ala Val Tyr Gly Ser Ser
                100                 105                 110

Phe Lys Ala Tyr Thr Glu Asp Cys Ala Asn Leu Asn Thr Tyr Ile Cys
            115                 120                 125

Met Lys Arg Ala Val Pro Val Ser Ser Arg Glu Gly Tyr Cys Gly Pro
    130                 135                 140

Cys Pro Asn Asn Trp Ile Cys His Arg Asn Asn Cys Tyr Gln Phe Phe
145                 150                 155                 160

Asn Glu Glu Lys Thr Trp Asn Gln Ser Gln Ala Ser Cys Leu Ser Gln
                165                 170                 175

Asn Ser Ser Leu Leu Lys Ile Tyr Ser Lys Glu Gln Asp Phe Leu
            180                 185                 190

Lys Leu Val Lys Ser Tyr His Trp Met Gly Leu Val Gln Ile Pro Ala
    195                 200                 205

Asn Gly Ser Trp Gln Trp Glu Asp Gly Ser Ser Leu Ser Tyr Asn Gln
210                 215                 220

Leu Thr Leu Val Glu Ile Pro Lys Gly Ser Cys Ala Val Tyr Gly Ser
225                 230                 235                 240

Ser Phe Lys Ala Tyr Thr Glu Asp Cys Ala Asn Leu Asn Thr Tyr Ile
                245                 250                 255

Cys Met Lys Arg Ala Val Asn Lys Glu Val Pro Val Ser Ser Arg Glu
                260                 265                 270

Gly Tyr Cys Gly Pro Cys Pro Asn Asn Trp Ile Cys His Arg Asn Asn
    275                 280                 285

Cys Tyr Gln Phe Phe Asn Glu Glu Lys Thr Trp Asn Gln Ser Gln Ala
    290                 295                 300

Ser Cys Leu Ser Gln Asn Ser Ser Leu Leu Lys Ile Tyr Ser Lys Glu
305                 310                 315                 320

Glu Gln Asp Phe Leu Lys Leu Val Lys Ser Tyr His Trp Met Gly Leu
            325                 330                 335

Val Gln Ile Pro Ala Asn Gly Ser Trp Gln Trp Glu Asp Gly Ser Ser
                340                 345                 350

Leu Ser Tyr Asn Gln Leu Thr Leu Val Glu Ile Pro Lys Gly Ser Cys
            355                 360                 365

Ala Val Tyr Gly Ser Ser Phe Lys Ala Tyr Thr Glu Asp Cys Ala Asn
    370                 375                 380

Leu Asn Thr Tyr Ile Cys Met Lys Arg Ala Val Pro Val Ser Ser Arg
385                 390                 395                 400

Glu Gly Tyr Cys Gly Pro Cys Pro Asn Asn Trp Ile Cys His Arg Asn
                405                 410                 415

Asn Cys Tyr Gln Phe Phe Asn Glu Glu Lys Thr Trp Asn Gln Ser Gln
```

```
                    420              425              430
Ala Ser Cys Leu Ser Gln Asn Ser Leu Leu Lys Ile Tyr Ser Lys
            435                  440                  445

Glu Glu Gln Asp Phe Leu Lys Leu Val Lys Ser Tyr His Trp Met Gly
    450                  455                  460

Leu Val Gln Ile Pro Ala Asn Gly Ser Trp Gln Trp Glu Asp Gly Ser
465                  470                  475                  480

Ser Leu Ser Tyr Asn Gln Leu Thr Leu Val Glu Ile Pro Lys Gly Ser
                485                  490                  495

Cys Ala Val Tyr Gly Ser Ser Phe Lys Ala Tyr Thr Glu Asp Cys Ala
                500                  505                  510

Asn Leu Asn Thr Tyr Ile Cys Met Lys Arg Ala Val
                515                  520

<210> SEQ ID NO 7
<211> LENGTH: 66
<212> TYPE: PRT
<213> ORGANISM: Artificial Sequence
<220> FEATURE:
<223> OTHER INFORMATION: multimerization domain

<400> SEQUENCE: 7

Arg Ser Ala Gly Ala His Ala Gly Trp Glu Thr Pro Glu Gly Cys Glu
1               5                   10                  15

Gln Val Leu Thr Gly Lys Arg Leu Met Gln Cys Leu Pro Asn Pro Glu
                20                  25                  30

Asp Val Lys Met Ala Leu Glu Val Tyr Lys Leu Ser Leu Glu Ile Glu
            35                  40                  45

Gln Leu Glu Leu Gln Arg Asp Ser Ala Arg Gln Ser Thr Leu Asp Lys
    50                  55                  60

Glu Leu
65

<210> SEQ ID NO 8
<211> LENGTH: 68
<212> TYPE: PRT
<213> ORGANISM: Artificial Sequence
<220> FEATURE:
<223> OTHER INFORMATION: multimerization domain

<400> SEQUENCE: 8

Ser Gly Arg Ala His Ala Gly Trp Glu Thr Pro Glu Gly Cys Glu Gln
1               5                   10                  15

Val Leu Thr Gly Lys Arg Leu Met Gln Cys Leu Pro Asn Pro Glu Asp
                20                  25                  30

Val Lys Met Ala Leu Glu Val Tyr Lys Leu Ser Leu Glu Ile Glu Gln
            35                  40                  45

Leu Glu Leu Gln Arg Asp Ser Ala Arg Gln Ser Thr Leu Asp Lys Glu
    50                  55                  60

Leu Val Pro Arg
65

<210> SEQ ID NO 9
<211> LENGTH: 55
<212> TYPE: PRT
<213> ORGANISM: Artificial Sequence
<220> FEATURE:
<223> OTHER INFORMATION: multimerization domain

<400> SEQUENCE: 9
```

```
Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
                20                  25                  30

Leu Glu Ile Arg Lys Leu Phe Leu Glu Ile Gln Lys Leu Lys Val Glu
            35                  40                  45

Leu Gln Gly Leu Ser Lys Glu
    50                  55

<210> SEQ ID NO 10
<211> LENGTH: 57
<212> TYPE: PRT
<213> ORGANISM: Artificial Sequence
<220> FEATURE:
<223> OTHER INFORMATION: multimerization domain

<400> SEQUENCE: 10

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
                20                  25                  30

Lys Leu Ser Leu Glu Ile Glu Gln Leu Glu Leu Gln Arg Asp Ser Ala
            35                  40                  45

Arg Gln Ser Thr Leu Asp Lys Glu Leu
    50                  55

<210> SEQ ID NO 11
<211> LENGTH: 58
<212> TYPE: PRT
<213> ORGANISM: Artificial Sequence
<220> FEATURE:
<223> OTHER INFORMATION: multimerization domain

<400> SEQUENCE: 11

Trp Glu Thr Pro Glu Gly Cys Glu Gln Val Leu Thr Gly Lys Arg Leu
1               5                   10                  15

Met Gln Cys Leu Pro Asn Pro Glu Asp Val Lys Met Ala Leu Glu Val
                20                  25                  30

Tyr Lys Leu Ser Leu Glu Ile Glu Gln Leu Glu Leu Gln Arg Asp Ser
            35                  40                  45

Ala Arg Gln Ser Thr Leu Asp Lys Glu Leu
    50                  55

<210> SEQ ID NO 12
<211> LENGTH: 52
<212> TYPE: PRT
<213> ORGANISM: Artificial Sequence
<220> FEATURE:
<223> OTHER INFORMATION: multimerization domain

<400> SEQUENCE: 12

Cys Glu Gln Val Leu Thr Gly Lys Arg Leu Met Gln Cys Leu Pro Asn
1               5                   10                  15

Pro Glu Asp Val Lys Met Ala Leu Glu Val Tyr Lys Leu Ser Leu Glu
                20                  25                  30

Ile Glu Gln Leu Glu Leu Gln Arg Asp Ser Ala Arg Gln Ser Thr Leu
            35                  40                  45

Asp Lys Glu Leu
    50
```

```
<210> SEQ ID NO 13
<211> LENGTH: 57
<212> TYPE: PRT
<213> ORGANISM: Artificial Sequence
<220> FEATURE:
<223> OTHER INFORMATION: multimerization domain

<400> SEQUENCE: 13

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45

Arg Gln Tyr Thr Leu Asp Lys Glu Leu
    50                  55

<210> SEQ ID NO 14
<211> LENGTH: 57
<212> TYPE: PRT
<213> ORGANISM: Artificial Sequence
<220> FEATURE:
<223> OTHER INFORMATION: multimerization domain

<400> SEQUENCE: 14

Glu Thr Pro Glu Gly Cys Glu Gln Val Leu Ala Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Arg Ala
        35                  40                  45

Arg Gln Ser Thr Leu Asp Lys Glu Leu
    50                  55

<210> SEQ ID NO 15
<211> LENGTH: 57
<212> TYPE: PRT
<213> ORGANISM: Artificial Sequence
<220> FEATURE:
<223> OTHER INFORMATION: multimerization domain

<400> SEQUENCE: 15

Glu Thr Pro Glu Gly Cys Glu Gln Val Leu Ala Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Arg Ala
        35                  40                  45

Arg Gln Ser Thr Trp Asp Lys Glu Leu
    50                  55

<210> SEQ ID NO 16
<211> LENGTH: 57
<212> TYPE: PRT
<213> ORGANISM: Artificial Sequence
<220> FEATURE:
<223> OTHER INFORMATION: multimerization domain

<400> SEQUENCE: 16

Glu Val Pro Glu Gly Cys Glu Gln Val Gln Ala Gly Arg Arg Leu Met
1               5                   10                  15
```

Gln Cys Leu Ala Asp Pro Tyr Glu Val Lys Met Ala Leu Glu Val Tyr
            20                  25                  30

Lys Leu Ser Leu Glu Ile Glu Leu Leu Glu Leu Gln Arg Asp Lys Ala
        35                  40                  45

Arg Lys Ser Ser Val Leu Arg Gln Leu
    50                  55

<210> SEQ ID NO 17
<211> LENGTH: 57
<212> TYPE: PRT
<213> ORGANISM: Artificial Sequence
<220> FEATURE:
<223> OTHER INFORMATION: multimerization domain

<400> SEQUENCE: 17

Val Val Pro Glu Gly Cys Glu His Ile Leu Lys Gly Arg Lys Thr Met
1               5                   10                  15

Gln Cys Leu Pro Asn Pro Glu Asp Val Lys Met Ala Leu Glu Ile Tyr
            20                  25                  30

Lys Leu Ser Leu Asp Ile Glu Leu Leu Glu Leu Gln Arg Asp Arg Ala
        35                  40                  45

Lys Glu Ser Thr Val Gln Ser Pro Val
    50                  55

<210> SEQ ID NO 18
<211> LENGTH: 55
<212> TYPE: PRT
<213> ORGANISM: Artificial Sequence
<220> FEATURE:
<223> OTHER INFORMATION: multimerization domain

<400> SEQUENCE: 18

Glu Val Pro Lys Asp Cys Glu His Val Phe Ala Gly Lys Lys Leu Met
1               5                   10                  15

Gln Cys Leu Pro Asn Ser Asn Asp Val Lys Met Ala Leu Glu Val Tyr
            20                  25                  30

Lys Leu Thr Leu Glu Ile Lys Gln Leu Gln Leu Gln Ile Asp Lys Ala
        35                  40                  45

Lys His Val Asp Arg Glu Leu
    50                  55

<210> SEQ ID NO 19
<211> LENGTH: 57
<212> TYPE: PRT
<213> ORGANISM: Artificial Sequence
<220> FEATURE:
<223> OTHER INFORMATION: multimerization domain

<400> SEQUENCE: 19

Glu Tyr Pro Glu Asp Cys Glu Gln Val His Glu Gly Lys Lys Leu Met
1               5                   10                  15

Gln Cys Leu Pro Asn Leu Glu Glu Ile Lys Leu Ala Leu Glu Leu Tyr
            20                  25                  30

Lys Leu Ser Leu Glu Thr Lys Leu Leu Glu Leu Gln Ile Asp Lys Glu
        35                  40                  45

Lys Lys Ala Lys Ala Lys Tyr Ser Ile
    50                  55

<210> SEQ ID NO 20
<211> LENGTH: 57
<212> TYPE: PRT

```
<213> ORGANISM: Artificial Sequence
<220> FEATURE:
<223> OTHER INFORMATION: multimerization domain

<400> SEQUENCE: 20

Glu Tyr Pro Glu Asp Cys Glu Gln Val His Glu Gly Lys Lys Leu Met
1               5                   10                  15

Glu Cys Leu Pro Thr Leu Glu Glu Ile Lys Leu Ala Leu Ala Leu Tyr
            20                  25                  30

Lys Leu Ser Leu Glu Thr Asn Leu Leu Glu Leu Gln Ile Asp Lys Glu
        35                  40                  45

Lys Lys Ala Lys Ala Lys Tyr Ser Thr
    50                  55

<210> SEQ ID NO 21
<211> LENGTH: 57
<212> TYPE: PRT
<213> ORGANISM: Artificial Sequence
<220> FEATURE:
<223> OTHER INFORMATION: multimerization domain

<400> SEQUENCE: 21

Glu Ile Ala Glu Gly Cys Glu Gln Val Leu Ala Gly Arg Lys Ile Met
1               5                   10                  15

Gln Cys Leu Pro Lys Pro Glu Asp Val Arg Thr Ala Leu Glu Leu Tyr
            20                  25                  30

Lys Leu Ser Leu Glu Ile Lys Gln Leu Glu Lys Lys Leu Glu Lys Glu
        35                  40                  45

Glu Lys Cys Thr Pro Glu Val Gln Glu
    50                  55

<210> SEQ ID NO 22
<211> LENGTH: 67
<212> TYPE: PRT
<213> ORGANISM: Artificial Sequence
<220> FEATURE:
<223> OTHER INFORMATION: multimerization domain

<400> SEQUENCE: 22

Glu Tyr Pro Glu Gly Cys Glu Gln Val Val Thr Gly Arg Lys Leu Leu
1               5                   10                  15

Gln Cys Leu Ser Arg Pro Glu Glu Val Lys Leu Ala Leu Glu Val Tyr
            20                  25                  30

Lys Leu Ser Leu Glu Ile Glu Ile Leu Gln Thr Asn Lys Leu Lys Lys
        35                  40                  45

Glu Ala Phe Leu Leu Arg Glu Arg Glu Lys Asn Val Thr Cys Asp Phe
    50                  55                  60

Asn Pro Glu
65

<210> SEQ ID NO 23
<211> LENGTH: 52
<212> TYPE: PRT
<213> ORGANISM: Artificial Sequence
<220> FEATURE:
<223> OTHER INFORMATION: multimerization domain

<400> SEQUENCE: 23

Glu Tyr Pro Glu Gly Cys Glu Gln Val Val Thr Gly Arg Lys Leu Leu
1               5                   10                  15

Lys Cys Leu Ser Arg Pro Glu Glu Val Lys Leu Ala Leu Glu Val Tyr
```

```
                20                  25                  30

Lys Leu Ser Leu Glu Ile Ala Leu Leu Glu Leu Gln Ile Asp Lys Pro
        35                  40                  45

Lys Asp Ala Ser
    50

<210> SEQ ID NO 24
<211> LENGTH: 52
<212> TYPE: PRT
<213> ORGANISM: Artificial Sequence
<220> FEATURE:
<223> OTHER INFORMATION: multimerization domain

<400> SEQUENCE: 24

Glu Val Pro Glu Asn Cys Glu Gln Val Ile Val Gly Lys Lys Leu Met
1               5                   10                  15

Lys Cys Leu Ser Asn Pro Asp Glu Ala Gln Met Ala Leu Gln Leu Tyr
            20                  25                  30

Lys Leu Ser Leu Glu Ala Glu Leu Leu Arg Leu Gln Ile Val Lys Ala
        35                  40                  45

Arg Gln Gly Ser
    50

<210> SEQ ID NO 25
<211> LENGTH: 54
<212> TYPE: PRT
<213> ORGANISM: Artificial Sequence
<220> FEATURE:
<223> OTHER INFORMATION: multimerization domain

<400> SEQUENCE: 25

Glu Ala Ser Glu Asp Leu Lys Pro Ala Leu Thr Gly Asn Lys Thr Met
1               5                   10                  15

Gln Tyr Val Pro Asn Ser His Asp Val Lys Met Ala Leu Glu Ile Tyr
            20                  25                  30

Lys Leu Thr Leu Glu Val Glu Leu Leu Gln Leu Gln Ile Gln Lys Glu
        35                  40                  45

Lys His Thr Glu Ala His
    50

<210> SEQ ID NO 26
<211> LENGTH: 51
<212> TYPE: PRT
<213> ORGANISM: Artificial Sequence
<220> FEATURE:
<223> OTHER INFORMATION: multimerization domain

<400> SEQUENCE: 26

Val Ser Ala Glu Val Cys Glu Ala Val Phe Lys Gly Gln Lys Leu Leu
1               5                   10                  15

Lys Cys Leu Pro Asn Ala Met Glu Val Lys Met Ala Leu Glu Val Tyr
            20                  25                  30

Lys Leu Ser Leu Glu Ile Glu Lys Leu Glu Gln Glu Lys Arg Lys Leu
        35                  40                  45

Glu Ile Ala
    50

<210> SEQ ID NO 27
<211> LENGTH: 66
<212> TYPE: PRT
<213> ORGANISM: Artificial Sequence
```

```
<220> FEATURE:
<223> OTHER INFORMATION: multimerization domain

<400> SEQUENCE: 27

Glu Val Pro Glu Glu Cys Lys Gln Val Ala Ala Gly Arg Lys Leu Leu
1               5                   10                  15

Glu Cys Leu Pro Asn Pro Ser Asp Val Lys Met Ala Leu Glu Val Tyr
            20                  25                  30

Lys Leu Ser Leu Glu Ile Glu Gln Leu Glu Lys Glu Lys Tyr Val Lys
        35                  40                  45

Ile Gln Glu Lys Phe Ser Lys Lys Glu Met Lys Gln Leu Thr Ser Ala
    50                  55                  60

Leu His
65

<210> SEQ ID NO 28
<211> LENGTH: 59
<212> TYPE: PRT
<213> ORGANISM: Artificial Sequence
<220> FEATURE:
<223> OTHER INFORMATION: multimerization domain

<400> SEQUENCE: 28

Glu Val Leu Glu Asp Cys Arg Ile Val Ser Arg Gly Ala Gln Leu Leu
1               5                   10                  15

His Cys Leu Ser Ser Pro Glu Asp Val His Arg Ala Leu Lys Val Tyr
            20                  25                  30

Lys Leu Phe Leu Glu Ile Glu Arg Leu Glu His Gln Lys Glu Lys Trp
        35                  40                  45

Ile Gln Leu His Arg Lys Pro Gln Ser Met Lys
    50                  55

<210> SEQ ID NO 29
<211> LENGTH: 63
<212> TYPE: PRT
<213> ORGANISM: Artificial Sequence
<220> FEATURE:
<223> OTHER INFORMATION: multimerization domain

<400> SEQUENCE: 29

Glu Gly Pro Glu Asp Cys Glu Ile Val Asn Lys Gly Arg Gln Leu Leu
1               5                   10                  15

Gln Cys Leu Ser Ser Pro Glu Asp Val Gln Arg Ala Leu Glu Val Tyr
            20                  25                  30

Lys Leu Ser Leu Glu Ile Glu Arg Leu Glu Gln Gln Arg Glu Lys Arg
        35                  40                  45

Thr Ser Val His Arg Lys Ala His Tyr Thr Lys Val Asp Gly Pro
    50                  55                  60

<210> SEQ ID NO 30
<211> LENGTH: 67
<212> TYPE: PRT
<213> ORGANISM: Artificial Sequence
<220> FEATURE:
<223> OTHER INFORMATION: multimerization domain

<400> SEQUENCE: 30

Glu Ala Pro Glu Gly Cys Glu Gln Val Leu Thr Gly Arg Lys Leu Met
1               5                   10                  15

Gln Cys Leu Pro Ser Pro Glu Asp Val Lys Val Ala Leu Glu Val Tyr
            20                  25                  30
```

```
Lys Leu Ser Leu Glu Ile Lys Gln Leu Glu Lys Glu Arg Asp Lys Leu
        35                  40                  45

Met Asn Thr His Gln Lys Phe Ser Glu Lys Glu Met Lys Asp Leu
 50                  55                  60

Phe Phe Pro
 65

<210> SEQ ID NO 31
<211> LENGTH: 52
<212> TYPE: PRT
<213> ORGANISM: Artificial Sequence
<220> FEATURE:
<223> OTHER INFORMATION: multimerization domain

<400> SEQUENCE: 31

Glu Val Pro Glu Gly Cys Glu Gln Val Leu Thr Gly Lys Lys Leu Met
 1               5                  10                  15

Gln Cys Leu Pro Asn Pro Glu Asp Val Lys Met Ala Leu Glu Val Tyr
            20                  25                  30

Lys Leu Ser Leu Glu Ile Glu Leu Leu Glu Leu Gln Ile Asp Lys Ala
        35                  40                  45

Arg Gln Gly Ser
     50

<210> SEQ ID NO 32
<211> LENGTH: 47
<212> TYPE: PRT
<213> ORGANISM: Artificial Sequence
<220> FEATURE:
<223> OTHER INFORMATION: multimerization domain

<400> SEQUENCE: 32

Gly Cys Glu Gln Val Leu Thr Gly Lys Arg Leu Met Gln Cys Leu Pro
 1               5                  10                  15

Asn Pro Glu Asp Val Lys Met Ala Leu Glu Val Tyr Lys Leu Ser Leu
            20                  25                  30

Glu Ile Glu Gln Leu Glu Leu Gln Arg Asp Ser Ala Arg Gln Ser
        35                  40                  45

<210> SEQ ID NO 33
<211> LENGTH: 51
<212> TYPE: PRT
<213> ORGANISM: Artificial Sequence
<220> FEATURE:
<223> OTHER INFORMATION: multimerization domain

<400> SEQUENCE: 33

Glu Thr Pro Glu Gly Cys Glu Gln Val Leu Thr Gly Lys Arg Leu Met
 1               5                  10                  15

Gln Cys Leu Pro Asn Pro Glu Asp Val Lys Met Ala Leu Glu Val Tyr
            20                  25                  30

Lys Leu Ser Leu Glu Ile Glu Leu Glu Leu Gln Arg Asp Ser Ala
        35                  40                  45

Arg Gln Ser
     50

<210> SEQ ID NO 34
<211> LENGTH: 53
<212> TYPE: PRT
<213> ORGANISM: Artificial Sequence
<220> FEATURE:
```

<223> OTHER INFORMATION: multimerization domain

<400> SEQUENCE: 34

Gly Ser Glu Gln Val Leu Thr Gly Lys Arg Leu Met Gln Ser Leu Pro
1               5                   10                  15

Asn Pro Glu Asp Val Lys Met Ala Leu Glu Val Tyr Lys Leu Ser Leu
            20                  25                  30

Glu Ile Glu Gln Leu Glu Leu Gln Arg Asp Ser Ala Arg Gln Ser Thr
        35                  40                  45

Leu Asp Lys Glu Leu
    50

<210> SEQ ID NO 35
<211> LENGTH: 57
<212> TYPE: PRT
<213> ORGANISM: Artificial Sequence
<220> FEATURE:
<223> OTHER INFORMATION: multimerization domain

<400> SEQUENCE: 35

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Ile Tyr
            20                  25                  30

Lys Leu Thr Leu Glu Ile Glu Gln Leu Glu Leu Gln Arg Asp Ser Ala
        35                  40                  45

Arg Gln Ser Thr Leu Asp Lys Glu Leu
    50                  55

<210> SEQ ID NO 36
<211> LENGTH: 57
<212> TYPE: PRT
<213> ORGANISM: Artificial Sequence
<220> FEATURE:
<223> OTHER INFORMATION: multimerization domain

<400> SEQUENCE: 36

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Ile Tyr
            20                  25                  30

Lys Leu Ser Leu Glu Ile Lys Gln Leu Glu Leu Gln Arg Asp Ser Ala
        35                  40                  45

Arg Gln Ser Thr Leu Asp Lys Glu Leu
    50                  55

<210> SEQ ID NO 37
<211> LENGTH: 50
<212> TYPE: PRT
<213> ORGANISM: Artificial Sequence
<220> FEATURE:
<223> OTHER INFORMATION: multimerization domain

<400> SEQUENCE: 37

Glu Gly Cys Glu Gln Ile Leu Thr Gly Lys Arg Leu Met Gln Cys Leu
1               5                   10                  15

Pro Asp Pro Glu Asp Val Lys Met Ala Leu Glu Ile Tyr Lys Leu Ser
            20                  25                  30

Leu Glu Ile Lys Gln Leu Glu Leu Gln Arg Asp Arg Ala Arg Gln Ser
        35                  40                  45

```
<210> SEQ ID NO 38
<211> LENGTH: 57
<212> TYPE: PRT
<213> ORGANISM: Artificial Sequence
<220> FEATURE:
<223> OTHER INFORMATION: multimerization domain

<400> SEQUENCE: 38

Glu Thr Pro Glu Gly Cys Glu Gln Val Leu Thr Gly Lys Arg Leu Met
1               5                   10                  15
Gln Cys Leu Pro Asn Pro Glu Asp Val Lys Met Ala Leu Glu Val Tyr
            20                  25                  30
Lys Leu Ser Leu Glu Ile Lys Gln Leu Glu Leu Gln Arg Asp Arg Ala
        35                  40                  45
Arg Gln Ser Thr Leu Asp Lys Glu Leu
    50                  55

<210> SEQ ID NO 39
<211> LENGTH: 52
<212> TYPE: PRT
<213> ORGANISM: Artificial Sequence
<220> FEATURE:
<223> OTHER INFORMATION: multimerization domain

<400> SEQUENCE: 39

Glu Gly Cys Glu Gln Ile Leu Thr Gly Lys Arg Leu Met Gln Cys Leu
1               5                   10                  15
Pro Asn Pro Glu Asp Val Lys Met Ala Leu Glu Ile Tyr Lys Leu Ser
            20                  25                  30
Leu Glu Ile Glu Gln Leu Glu Leu Gln Arg Asp Arg Ala Arg Gln Ser
        35                  40                  45
Thr Leu Asp Lys
    50

<210> SEQ ID NO 40
<211> LENGTH: 7
<212> TYPE: PRT
<213> ORGANISM: Artificial Sequence
<220> FEATURE:
<223> OTHER INFORMATION: linker

<400> SEQUENCE: 40

Gly Ser Ser Gly Ser Ser Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Flag tag

<400> SEQUENCE: 41

Asp Tyr Lys Asp Glu
1               5

<210> SEQ ID NO 42
<211> LENGTH: 6
<212> TYPE: PRT
<213> ORGANISM: Artificial Sequence
<220> FEATURE:
```

```
<223> OTHER INFORMATION: His tag

<400> SEQUENCE: 42

His His His His His His
1               5

<210> SEQ ID NO 43
<211> LENGTH: 8
<212> TYPE: PRT
<213> ORGANISM: Artificial Sequence
<220> FEATURE:
<223> OTHER INFORMATION: His tag

<400> SEQUENCE: 43

Gly Ser His His His His His His
1               5

<210> SEQ ID NO 44
<211> LENGTH: 9
<212> TYPE: PRT
<213> ORGANISM: Artificial Sequence
<220> FEATURE:
<223> OTHER INFORMATION: His tag

<400> SEQUENCE: 44

Gly Thr Lys His His His His His His
1               5

<210> SEQ ID NO 45
<211> LENGTH: 178
<212> TYPE: PRT
<213> ORGANISM: Homo sapiens

<400> SEQUENCE: 45

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 46
<211> LENGTH: 180
```

<212> TYPE: PRT
<213> ORGANISM: Mus musculus

<400> SEQUENCE: 46

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
            20                  25                  30

Val Val Gly Leu Ala Gly Asn Ala Val Gln Lys Lys Thr Glu Gly Ser
        35                  40                  45

Phe Thr Met Tyr Ser Thr Ile Tyr Glu Leu Gln Glu Asn Asn Ser Tyr
    50                  55                  60

Asn Val Thr Ser Ile Leu Val Arg Asp Gln Asp Gln Gly Cys Arg Tyr
65                  70                  75                  80

Trp Ile Arg Thr Phe Val Pro Ser Ser Arg Ala Gly Gln Phe Thr Leu
                85                  90                  95

Gly Asn Met His Arg Tyr Pro Gln Val Gln Ser Tyr Asn Val Gln Val
            100                 105                 110

Ala Thr Thr Asp Tyr Asn Gln Phe Ala Met Val Phe Phe Arg Lys Thr
        115                 120                 125

Ser Glu Asn Lys Gln Tyr Phe Lys Ile Thr Leu Tyr Gly Arg Thr Lys
    130                 135                 140

Glu Leu Ser Pro Glu Leu Lys Glu Arg Phe Thr Arg Phe Ala Lys Ser
145                 150                 155                 160

Leu Gly Leu Lys Asp Asp Asn Ile Ile Phe Ser Val Pro Thr Asp Gln
                165                 170                 175

Cys Ile Asp Asn
            180

<210> SEQ ID NO 47
<211> LENGTH: 178
<212> TYPE: PRT
<213> ORGANISM: Rattus norvegicus

<400> SEQUENCE: 47

Gln Asp Ser Thr Gln Asn Leu Ile Pro Ala Pro Pro Leu Ile Ser Val
1               5                   10                  15

Pro Leu Gln Pro Gly Phe Trp Thr Glu Arg Phe Gln Gly Arg Trp Phe
            20                  25                  30

Val Val Gly Leu Ala Ala Asn Ala Val Gln Lys Glu Arg Gln Ser Arg
        35                  40                  45

Phe Thr Met Tyr Ser Thr Ile Tyr Glu Leu Gln Glu Asp Asn Ser Tyr
    50                  55                  60

Asn Val Thr Ser Ile Leu Val Arg Gly Gln Gly Cys Arg Tyr Trp Ile
65                  70                  75                  80

Arg Thr Phe Val Pro Ser Ser Arg Pro Gly Gln Phe Thr Leu Gly Asn
                85                  90                  95

Ile His Ser Tyr Pro Gln Ile Gln Ser Tyr Asp Val Gln Val Ala Asp
            100                 105                 110

Thr Asp Tyr Asp Gln Phe Ala Met Val Phe Phe Gln Lys Thr Ser Glu
        115                 120                 125

Asn Lys Gln Tyr Phe Lys Val Thr Leu Tyr Gly Arg Thr Lys Gly Leu
    130                 135                 140

Ser Asp Glu Leu Lys Glu Arg Phe Val Ser Phe Ala Lys Ser Leu Gly
145                 150                 155                 160

Leu Lys Asp Asn Asn Ile Val Phe Ser Val Pro Thr Asp Gln Cys Ile
                165                 170                 175

Asp Asn

<210> SEQ ID NO 48
<211> LENGTH: 178
<212> TYPE: PRT
<213> ORGANISM: Pan troglodytes

<400> SEQUENCE: 48

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Arg Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 49
<211> LENGTH: 180
<212> TYPE: PRT
<213> ORGANISM: Gorilla gorilla

<400> SEQUENCE: 49

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Glu Lys Ala Gln Lys Cys Asp Tyr
65                  70                  75                  80

Trp Ile Arg Thr Phe Val Pro Gly Ser Gln Pro Gly Glu Phe Thr Leu
                85                  90                  95

Gly Asn Ile Lys Ser Tyr Pro Gly Leu Thr Ser Tyr Leu Val Arg Val
                100                 105                 110

Val Ser Thr Asn Tyr Asn Gln His Ala Met Val Phe Phe Lys Lys Val
            115                 120                 125

```
Ser Gln Asn Arg Glu Tyr Phe Lys Ile Thr Leu Tyr Gly Arg Thr Lys
            130                 135                 140

Glu Leu Thr Ser Glu Leu Lys Glu Asn Phe Ile Arg Phe Ser Lys Ser
145                 150                 155                 160

Leu Gly Leu Pro Glu Asn His Ile Val Phe Pro Val Pro Ile Asp Gln
                165                 170                 175

Cys Ile Asp Gly
            180

<210> SEQ ID NO 50
<211> LENGTH: 178
<212> TYPE: PRT
<213> ORGANISM: Pongo pygmaeus

<400> SEQUENCE: 50

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Arg Arg Glu Asp Lys Asp Ser
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Thr Lys Gly Tyr Pro Gly Leu Thr Ser Tyr Leu Val Arg Val Val Ser
            100                 105                 110

Thr Asn Tyr Asn Gln Tyr Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Ala Pro Ile Asp Gln Cys Ile
                165                 170                 175

Asp Gly

<210> SEQ ID NO 51
<211> LENGTH: 178
<212> TYPE: PRT
<213> ORGANISM: Macacca mullatta

<400> SEQUENCE: 51

Gln Asp Ser Ser Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ser Gly Asn Ala Val Gly Arg Lys Asp Glu Ala Pro
        35                  40                  45

Leu Lys Met Tyr Ala Thr Ile Tyr Glu Leu Lys Glu Asp Lys Ser Tyr
    50                  55                  60

Asn Val Thr Ser Ile Leu Phe Arg Lys Glu Lys Cys Asp Tyr Trp Ile
65                  70                  75                  80
```

```
Arg Thr Phe Val Pro Gly Ser Gln Pro Gly Glu Phe Thr Leu Gly Asn
                85                  90                  95

Ile Gln Asn His Pro Gly Leu Thr Ser Tyr Val Val Arg Val Val Ser
            100                 105                 110

Thr Asn Tyr Lys Gln Tyr Ala Met Val Phe Lys Lys Val Ser Gln
            115                 120                 125

Asn Lys Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Ser Val Pro Ile Asp Gln Cys Ile
                165                 170                 175

Asn Gly

<210> SEQ ID NO 52
<211> LENGTH: 178
<212> TYPE: PRT
<213> ORGANISM: Callithrix jacchus

<400> SEQUENCE: 52

Gln Asp Ser Pro Ser Pro Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Arg Arg Glu Asp Gln Asp Ser
            35                  40                  45

Leu Lys Met Tyr Ala Thr Ile Tyr Glu Leu Lys Glu Asp Lys Ser Tyr
50                  55                  60

Asn Val Thr Ser Val Leu Phe Arg Lys Gly Lys Cys Asp Tyr Trp Ile
65                  70                  75                  80

Arg Thr Phe Val Pro Ser Ser Arg Pro Gly Glu Phe Lys Leu Gly Asn
                85                  90                  95

Ile Glu Ser His Pro Gly Leu Thr Ser Tyr Ile Val Arg Val Val Asn
            100                 105                 110

Thr Asp Tyr Lys Gln His Ala Met Val Phe Phe Met Lys Ala Ser His
            115                 120                 125

Asn Arg Lys Tyr Phe Lys Val Thr Leu Tyr Gly Arg Thr Lys Glu Leu
            130                 135                 140

Thr Ser Asp Leu Lys Glu Asn Phe Thr Ser Phe Ser Lys Ser Leu Gly
145                 150                 155                 160

Leu Thr Glu Asn His Ile Ile Phe Pro Val Pro Ile Asp Gln Cys Ile
                165                 170                 175

Asp Gly

<210> SEQ ID NO 53
<211> LENGTH: 185
<212> TYPE: PRT
<213> ORGANISM: Ochotona princeps

<400> SEQUENCE: 53

Gln Glu Leu Thr Met Asp Pro Thr Pro Ser Pro Arg Leu Ile Pro Val
1               5                   10                  15

Pro Ser Leu Arg Lys Ile His Val Gln Lys Asn Phe Gln Ser Asp Gln
                20                  25                  30

Phe Gln Gly Lys Trp Tyr Val Val Gly Leu Ala Gly Asn Asn Ile His
            35                  40                  45
```

Asn Ser Asp Gln Glu His Gln Met Tyr Ser Thr Thr Tyr Glu Leu
    50              55                  60

Lys Glu Asp Gly Ser Tyr Asn Val Thr Ser Thr Leu Leu Arg Asn Gln
65              70                  75                  80

Gln Cys Asp His Trp Ile Arg Thr Phe Val Pro Gly Ser Lys Leu Gly
                85                  90                  95

His Phe Asn Leu Gly Asn Ile Lys Ser Tyr Pro Thr Leu Lys Ser Tyr
            100                 105                 110

Leu Ile Arg Val Val Thr Thr Asp Tyr Asn Gln Phe Ala Ile Val Phe
            115                 120                 125

Phe Arg Lys Val Tyr Lys Asn Asn Lys Lys Phe Lys Ile Val Leu
        130                 135                 140

Tyr Gly Arg Thr Lys Glu Leu Ser Pro Glu Leu Arg Gly Arg Phe Thr
145                 150                 155                 160

Ser Phe Ala Lys Thr Leu Gly Leu Thr Asp Asn His Ile Val Phe Pro
                165                 170                 175

Ala Pro Ile Gly Gln Cys Ile Asp Asp
                180                 185

<210> SEQ ID NO 54
<211> LENGTH: 178
<212> TYPE: PRT
<213> ORGANISM: Oryctolagus cuniculus

<400> SEQUENCE: 54

Gln Asp Pro Thr Pro Lys Leu Ile Pro Ala Pro Ser Leu Arg Arg Val
1               5                   10                  15

Pro Leu Gln Arg Asn Phe Gln Asp Glu Gln Phe Gln Gly Lys Trp Tyr
                20                  25                  30

Val Val Gly Leu Ala Gly Asn Ala Val Gln Lys Arg Glu Glu Gly Gln
            35                  40                  45

Glu Pro Met Tyr Ser Thr Thr Tyr Glu Leu Asn Glu Asp Arg Ser Phe
    50                  55                  60

Asn Val Thr Ser Thr Leu Leu Arg Asp Gln Arg Cys Asp His Trp Ile
65              70                  75                  80

Arg Thr Phe Val Pro Thr Ser Arg Pro Gly Gln Tyr Asn Leu Gly Asn
                85                  90                  95

Ile Lys Ser Tyr Pro Gly Val Lys Asn Tyr Ile Val Arg Val Val Ala
            100                 105                 110

Thr Asp Tyr Ser Gln Tyr Ala Met Met Phe Phe Arg Lys Gly Ser Arg
            115                 120                 125

Asn Lys Gln Phe Phe Lys Thr Thr Leu Tyr Gly Arg Thr Lys Glu Leu
        130                 135                 140

Ser Pro Glu Leu Arg Glu Arg Phe Thr Arg Phe Ala Lys Ser Leu Gly
145                 150                 155                 160

Leu Pro Asp Asp Arg Ile Val Phe Pro Thr Pro Ile Asp Gln Cys Ile
                165                 170                 175

Asp Asp

<210> SEQ ID NO 55
<211> LENGTH: 179
<212> TYPE: PRT
<213> ORGANISM: Bos taurus

<400> SEQUENCE: 55

-continued

```
Arg Ser Ser Ser Ser Arg Leu Leu Arg Ala Pro Pro Leu Ser Arg Ile
1               5                   10                  15

Pro Leu Gln Pro Asn Phe Gln Ala Asp Gln Phe Gln Gly Lys Trp Tyr
            20                  25                  30

Thr Val Gly Val Ala Gly Asn Ala Ile Lys Lys Glu Glu Gln Asp Pro
        35                  40                  45

Leu Lys Met Tyr Ser Ser Asn Tyr Glu Leu Lys Glu Asp Gly Ser Tyr
    50                  55                  60

Asn Val Thr Ser Ile Leu Leu Lys Asp Asp Leu Cys Asp Tyr Trp Ile
65                  70                  75                  80

Arg Thr Phe Val Pro Ser Ser Gln Pro Gly Gln Phe Thr Leu Gly Asn
                85                  90                  95

Ile Lys Ser Tyr Arg Gly Ile Arg Ser Tyr Thr Val Arg Val Val Asn
            100                 105                 110

Thr Asp Tyr Asn Gln Phe Ala Ile Val Tyr Phe Lys Lys Val Gln Arg
            115                 120                 125

Lys Lys Thr Tyr Phe Lys Ile Thr Leu Tyr Gly Arg Thr Lys Glu Leu
        130                 135                 140

Thr Pro Glu Val Arg Glu Asn Phe Ile Asn Phe Ala Lys Ser Leu Gly
145                 150                 155                 160

Leu Thr Asp Asp His Ile Val Phe Thr Val Pro Ile Asp Arg Cys Ile
                165                 170                 175

Asp Asp Gln

<210> SEQ ID NO 56
<211> LENGTH: 179
<212> TYPE: PRT
<213> ORGANISM: Sus scrofa

<400> SEQUENCE: 56

Gln Gly Thr Ile Pro Asn Trp Ile Pro Ala Pro Pro Leu Ser Lys Val
1               5                   10                  15

Pro Leu Gln Pro Asn Phe Gln Ala Asp Gln Phe Gln Gly Lys Trp Tyr
            20                  25                  30

Val Val Gly Leu Ala Gly Asn Ala Val Lys Lys Glu Glu Gln Gly Arg
        35                  40                  45

Phe Lys Met Tyr Thr Thr Thr Tyr Glu Leu Lys Glu Asp Gly Ser Tyr
    50                  55                  60

Asn Val Ile Ser Thr Leu Leu Arg Gly Gln Leu Cys Asp Asn Trp Ile
65                  70                  75                  80

Arg Thr Phe Val Pro Ser Leu Gln Pro Gly Gln Phe Lys Leu Gly Asp
                85                  90                  95

Ile Lys Lys Tyr Ser Gly Leu Gln Ser Tyr Val Val Arg Val Val Ser
            100                 105                 110

Thr Asn Tyr Ser Gln Phe Ala Ile Val Phe Phe Lys Lys Val Ser Asn
            115                 120                 125

Asn Gln Glu Tyr Phe Lys Thr Thr Leu Tyr Gly Arg Thr Lys Val Leu
        130                 135                 140

Ser Pro Glu Leu Lys Glu Asn Phe Val Arg Phe Ala Lys Ser Leu Gly
145                 150                 155                 160

Leu Ser Asp Asp Asn Ile Ile Phe Pro Val Ala Ile Asp Gln Cys Ile
                165                 170                 175

Asp Gly Gln
```

```
<210> SEQ ID NO 57
<211> LENGTH: 179
<212> TYPE: PRT
<213> ORGANISM: Tursiops truncatus

<400> SEQUENCE: 57
```

Gln Asp Ser Thr Pro Asn Leu Ile Pro Ala Pro Pro Leu Phe Arg Val
1               5                   10                  15

Pro Leu Gln Pro Asn Phe Gln Pro Asp Gln Phe Gln Gly Lys Trp Tyr
            20                  25                  30

Ile Val Gly Leu Ala Gly Asn Ala Phe Lys Lys Glu Lys Gln Gly Gln
        35                  40                  45

Phe Lys Met Tyr Ala Thr Thr Tyr Glu Leu Lys Glu Asp Arg Ser Tyr
    50                  55                  60

Asn Val Thr Ser Ala Leu Leu Arg Asp Glu Arg Cys Asp His Trp Ile
65                  70                  75                  80

Arg Thr Phe Val Pro Ser Ser Arg Pro Gly Gln Phe Thr Leu Gly Asn
                85                  90                  95

Ile Lys Gly Phe Pro Gly Val Gln Ser Tyr Thr Val Arg Val Ala Thr
            100                 105                 110

Thr Asn Tyr Asn Gln Phe Ala Ile Val Tyr Phe Lys Lys Val Tyr Lys
        115                 120                 125

Asn Gln Glu Tyr Phe Lys Thr Thr Leu Tyr Gly Arg Thr Lys Glu Leu
    130                 135                 140

Thr Pro Gln Leu Lys Glu Asn Phe Ile His Phe Ala Lys Ser Leu Gly
145                 150                 155                 160

Leu Thr Asp Glu Tyr Ile Leu Phe Pro Val Pro Ile Lys Cys Ile
                165                 170                 175

Asp Asp Gln

```
<210> SEQ ID NO 58
<211> LENGTH: 179
<212> TYPE: PRT
<213> ORGANISM: Equus caballus

<400> SEQUENCE: 58
```

Arg Asp Pro Ala Pro Lys Leu Ile Pro Ala Pro Pro Leu Asp Arg Val
1               5                   10                  15

Pro Leu Gln Pro Asp Phe Lys Asp Asp Gln Phe Gln Gly Lys Trp Tyr
            20                  25                  30

Val Val Gly Val Ala Gly Asn Ala Phe Lys Lys Glu Glu Gln Gly Gln
        35                  40                  45

Phe Thr Met Tyr Thr Thr Thr Tyr Glu Leu Lys Glu Asp His Ser Tyr
    50                  55                  60

Asn Val Thr Ser Ile Leu Leu Arg Asp Gln Asn Cys Asp His Trp Ile
65                  70                  75                  80

Arg Thr Phe Ile Pro Ser Ser Gln Pro Gly Gln Phe Asn Leu Gly Asp
                85                  90                  95

Ile Lys Arg Tyr Phe Gly Val Gln Ser Tyr Ile Val Arg Val Ala Asp
            100                 105                 110

Thr Asp Tyr Asn Gln Phe Ala Ile Val Phe Phe Arg Lys Val Tyr Lys
        115                 120                 125

Asn Gln Glu Tyr Phe Lys Thr Thr Leu Tyr Arg Arg Thr Lys Glu Leu
    130                 135                 140

Thr Pro Glu Leu Arg Glu Lys Phe Ile Ser Phe Ala Lys Ser Leu Gly
145                 150                 155                 160

Leu Thr Asp Asp His Ile Ile Phe Pro Val Pro Ile Asp Gln Cys Ile
                165                 170                 175

Asp Glu Glu

<210> SEQ ID NO 59
<211> LENGTH: 177
<212> TYPE: PRT
<213> ORGANISM: Microcebus murinus

<400> SEQUENCE: 59

Gln Asp Ser Lys Glu Lys Leu Ile Pro Ala Pro Pro Leu Leu Arg Val
1               5                   10                  15

Pro Leu Gln Pro Asp Phe Gln Asp Asp Gln Phe Gln Gly Lys Trp Tyr
            20                  25                  30

Val Val Gly Leu Ala Gly Asn Ala Val Ser Lys Glu Glu Gln Gly Gln
        35                  40                  45

Phe Thr Met Tyr Thr Thr Thr Tyr Glu Leu Lys Asp His Ser Tyr Asn
    50                  55                  60

Val Thr Ser Thr Leu Leu Arg Asn Gly Lys Cys Asp Tyr Trp Ile Arg
65                  70                  75                  80

Thr Phe Val Leu Thr Ser Gln Pro Gly Gln Phe Ala Leu Gly Asn Ile
                85                  90                  95

Asn Arg Tyr Pro Gly Ile Gln Ser Tyr Thr Val Arg Val Val Thr Thr
            100                 105                 110

Asn Tyr Asn Gln Phe Ala Ile Val Phe Phe Lys Lys Val Ser Glu Asn
        115                 120                 125

Lys Glu Tyr Phe Lys Thr Thr Leu Tyr Gly Arg Thr Lys Glu Leu Pro
    130                 135                 140

Pro Glu Leu Lys Glu Asn Phe Ile Arg Phe Ala Lys Ser Leu Gly Leu
145                 150                 155                 160

Thr Glu Asp His Ile Ile Tyr Pro Val Pro Ile Asp Gln Cys Ile Asp
                165                 170                 175

Asp

<210> SEQ ID NO 60
<211> LENGTH: 179
<212> TYPE: PRT
<213> ORGANISM: Loxodonta africana

<400> SEQUENCE: 60

Gln Thr His Ser Pro Thr Leu Ile Pro Ala Pro Pro Leu Leu Arg Val
1               5                   10                  15

Pro Leu Gln Pro Asp Phe Gln Asp Asp Lys Phe Gln Gly Lys Trp Tyr
            20                  25                  30

Val Ile Gly Leu Ala Gly Asn Ala Val Glu Lys Lys Glu Gln Gly Gln
        35                  40                  45

Phe Lys Met Tyr Thr Thr Thr Tyr Glu Leu Lys Glu Asp Gly Ser Tyr
    50                  55                  60

Asn Val Thr Ser Thr Leu Leu Gln Glu Asp Gly Lys Cys Ser Tyr Trp
65                  70                  75                  80

Ile Arg Thr Phe Val Pro Ser Phe Gln Pro Gly Gln Phe Asn Leu Gly
                85                  90                  95

Asn Ile Lys Asn Phe Pro Gly Leu Gln Ser Tyr Thr Val Arg Val Thr
            100                 105                 110

Ala Thr Asn Tyr Asn Gln Phe Ala Ile Val Phe Phe Lys Lys Val Ser

```
            115                 120                 125
Lys Asn Gly Glu Tyr Phe Lys Thr Thr Leu Tyr Gly Arg Thr Lys Glu
            130                 135                 140
Leu Thr Pro Glu Leu Lys Glu Arg Phe Ile Arg Phe Ala Lys Ser Leu
145                 150                 155                 160
Gly Leu Ser Asp His Ile Ile Phe Pro Val Pro Ile Asp Arg Cys Ile
                165                 170                 175
Asp Asp Ala

<210> SEQ ID NO 61
<211> LENGTH: 178
<212> TYPE: PRT
<213> ORGANISM: Provacia capensis

<400> SEQUENCE: 61

Gln Glu Pro Thr Pro Leu Ile Pro Ala Pro Pro Leu Ser Ser Ile Pro
1               5                   10                  15

Leu Lys Pro Asn Phe His Asn Asp Lys Phe Gln Gly Lys Trp Tyr Val
            20                  25                  30

Val Gly Val Ala Gly Asn Ala Ile Thr Lys Glu Lys Asp Pro Ser Leu
        35                  40                  45

Met Tyr Thr Thr Thr Tyr Glu Leu Arg Asp Asp Gly Ser Tyr Asn Val
    50                  55                  60

Thr Ser Thr Gln Phe Arg Glu Lys Ile Asn Cys Thr His Trp Thr Arg
65                  70                  75                  80

Thr Phe Val Pro Thr Ser Gln Pro Gly Gln Phe Ser Leu Gly Asn Ile
                85                  90                  95

Asp Lys Tyr Pro His Leu Ser Ser Tyr Thr Val Arg Val Thr Ala Thr
            100                 105                 110

Asn Tyr Asn Tyr Phe Ala Ile Val Tyr Phe Lys Lys Val Ser Lys Asn
        115                 120                 125

Gln Glu Tyr Phe Lys Thr Thr Leu Tyr Lys Arg Ile Lys Lys Leu Thr
    130                 135                 140

His Gly Leu Lys Lys His Phe Ile Gln Phe Ala Lys Ser Leu Gly Leu
145                 150                 155                 160

Pro Asp Asn His Ile Thr Phe Leu Val Pro Thr Asp Arg Cys Ile Asp
                165                 170                 175

Asp Ala

<210> SEQ ID NO 62
<211> LENGTH: 178
<212> TYPE: PRT
<213> ORGANISM: Canis familiaris

<400> SEQUENCE: 62

Gln Asp Ser Thr Pro Ser Leu Ile Pro Ala Pro Pro Leu Lys Val
1               5                   10                  15

Pro Leu Gln Pro Asp Phe Gln His Asp Gln Phe Gln Gly Lys Trp Tyr
            20                  25                  30

Val Ile Gly Ile Ala Gly Asn Ile Leu Lys Lys Glu Gly His Gly Gln
        35                  40                  45

Leu Lys Met Tyr Thr Thr Thr Tyr Glu Leu Lys Asp Asp Gln Ser Tyr
    50                  55                  60

Asn Val Thr Ser Thr Leu Leu Arg Asn Glu Arg Cys Asp Tyr Trp Asn
65                  70                  75                  80
```

```
Arg Asp Phe Val Pro Ser Phe Gln Pro Gly Gln Phe Ser Leu Gly Asp
                85                  90                  95

Ile Gln Leu Tyr Pro Gly Val Gln Ser Tyr Leu Val Gln Val Val Ala
            100                 105                 110

Thr Asn Tyr Asn Gln Tyr Ala Leu Val Tyr Phe Arg Lys Val Tyr Lys
            115                 120                 125

Ser Gln Glu Tyr Phe Lys Ile Thr Leu Tyr Gly Arg Thr Lys Glu Leu
            130                 135                 140

Pro Leu Glu Leu Lys Lys Glu Phe Ile Arg Phe Ala Lys Ser Ile Gly
145                 150                 155                 160

Leu Thr Glu Asp His Ile Ile Phe Pro Val Pro Ile Asp Gln Cys Ile
                165                 170                 175

Asp Glu

<210> SEQ ID NO 63
<211> LENGTH: 20
<212> TYPE: PRT
<213> ORGANISM: Artificial Sequence
<220> FEATURE:
<223> OTHER INFORMATION: signal peptide

<400> SEQUENCE: 63

Met Glu Thr Asp Thr Leu Leu Leu Trp Val Leu Leu Leu Trp Val Pro
1               5                   10                  15

Gly Ser Thr Gly
            20

<210> SEQ ID NO 64
<211> LENGTH: 7
<212> TYPE: PRT
<213> ORGANISM: Artificial Sequence
<220> FEATURE:
<223> OTHER INFORMATION: TEV protease site

<400> SEQUENCE: 64

Glu Asn Leu Tyr Phe Gln Lys
1               5

<210> SEQ ID NO 65
<211> LENGTH: 133
<212> TYPE: PRT
<213> ORGANISM: Homo sapiens

<400> SEQUENCE: 65

Asn Gln Glu Val Gln Ile Pro Leu Thr Glu Ser Tyr Cys Gly Pro Cys
1               5                   10                  15

Pro Lys Asn Trp Ile Cys Tyr Lys Asn Asn Cys Tyr Gln Phe Phe Asp
            20                  25                  30

Glu Ser Lys Asn Trp Tyr Glu Ser Gln Ala Ser Cys Met Ser Gln Asn
            35                  40                  45

Ala Ser Leu Leu Lys Val Tyr Ser Lys Glu Asp Gln Asp Leu Leu Lys
        50                  55                  60

Leu Val Lys Ser Tyr His Trp Met Gly Leu Val His Ile Pro Thr Asn
65                  70                  75                  80

Gly Ser Trp Gln Trp Glu Asp Gly Ser Ile Leu Ser Pro Asn Leu Leu
                85                  90                  95

Thr Ile Ile Glu Met Gln Lys Gly Asp Cys Ala Leu Tyr Ala Ser Ser
            100                 105                 110

Phe Lys Gly Tyr Ile Glu Asn Cys Ser Thr Pro Asn Thr Tyr Ile Cys
```

```
                  115                 120                 125

Met Gln Arg Thr Val
        130

<210> SEQ ID NO 66
<211> LENGTH: 129
<212> TYPE: PRT
<213> ORGANISM: Homo sapiens

<400> SEQUENCE: 66

Gln Ile Pro Leu Thr Glu Ser Tyr Cys Gly Pro Cys Pro Lys Asn Trp
1               5                   10                  15

Ile Cys Tyr Lys Asn Asn Cys Tyr Gln Phe Phe Asp Glu Ser Lys Asn
            20                  25                  30

Trp Tyr Glu Ser Gln Ala Ser Cys Met Ser Gln Asn Ala Ser Leu Leu
        35                  40                  45

Lys Val Tyr Ser Lys Glu Asp Gln Asp Leu Leu Lys Leu Val Lys Ser
    50                  55                  60

Tyr His Trp Met Gly Leu Val His Ile Pro Thr Asn Gly Ser Trp Gln
65                  70                  75                  80

Trp Glu Asp Gly Ser Ile Leu Ser Pro Asn Leu Leu Thr Ile Ile Glu
                85                  90                  95

Met Gln Lys Gly Asp Cys Ala Leu Tyr Ala Ser Ser Phe Lys Gly Tyr
            100                 105                 110

Ile Glu Asn Cys Ser Thr Pro Asn Thr Tyr Ile Cys Met Gln Arg Thr
        115                 120                 125

Val

<210> SEQ ID NO 67
<211> LENGTH: 489
<212> TYPE: PRT
<213> ORGANISM: Artificial Sequence
<220> FEATURE:
<223> OTHER INFORMATION: exemplary construct

<400> SEQUENCE: 67

Met Glu Thr Asp Thr Leu Leu Leu Trp Val Leu Leu Leu Trp Val Pro
1               5                   10                  15

Gly Ser Thr Gly Asp Tyr Lys Asp Glu His His His His His His Gly
            20                  25                  30

Gly Ser Gln Asp Ser Thr Ser Asp Leu Ile Pro Ala Pro Pro Leu Ser
        35                  40                  45

Lys Val Pro Leu Gln Gln Asn Phe Gln Asp Asn Gln Phe Gln Gly Lys
    50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
            100                 105                 110

Trp Ile Arg Thr Phe Val Pro Gly Cys Gln Pro Gly Glu Phe Thr Leu
        115                 120                 125

Gly Asn Ile Lys Ser Tyr Pro Gly Leu Thr Ser Tyr Leu Val Arg Val
    130                 135                 140

Val Ser Thr Asn Tyr Asn Gln His Ala Met Val Phe Phe Lys Lys Val
145                 150                 155                 160
```

```
Ser Gln Asn Arg Glu Tyr Phe Lys Ile Thr Leu Tyr Gly Arg Thr Lys
            165                 170                 175

Glu Leu Thr Ser Glu Leu Lys Glu Asn Phe Ile Arg Phe Ser Lys Ser
        180                 185                 190

Leu Gly Leu Pro Glu Asn His Ile Val Phe Pro Val Pro Ile Asp Gln
            195                 200                 205

Cys Ile Asp Gly Gly Ser Glu Asn Leu Tyr Phe Gln Lys Ser Gly
            210                 215                 220

Gly Gly Ser Asn Gln Glu Val Gln Ile Pro Leu Thr Glu Ser Tyr Cys
225                 230                 235                 240

Gly Pro Cys Pro Lys Asn Trp Ile Cys Tyr Lys Asn Asn Cys Tyr Gln
                245                 250                 255

Phe Phe Asp Glu Ser Lys Asn Trp Tyr Glu Ser Gln Ala Ser Cys Met
            260                 265                 270

Ser Gln Asn Ala Ser Leu Leu Lys Val Tyr Ser Lys Glu Asp Gln Asp
            275                 280                 285

Leu Leu Lys Leu Val Lys Ser Tyr His Trp Met Gly Leu Val His Ile
            290                 295                 300

Pro Thr Asn Gly Ser Trp Gln Trp Glu Asp Gly Ser Ile Leu Ser Pro
305                 310                 315                 320

Asn Leu Thr Ile Ile Glu Met Gln Lys Gly Asp Cys Ala Leu Tyr
                325                 330                 335

Ala Ser Ser Phe Lys Gly Tyr Ile Glu Asn Cys Ser Thr Pro Asn Thr
            340                 345                 350

Tyr Ile Cys Met Gln Arg Thr Val Gln Ile Pro Leu Thr Glu Ser Tyr
            355                 360                 365

Cys Gly Pro Cys Pro Lys Asn Trp Ile Cys Tyr Lys Asn Asn Cys Tyr
370                 375                 380

Gln Phe Phe Asp Glu Ser Lys Asn Trp Tyr Glu Ser Gln Ala Ser Cys
385                 390                 395                 400

Met Ser Gln Asn Ala Ser Leu Leu Lys Val Tyr Ser Lys Glu Asp Gln
                405                 410                 415

Asp Leu Leu Lys Leu Val Lys Ser Tyr His Trp Met Gly Leu Val His
            420                 425                 430

Ile Pro Thr Asn Gly Ser Trp Gln Trp Glu Asp Gly Ser Ile Leu Ser
            435                 440                 445

Pro Asn Leu Leu Thr Ile Ile Glu Met Gln Lys Gly Asp Cys Ala Leu
            450                 455                 460

Tyr Ala Ser Ser Phe Lys Gly Tyr Ile Glu Asn Cys Ser Thr Pro Asn
465                 470                 475                 480

Thr Tyr Ile Cys Met Gln Arg Thr Val
                485

<210> SEQ ID NO 68
<211> LENGTH: 18
<212> TYPE: PRT
<213> ORGANISM: Artificial Sequence
<220> FEATURE:
<223> OTHER INFORMATION: signal peptide

<400> SEQUENCE: 68

Thr Asp Thr Leu Leu Leu Trp Val Leu Leu Leu Trp Val Pro Gly Ser
1               5                   10                  15

Thr Gly
```

```
<210> SEQ ID NO 69
<211> LENGTH: 4
<212> TYPE: PRT
<213> ORGANISM: Artificial Sequence
<220> FEATURE:
<223> OTHER INFORMATION: Flag tag

<400> SEQUENCE: 69

Asp Tyr Asp Glu
1

<210> SEQ ID NO 70
<211> LENGTH: 5
<212> TYPE: PRT
<213> ORGANISM: Artificial Sequence
<220> FEATURE:
<223> OTHER INFORMATION: linker

<400> SEQUENCE: 70

Ser Gly Gly Gly Ser
1               5

<210> SEQ ID NO 71
<211> LENGTH: 133
<212> TYPE: PRT
<213> ORGANISM: Mus musculus

<400> SEQUENCE: 71

Asn Lys Glu Val Pro Val Ser Ser Arg Glu Gly Tyr Cys Gly Pro Cys
1               5                   10                  15

Pro Asn Asn Trp Ile Cys His Arg Asn Asn Cys Tyr Gln Phe Phe Asn
            20                  25                  30

Glu Glu Lys Thr Trp Asn Gln Ser Gln Ala Ser Cys Leu Ser Gln Asn
        35                  40                  45

Ser Ser Leu Leu Lys Ile Tyr Ser Lys Glu Glu Gln Asp Phe Leu Lys
    50                  55                  60

Leu Val Lys Ser Tyr His Trp Met Gly Leu Val Gln Ile Pro Ala Asn
65                  70                  75                  80

Gly Ser Trp Gln Trp Glu Asp Gly Ser Ser Leu Ser Tyr Asn Gln Leu
                85                  90                  95

Thr Leu Val Glu Ile Pro Lys Gly Ser Cys Ala Val Tyr Gly Ser Ser
            100                 105                 110

Phe Lys Ala Tyr Thr Glu Asp Cys Ala Asn Leu Asn Thr Tyr Ile Cys
        115                 120                 125

Met Lys Arg Ala Val
    130

<210> SEQ ID NO 72
<211> LENGTH: 129
<212> TYPE: PRT
<213> ORGANISM: Mus musculus

<400> SEQUENCE: 72

Pro Val Ser Ser Arg Glu Gly Tyr Cys Gly Pro Cys Pro Asn Asn Trp
1               5                   10                  15

Ile Cys His Arg Asn Asn Cys Tyr Gln Phe Phe Asn Glu Glu Lys Thr
            20                  25                  30

Trp Asn Gln Ser Gln Ala Ser Cys Leu Ser Gln Asn Ser Ser Leu Leu
        35                  40                  45

Lys Ile Tyr Ser Lys Glu Glu Gln Asp Phe Leu Lys Leu Val Lys Ser
    50                  55                  60
```

```
Tyr His Trp Met Gly Leu Val Gln Ile Pro Ala Asn Gly Ser Trp Gln
 65                  70                  75                  80

Trp Glu Asp Gly Ser Ser Leu Ser Tyr Asn Gln Leu Thr Leu Val Glu
                 85                  90                  95

Ile Pro Lys Gly Ser Cys Ala Val Tyr Gly Ser Ser Phe Lys Ala Tyr
            100                 105                 110

Thr Glu Asp Cys Ala Asn Leu Asn Thr Tyr Ile Cys Met Lys Arg Ala
        115                 120                 125

Val

<210> SEQ ID NO 73
<211> LENGTH: 486
<212> TYPE: PRT
<213> ORGANISM: Artificial Sequence
<220> FEATURE:
<223> OTHER INFORMATION: exemplary construct

<400> SEQUENCE: 73

Thr Asp Thr Leu Leu Leu Trp Val Leu Leu Leu Trp Val Pro Gly Ser
 1               5                  10                  15

Thr Gly Asp Tyr Asp Glu His His His His His Gly Gly Ser Gln
             20                  25                  30

Asp Ser Thr Ser Asp Leu Ile Pro Ala Pro Pro Leu Ser Lys Val Pro
         35                  40                  45

Leu Gln Gln Asn Phe Gln Asp Asn Gln Phe Gln Gly Lys Trp Tyr Val
     50                  55                  60

Val Gly Leu Ala Gly Asn Ala Ile Leu Arg Glu Asp Lys Asp Pro Gln
 65                  70                  75                  80

Lys Met Tyr Ala Thr Ile Tyr Glu Leu Lys Glu Asp Lys Ser Tyr Asn
                 85                  90                  95

Val Thr Ser Val Leu Phe Arg Lys Lys Lys Cys Asp Tyr Trp Ile Arg
            100                 105                 110

Thr Phe Val Pro Gly Cys Gln Pro Gly Glu Phe Thr Leu Gly Asn Ile
        115                 120                 125

Lys Ser Tyr Pro Gly Leu Thr Ser Tyr Leu Val Arg Val Val Ser Thr
130                 135                 140

Asn Tyr Asn Gln His Ala Met Val Phe Phe Lys Lys Val Ser Gln Asn
145                 150                 155                 160

Arg Glu Tyr Phe Lys Ile Thr Leu Tyr Gly Arg Thr Lys Glu Leu Thr
                165                 170                 175

Ser Glu Leu Lys Glu Asn Phe Ile Arg Phe Ser Lys Ser Leu Gly Leu
            180                 185                 190

Pro Glu Asn His Ile Val Phe Pro Val Pro Ile Asp Gln Cys Ile Asp
        195                 200                 205

Gly Gly Gly Ser Glu Asn Leu Tyr Phe Gln Lys Ser Gly Gly Gly Ser
    210                 215                 220

Asn Lys Glu Val Pro Val Ser Arg Glu Gly Tyr Cys Gly Pro Cys
225                 230                 235                 240

Pro Asn Asn Trp Ile Cys His Arg Asn Asn Cys Tyr Gln Phe Phe Asn
                245                 250                 255

Glu Glu Lys Thr Trp Asn Gln Ser Gln Ala Ser Cys Leu Ser Gln Asn
            260                 265                 270

Ser Ser Leu Leu Lys Ile Tyr Ser Lys Glu Glu Gln Asp Phe Leu Lys
        275                 280                 285
```

-continued

```
Leu Val Lys Ser Tyr His Trp Met Gly Leu Val Gln Ile Pro Ala Asn
        290                 295                 300

Gly Ser Trp Gln Trp Glu Asp Gly Ser Ser Leu Ser Tyr Asn Gln Leu
305                 310                 315                 320

Thr Leu Val Glu Ile Pro Lys Gly Ser Cys Ala Val Tyr Gly Ser Ser
                325                 330                 335

Phe Lys Ala Tyr Thr Glu Asp Cys Ala Asn Leu Asn Thr Tyr Ile Cys
                340                 345                 350

Met Lys Arg Ala Val Pro Val Ser Arg Glu Gly Tyr Cys Gly Pro
            355                 360                 365

Cys Pro Asn Asn Trp Ile Cys His Arg Asn Asn Cys Tyr Gln Phe Phe
370                 375                 380

Asn Glu Glu Lys Thr Trp Asn Gln Ser Gln Ala Ser Cys Leu Ser Gln
385                 390                 395                 400

Asn Ser Ser Leu Leu Lys Ile Tyr Ser Lys Glu Gln Asp Phe Leu
                405                 410                 415

Lys Leu Val Lys Ser Tyr His Trp Met Gly Leu Val Gln Ile Pro Ala
                420                 425                 430

Asn Gly Ser Trp Gln Trp Glu Asp Gly Ser Ser Leu Ser Tyr Asn Gln
            435                 440                 445

Leu Thr Leu Val Glu Ile Pro Lys Gly Ser Cys Ala Val Tyr Gly Ser
450                 455                 460

Ser Phe Lys Ala Tyr Thr Glu Asp Cys Ala Asn Leu Asn Thr Tyr Ile
465                 470                 475                 480

Cys Met Lys Arg Ala Val
                485

<210> SEQ ID NO 74
<211> LENGTH: 8
<212> TYPE: PRT
<213> ORGANISM: Artificial Sequence
<220> FEATURE:
<223> OTHER INFORMATION: Flag tag

<400> SEQUENCE: 74

Asp Tyr Lys Asp Asp Asp Asp Lys
1               5

<210> SEQ ID NO 75
<211> LENGTH: 6
<212> TYPE: PRT
<213> ORGANISM: Artificial Sequence
<220> FEATURE:
<223> OTHER INFORMATION: TEV scission site

<400> SEQUENCE: 75

Glu Asp Leu Tyr Phe Gln
1               5

<210> SEQ ID NO 76
<211> LENGTH: 216
<212> TYPE: PRT
<213> ORGANISM: Homo sapiens

<400> SEQUENCE: 76

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30
```

```
Arg Trp Gln Lys Gln Arg Cys Pro Val Val Lys Ser Lys Cys Arg Glu
        35                  40                  45

Asn Ala Ser Pro Phe Phe Phe Cys Cys Phe Ile Ala Val Ala Met Gly
 50                  55                  60

Ile Arg Phe Ile Ile Met Val Thr Ile Trp Ser Ala Val Phe Leu Asn
 65                  70                  75                  80

Ser Leu Phe Asn Gln Glu Val Gln Ile Pro Leu Thr Glu Ser Tyr Cys
                 85                  90                  95

Gly Pro Cys Pro Lys Asn Trp Ile Cys Tyr Lys Asn Asn Cys Tyr Gln
            100                 105                 110

Phe Phe Asp Glu Ser Lys Asn Trp Tyr Glu Ser Gln Ala Ser Cys Met
            115                 120                 125

Ser Gln Asn Ala Ser Leu Leu Lys Val Tyr Ser Lys Glu Asp Gln Asp
130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
            180                 185                 190

Ala Ser Ser Phe Lys Gly Tyr Ile Glu Asn Cys Ser Thr Pro Asn Thr
            195                 200                 205

Tyr Ile Cys Met Gln Arg Thr Val
            210                 215

<210> SEQ ID NO 77
<211> LENGTH: 177
<212> TYPE: PRT
<213> ORGANISM: Homo sapiens

<400> SEQUENCE: 77

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp
```

```
<210> SEQ ID NO 78
<211> LENGTH: 551
<212> TYPE: PRT
<213> ORGANISM: Artificial Sequence
<220> FEATURE:
<223> OTHER INFORMATION: Exemplary construct

<400> SEQUENCE: 78

Met Glu Thr Asp Thr Leu Leu Leu Trp Val Leu Leu Trp Val Pro
1               5                   10                  15

Gly Ser Thr Gly Asp Tyr Lys Asp Glu His His His His His Gly
                20                  25                  30

Gly Ser Gln Asp Ser Thr Ser Asp Leu Ile Pro Ala Pro Pro Leu Ser
            35                  40                  45

Lys Val Pro Leu Gln Gln Asn Phe Gln Asp Asn Gln Phe Gln Gly Lys
            50                  55                  60

Trp Tyr Val Val Gly Leu Ala Gly Asn Ala Ile Leu Arg Glu Asp Lys
65                  70                  75                  80

Asp Pro Gln Lys Met Tyr Ala Thr Ile Tyr Glu Leu Lys Glu Asp Lys
                85                  90                  95

Ser Tyr Asn Val Thr Ser Val Leu Phe Arg Lys Lys Lys Cys Asp Tyr
                100                 105                 110

Trp Ile Arg Thr Phe Val Pro Gly Ser Gln Pro Gly Glu Phe Thr Leu
                115                 120                 125

Gly Asn Ile Lys Ser Tyr Pro Gly Leu Thr Ser Tyr Leu Val Arg Val
            130                 135                 140

Val Ser Thr Asn Tyr Asn Gln His Ala Met Val Phe Phe Lys Lys Val
145                 150                 155                 160

Ser Gln Asn Arg Glu Tyr Phe Lys Ile Thr Leu Tyr Gly Arg Thr Lys
                165                 170                 175

Glu Leu Thr Ser Glu Leu Lys Glu Asn Phe Ile Arg Phe Ser Lys Ser
                180                 185                 190

Leu Gly Leu Pro Glu Asn His Ile Val Phe Pro Val Pro Ile Asp Gln
            195                 200                 205

Cys Ile Asp Gly Gly Gly Ser Glu Asn Leu Tyr Phe Gln Gly Ser Arg
210                 215                 220

Ser Ala Gly Ala His Ala Gly Trp Glu Thr Pro Glu Gly Cys Glu Gln
225                 230                 235                 240

Val Leu Thr Gly Lys Arg Leu Met Gln Cys Leu Pro Asn Pro Glu Asp
                245                 250                 255

Val Lys Met Ala Leu Glu Val Tyr Lys Leu Ser Leu Glu Ile Glu Gln
                260                 265                 270

Leu Glu Leu Gln Arg Asp Ser Ala Arg Gln Ser Thr Leu Asp Lys Glu
                275                 280                 285

Leu Asn Gln Glu Val Gln Ile Pro Leu Thr Glu Ser Tyr Cys Gly Pro
            290                 295                 300

Cys Pro Lys Asn Trp Ile Cys Tyr Lys Asn Asn Cys Tyr Gln Phe Phe
305                 310                 315                 320

Asp Glu Ser Lys Asn Trp Tyr Glu Ser Gln Ala Ser Cys Met Ser Gln
                325                 330                 335

Asn Ala Ser Leu Leu Lys Val Tyr Ser Lys Glu Asp Gln Asp Leu Leu
            340                 345                 350

Lys Leu Val Lys Ser Tyr His Trp Met Gly Leu Val His Ile Pro Thr
                355                 360                 365
```

Asn Gly Ser Trp Gln Trp Glu Asp Gly Ser Ile Leu Ser Pro Asn Leu
    370                 375                 380

Leu Thr Ile Ile Glu Met Gln Lys Gly Asp Cys Ala Leu Tyr Ala Ser
385                 390                 395                 400

Ser Phe Lys Gly Tyr Ile Glu Asn Cys Ser Thr Pro Asn Thr Tyr Ile
                405                 410                 415

Cys Met Gln Arg Thr Val Gln Ile Pro Leu Thr Glu Ser Tyr Cys Gly
            420                 425                 430

Pro Cys Pro Lys Asn Trp Ile Cys Tyr Lys Asn Asn Cys Tyr Gln Phe
        435                 440                 445

Phe Asp Glu Ser Lys Asn Trp Tyr Glu Ser Gln Ala Ser Cys Met Ser
    450                 455                 460

Gln Asn Ala Ser Leu Leu Lys Val Tyr Ser Lys Glu Asp Gln Asp Leu
465                 470                 475                 480

Leu Lys Leu Val Lys Ser Tyr His Trp Met Gly Leu Val His Ile Pro
                485                 490                 495

Thr Asn Gly Ser Trp Gln Trp Glu Asp Gly Ser Ile Leu Ser Pro Asn
            500                 505                 510

Leu Leu Thr Ile Ile Glu Met Gln Lys Gly Asp Cys Ala Leu Tyr Ala
        515                 520                 525

Ser Ser Phe Lys Gly Tyr Ile Glu Asn Cys Ser Thr Pro Asn Thr Tyr
    530                 535                 540

Ile Cys Met Gln Arg Thr Val
545                 550

<210> SEQ ID NO 79
<211> LENGTH: 123
<212> TYPE: PRT
<213> ORGANISM: Homo sapiens

<400> SEQUENCE: 79

Ser Tyr Cys Gly Pro Cys Pro Lys Asn Trp Ile Cys Tyr Lys Asn Asn
1               5                   10                  15

Cys Tyr Gln Phe Phe Asp Glu Ser Lys Asn Trp Tyr Glu Ser Gln Ala
            20                  25                  30

Ser Cys Met Ser Gln Asn Ala Ser Leu Leu Lys Val Tyr Ser Lys Glu
        35                  40                  45

Asp Gln Asp Leu Leu Lys Leu Val Lys Ser Tyr His Trp Met Gly Leu
    50                  55                  60

Val His Ile Pro Thr Asn Gly Ser Trp Gln Trp Glu Asp Gly Ser Ile
65                  70                  75                  80

Leu Ser Pro Asn Leu Leu Thr Ile Ile Glu Met Gln Lys Gly Asp Cys
                85                  90                  95

Ala Leu Tyr Ala Ser Ser Phe Lys Gly Tyr Ile Glu Asn Cys Ser Thr
            100                 105                 110

Pro Asn Thr Tyr Ile Cys Met Gln Arg Thr Val
        115                 120

<210> SEQ ID NO 80
<211> LENGTH: 68
<212> TYPE: PRT
<213> ORGANISM: Homo sapiens

<400> SEQUENCE: 80

Gly Ser Arg Ser Ala Gly Ala His Ala Gly Trp Glu Thr Pro Glu Gly
1               5                   10                  15

```
Cys Glu Gln Val Leu Thr Gly Lys Arg Leu Met Gln Cys Leu Pro Asn
             20                  25                  30

Pro Glu Asp Val Lys Met Ala Leu Glu Val Tyr Lys Leu Ser Leu Glu
         35                  40                  45

Ile Glu Gln Leu Glu Leu Gln Arg Asp Ser Ala Arg Gln Ser Thr Leu
 50                  55                  60

Asp Lys Glu Leu
 65

<210> SEQ ID NO 81
<211> LENGTH: 10
<212> TYPE: PRT
<213> ORGANISM: Homo sapiens

<400> SEQUENCE: 81

Asn Gln Glu Val Gln Ile Pro Leu Thr Glu
 1               5                   10

<210> SEQ ID NO 82
<211> LENGTH: 6
<212> TYPE: PRT
<213> ORGANISM: Homo sapiens

<400> SEQUENCE: 82

Gln Ile Pro Leu Thr Glu
 1               5

<210> SEQ ID NO 83
<211> LENGTH: 330
<212> TYPE: PRT
<213> ORGANISM: Homo sapiens

<400> SEQUENCE: 83

Gly Ser Arg Ser Ala Gly Ala His Ala Gly Trp Glu Thr Pro Glu Gly
 1               5                   10                  15

Cys Glu Gln Val Leu Thr Gly Lys Arg Leu Met Gln Cys Leu Pro Asn
             20                  25                  30

Pro Glu Asp Val Lys Met Ala Leu Glu Val Tyr Lys Leu Ser Leu Glu
         35                  40                  45

Ile Glu Gln Leu Glu Leu Gln Arg Asp Ser Ala Arg Gln Ser Thr Leu
 50                  55                  60

Asp Lys Glu Leu Asn Gln Glu Val Gln Ile Pro Leu Thr Glu Ser Tyr
 65                  70                  75                  80

Cys Gly Pro Cys Pro Lys Asn Trp Ile Cys Tyr Lys Asn Asn Cys Tyr
                 85                  90                  95

Gln Phe Phe Asp Glu Ser Lys Asn Trp Tyr Glu Ser Gln Ala Ser Cys
            100                 105                 110

Met Ser Gln Asn Ala Ser Leu Leu Lys Val Tyr Ser Lys Glu Asp Gln
        115                 120                 125

Asp Leu Leu Lys Leu Val Lys Ser Tyr His Trp Met Gly Leu Val His
    130                 135                 140

Ile Pro Thr Asn Gly Ser Trp Gln Trp Glu Asp Gly Ser Ile Leu Ser
145                 150                 155                 160

Pro Asn Leu Leu Thr Ile Ile Glu Met Gln Lys Gly Asp Cys Ala Leu
                165                 170                 175

Tyr Ala Ser Ser Phe Lys Gly Tyr Ile Glu Asn Cys Ser Thr Pro Asn
            180                 185                 190

Thr Tyr Ile Cys Met Gln Arg Thr Val Gln Ile Pro Leu Thr Glu Ser
```

-continued

```
              195                 200                 205
Tyr Cys Gly Pro Cys Pro Lys Asn Trp Ile Cys Tyr Lys Asn Asn Cys
    210                 215                 220

Tyr Gln Phe Phe Asp Glu Ser Lys Asn Trp Tyr Glu Ser Gln Ala Ser
225                 230                 235                 240

Cys Met Ser Gln Asn Ala Ser Leu Leu Lys Val Tyr Ser Lys Glu Asp
                245                 250                 255

Gln Asp Leu Leu Lys Leu Val Lys Ser Tyr His Trp Met Gly Leu Val
            260                 265                 270

His Ile Pro Thr Asn Gly Ser Trp Gln Trp Glu Asp Gly Ser Ile Leu
        275                 280                 285

Ser Pro Asn Leu Leu Thr Ile Ile Glu Met Gln Lys Gly Asp Cys Ala
    290                 295                 300

Leu Tyr Ala Ser Ser Phe Lys Gly Tyr Ile Glu Asn Cys Ser Thr Pro
305                 310                 315                 320

Asn Thr Tyr Ile Cys Met Gln Arg Thr Val
                325                 330
```